United States Patent
Ellis et al.

(10) Patent No.: US 6,469,012 B1
(45) Date of Patent: Oct. 22, 2002

(54) PYRAZOLOPYRIMIDINONES FOR THE TREATMENT OF IMPOTENCE

(75) Inventors: Peter Ellis; Nicholas Kenneth Terrett, both of Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 08/549,792

(22) PCT Filed: May 13, 1994

(86) PCT No.: PCT/EP94/01580

§ 371 (c)(1),
(2), (4) Date: Mar. 4, 1996

(87) PCT Pub. No.: WO94/28902

PCT Pub. Date: Dec. 22, 1994

(30) Foreign Application Priority Data

Jun. 9, 1993 (GB) .............................................. 9311920

(51) Int. Cl.⁷ ........................ A61K 31/519; A61P 15/10
(52) U.S. Cl. ....................................... 514/258; 514/929
(58) Field of Search ................................. 514/258, 929

(56) References Cited

U.S. PATENT DOCUMENTS

| | | | |
|---|---|---|---|
| 3,987,160 A | | 10/1976 | Broughton et al. |
| 4,521,421 A | * | 6/1985 | Foreman ...................... 514/267 |
| 5,145,852 A | | 9/1992 | Virag ......................... 514/253 |
| 5,270,323 A | | 12/1993 | Milne, Jr. et al. |
| 5,278,192 A | | 1/1994 | Fung et al. |
| 5,399,581 A | | 3/1995 | Laragh |
| 5,436,272 A | | 7/1995 | Scheinbaum |
| 5,489,610 A | | 2/1996 | Fung et al. |
| 5,565,466 A | | 10/1996 | Gioco et al. |
| 5,891,904 A | | 4/1999 | Stief et al. |
| 6,037,346 A | | 3/2000 | Doherty, Jr. et al. |

FOREIGN PATENT DOCUMENTS

| | | | |
|---|---|---|---|
| CN | 93117097.4 | 7/2000 | |
| DE | 4230755 | 3/1994 | |
| EP | 0143357 | 6/1985 | |
| EP | 0-201-188 | 12/1986 | |
| EP | 0439320 A1 | 7/1991 | |
| EP | 0463756 | 1/1992 | |
| EP | 0526004 | 2/1993 | |
| FR | 2547501 | 12/1984 | |
| JP | 5310599 | 4/1978 | |
| JP | 03044324 A | 2/1991 | |
| JP | 3044324 | 2/1991 | |
| JP | 03044324 | 2/1991 | .......... A61K/31/52 |
| JP | 9503996 | 4/1997 | |
| WO | 89/10123 A1 | 6/1989 | |
| WO | 8910123 | 11/1989 | |
| WO | 94/28902 | 12/1994 | |
| WO | 96/16644 | 6/1996 | |
| WO | 99/21562 | 5/1999 | |
| WO | 00/66114 | 11/2000 | |

OTHER PUBLICATIONS

WPIDS abstract, AN 95–051606 [07], Coates et al., WO 9429277 (1994).*

Judgment of Nov. 8, 2000.

(List continued on next page.)

Primary Examiner—Edward J. Webman
(74) Attorney, Agent, or Firm—Peter C. Richardson; Gregg C. Benson; James T. Jones

(57) ABSTRACT

The use of a compound of formula (I)

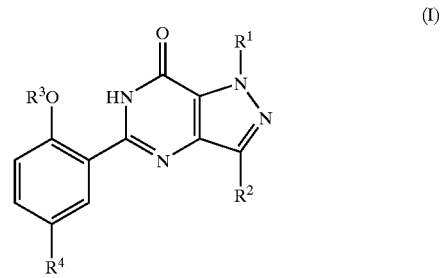

wherein $R^1$ is H; $C_1$–$C_3$ alkyl; $C_1$–$C_3$ perfluoroalkyl; or $C_3$–$C_5$ cycloalkyl; $R^2$ is H; optionally substituted $C_1$–$C_6$ alkyl; $C_1$–$C_3$ perfluoroalkyl; or $C_3$–$C_6$ cycloalkyl; $R^3$ is optionally substituted $C_1$–$C_6$ alkyl; $C_1$–$C_6$ perfluoroalkyl; $C_3$–$C_5$ cycloalkyl; $C_3$–$C_6$ alkenyl; or $C_3$–$C_6$ alkynyl; $R^4$ is optionally substituted $C_1$–$C_4$ alkyl, $C_2$–$C_4$ alkenyl, $C_2$–$C_4$ alkanoyl, (hydroxy)$C_2$–$C_4$ alkyl or ($C_2$–$C_3$ alkoxy)$C_1$–$C_2$ alkyl; $CONR^5R^6$; $CO_2R^7$; halo; $NR^5R^6$; $NHSO_2NR^5R^6$; $NHSO_2R^8$; $SO_2NR^9R^{10}$; or phenyl, pyridyl, pyrimidinyl, imidazolyl, oxazolyl, thiazolyl, thienyl or triazolyl any of which is optionally substituted with methyl; $R^5$ and $R^6$ are each independently H or $C_1$–$C_4$ alkyl, or together with the nitrogen atom to which they are attached form an optionally substituted pyrrolidinyl, piperidino, morpholino, 4-N($R^{11}$)-piperazinyl or imidazolyl group; $R^7$ is H or $C_1$–$C_4$ alkyl; $R^8$ is optionally substituted $C_1$–$C_3$ alkyl; $R^9$ and $R^{10}$ together with the nitrogen atom to which they are attached form an optionally substituted pyrrolidinyl, piperidino, morpholino or 4-N($R^{12}$)-piperazinyl group; $R^{11}$ is H; optionally substituted $C_1$–$C_3$ alkyl; (hydroxy)$C_2$–$C_3$ alkyl; or $C_1$–$C_4$ alkanoyl; $R^{12}$ is H; optionally substituted $C_1$–$C_6$ alkyl; $CONR^{13}R^{14}$; $CSNR^{13}R^{14}$; or $C(NH)NR^{13}R^{14}$; and R?13? and $R^{14}$ are each independently H; $C_1$–$C_4$ alkyl; or substituted $C_2$–$C_4$ alkyl; or a pharmaceutically acceptable salt thereof, or a pharmaceutical composition containing either entity, for the manufacture of a medicament for the curative or prophylactic treatment of erectile dysfunction in a male animal, including man; a pharmaceutical composition for said treatment; and a method of said treatment of said male animal with said pharmaceutical composition or with said either entity.

26 Claims, No Drawings

OTHER PUBLICATIONS

Annexes to Appellant's Notice of Appeal.
Respondent's Notice in the Court of Appeal.
Trial Transcripts—Nov. 26–30, 2000.
Trail Transcripts—Dec. 17–19, 2000.
Pfizer—Exhibits of the Opening Speeches.
Bayer Exhibits (2 volumes).
Trial Transcript—Oct. 4, 2000.
Trial Transcript—Oct. 5, 2000.
Trial Transcript—Oct. 6, 2000.
Trial Transcript—Oct. 10, 2000.
Trial Transcript—Oct. 11, 2000.
Trial Transcript—Oct. 12, 2000.
Trial Transcript—Oct. 13, 2000.
Trial Transcript—Oct. 17, 2000.
Trial Transcript—Oct. 18, 2000.
Exhibits Produced at Trial.
Resolution No. 00112 dated Jan. 18, 2000.
Action to declare void and to re–establish the right of Pfizer Research and Development Company.
Declaration of Alonso Acuna Canas.
Declaration of Cesar Jaramillo.
Original Writ of Summons.
Original First Pleadings Regarding Jurisdiction, Admissibility of Certain Claims and Setting Aside Certain Parties.
Original Second Pleadings Containing Counterclaim for Abuse of Procedure.
Original Third Pleadings Regarding Jurisdiction and Admissibility of Claims.
Original Fourth Pleadings Regarding Jurisdiction and Admissibility of Claims.
EPO Preliminary Opinion.
Submission to EPO dated Dec. 21, 2000.
Letter to EPO dated Dec. 30, 2000.
Transcript of Ian Eardley with Attachments.
Offer of Information (Japan) citing 7 documents.
Offer of Information (Japan) citing 12 documents.
Petition for Reconsideration Against Resolution No. 358.
Nullity Action.
Response to the Non–Compliance Action.
Annex A to Petitioner's Skeleton Argument.
Petition.
Re–amended Particulars of Objections.
Answer.
Respondent's Response to Notice to Admit Facts.
Petitioner's response to Notice to Admit Facts.
Voluntary Further Information concerning para 2(I) and 2(IV).
Defendant's Schedule in relation to Commercial Success.
Statement of the Patentee's Case on Claims 10 and 11.
Admissions by Respondent by letters.
Petitioner's Letter to Respondent (Jul. 4, 2000).
Respondent's Notice of Experiments.
Petitioner's Civil Evidence Act Notices and attachments.
Expert Report of Robert Gristwood (w/Annexes).
Expert Report of Lawrence Kruse (w/Annexes).
Expert Report of John Pryor (w/Annexes).
Second Expert Report of Robert Gristwood (w/Annexes).
Third Expert Report of Robert Gristwood.
Sutherland, J Biol Chem, 1958, 32: 1077–1091.
Butcher and Sutherland, Biochem J, 1962, 237: 1244–1250.
Gristwood et al, Br J Pharmacol, 1986, 89: 573P.
Gristwood and Owen, British Journal of Pharmacology, 1986, 87, 91P.
Torphy et al, Journal Pharmacol Exper Ther, 1993, 265: 1213–1223.
Fernandes et al, Am J Prspir Crit Care Med vol. 150, 1384–1390.
Witness Statement of Margaret Bush (w/Annexes).
Witness Statement of Dr. Francois Hyafil (w/Annexes).
Witness Statement of Julianna Jenkins (w/Annexes).
Witness Statement of Kate Loughney (w/Annexes).
Witness Statement of Sharon Wolda (w/Annexes).
Witness Statement of Lothar Uher (w/Annexes).
Witness Statement of Dr. Javier Angulo (w/Annexes).
Second Witness Statement of Dr. Margaret Bush.
Second Witness Statement of Dr. Javier Angulo.
Expert Report of Robert Challis (w/Annexes).
Expert Report of Ian Eardley (w/Annexes).
Expert Report of Louis Ignarro (w/Annexes).
Expert Report of Peter Ellis (w/Annexes).
Expert Report of Robin Leatherbarrow (w/Annexes).
Expert Report of Kenneth Duncan Macrae (w/Annexes).
Expert Report of Dennis Smith (w/Annexes).
Supplementary Expert Report of Kenneth Duncan Macrae (w/Annexes).
Porst, J Urol (1993) 149, 1280–1283.
Challiss et al, Br J Pharmacol (1998) 124, 47–52.
Eardley, Current Opinion in Urology, 3(2): V 24.
Eardley, Current Opinion in Urology, 3(5): II–40.
Gruetter et al, J Cyclic Nucleotide Res 5: 211–124, 1979.
Krall, Fittinghoff and Rajfer, Biol Reprod, 39(4): 913–22.
Tanaka et al, 1992, Xenobiotica, vol. 22, pp 57–64.
Witness Statement of Peter Ellis (w/Annex).
Witness Statement of Dr. Stephen Ballard.
Report of Repeat Experments the subject of the Repsondent's Notice of Experiments dated Aug. 11, 2000 (w/Appendixes).
First Witness Statement of Dr. Kenneth M. Ferguson (w/Exhibits).
First Witness Statement of Mark Thomas Hodgson (w/Exhibits).
Second Witness Statement of Mark Thomas Hodgson (w/Exhibits).
Third Witness Statement of Mark Thomas Hodgson (w/Exhibits).
Fourth Witness Statement of Mark Thomas Hodgson (w/Exhibits).
Fifth Witness Statement of Mark Thomas Hodgson (w/Exhibits).
First Witness Statement of James Michael Marshall (w/Exhibits).
First Witness Statement of Trevor Martin Cook (w/Exhibits).
Second Witness Statement of Trevor Martin Cook (w/Exhibits).
Third Witness Statement of Trevor Martin Cook (w/Exhibits).
Fifth Witness Statement of Trevor Martin Cook.
Sixth Witness Statement of Trevor Martin Cook.
First Witness Statement of Robert Geoffrey Paget Williams (w/Exhibits).
Opposition Statement of Bristol–Myers Squibb.
Tohoku J. Exp. Med. by Yoshlastu Takahashi et al., published in 1991, 165–49–58.
Rote Liste 1992 (Persantin®, INN: Dipyridamole and Trental®, INN: Pentoxifylline), ECV.

Pharmac. Ther. vol. 51, pp–13–31, 1991; by W. Joseph Thompson.
Exhibit 1; Gray's Anatomie, Churchill Livingstone, 38th Edition.
Exhibit 2; Prof. Dr. Med. J. C. Frölich, Oct. 12, 1998.
Br. J. Dis. Chest (1986) 80, 157; by J. Reiser et al.
JAGS 41: 363–366, 1993; by Stanley G. Korenman et al.
Journal of Medicine, vol. 10, No. 6, 1979; by J. L. Ambrus et al.
Br. J. Pharmacol. (1983), 108, 562–568; by J. Cortijo et al.
Arzneimittel–Forschung (Germany), 1988, vol. 38, pp. 379–382; by P. Cazzulani et al.
Abstract 88:6075 from IPA database (1988).
Opposition Statement of Fujisawa.
Physicians' Desk Reference, 46th edition, 1992, p. 409, 905, 1190.
The Journal of Pharmacology and Experimental Therapeutics, 251(3), pp. 1000–1005 (1989), McMahon et al.
British Journal of Diseases of the Chest, 77, p78–86 (1983), Rudd et al.
British Journal of Pharmacology, (1992), 106, p. 1028–1034, de Boer et al.
Biochemical Pharmacology, 46(5), p. 833–839 (1993), Sacki et al.
Opposition Statement of Eisai Co., Ltd.
Journal of Japanese Society of Urology, 83(10, p 1655–1661 (1992), Kawanishi et al.
Trends in Pharmacological Sciences including Toxicological Sciences, 11, No. 4, pp 150–155 (1990, Apr.), Bearo et al.
Hager's Handbuch der Pharmazeutischen Praxis, 4. Aufl., 1971, S. 675–676.
Opposition Statement of Synthelabo.
Angiology. vol. 42(5), 1991, p. 418–420 Kent S. Allenby et al "Pentoxifylline in the treatment of vascular impotence—Case reports".
Clin. Res. vol. 36(1), 123A, 1988, Korenman SG "Treatment of vasculogenic sexual dysfunctionwith pentoxifylline".
Post Graduate Medicine, vol. 88(2), 139–152, 1990 Whithead E. D. "Treatment alternatives for impotence".
Drug Therapy, vol. 19(8), 102–111, 1989, Fishman I. J. "Treating Erectile dysfunction".
Molecular Pharmacology 36(5), 773–781, 1989, Gillespie P. G. Et Beavo J. A. "Inhibition and stimulation of photoreceptor phosphodiesterases by dipyridamole and M&B22, 948".
J. Mol. Cell. Cardio vol. 12(10), 1980, 939–954, 1980, Argel M.I. et al., "Effect of phosphodiesterase inhibitors onheart contractile behaviour, protein kinase activity and cyclic nucleotide level"(abstract).
Physiol. Rev 75(4), 725–748, 1995, Beavo J. A., "Cyclic nucleotide phosphodiesterases: Functional implications of multiple isoforms".
Opposition Statement of Mochida Pharmaceutical Co.
Journal of Urology 147, 4th Supplement, p. 454A, 1992, No. 967, Aronson et al.
Martindale Extra Pharmacopoeia 29th Edition 1989, p. 1423, Heading 14026–m.
A) Notification of refusal of Jun. 19, 1997 in Japanese Patent Application 7501234 B) Response dated Jan. 8, 1998 from the patentees C) Further response dated Feb. 17, 1998 and Tables attached thereto D) Footnotes by the present opponents referring to 4(C).
International Journal of Impotence Research vol. 6, No. 1, Mar. 1994, pp. 33–35.

Opposition Statement of Ortho M$^c$Neil Pharmaceutical, Inc.
Aronson et al (1991) J. Urology 145: Abstract 516–D1.
Kukovetz et al (1979) Naunyn–Schmiedeberg's Arch. Pharmacol. 310: 129–138—D6.
ABPI Data Sheet Compendium 1990–91—D9, pp. 740–742.
Opposition Statement of Eli Lilly and Company.
ABPI Data Sheet Compendium 1991–1992 (Datapharm Publications Limited 1991) p. 588 Entry on Trental.
Trends Pharmacol. Sci. (TiPS), vol. 12, pp. 19 to 27 (1991), Nicholson et al, Differential modulation of tissue function and therapeutic potential of selective inhibitors of cyclic nucleotide phosphodiesterase isoenzymes.
Journal of Urology, vol. 149, 872–877, 1993, Trigo–Rocha et al, The role of cyclic adenosine monophosphate, cyclic guanosine monophosphate, endothelium and nonadrenergic, noncholinergic neurotransmission in canine penile erection.
Int. J. Impotence Res. (1992) 4 Suppl. 2, Abstracts of the 5th World Congress on Impotence, Milan, Sep. 14–17, 1992, Taher et.
Opposition Statement of Bayer AG.
German Gazette for Physicians 86, No. 33, Aug. 17, 1989, C–1436 to 1440, Haer et al.
Postgraduate Medicine, vol. 93, No. 3, Impotence, Feb. 15, 1993, Morley.
von Koenen: "Heil–und Giftpflanzen in Südwestafrika", Akademischer Verlag Windhoek, S.W.A., 1979, p. 61.
J. of Ethnopharmacology, 12 (1984) 35–74, particularly p. 42, Arnold et al.
CNN interactive on line—"Viagra? No, vuka vuka?" Jun. 19, 1998 (www.cnn.com).
Opposition Statement of Tanabe Seiyaku Co., Ltd.
Opposition Statement of Merck Patent Gmblt.
Opposition Statement of Schering–Plough Corp.
Opposition Statement of ICOS Corporation.
English Translation: Rote Liste 1992, pp. 36 073 and 54 108, (Persantin®, INN: Dipyridamole and Trental®, INN: Pentoxyfyline). (Reference 5 from the opposition of Bristol Myers Squibb).
English Translation: Prof. Dr. Med. J. C. Frolich, Oct. 12, 1998. (Exhibit 2 from the opposition of Bristol Myers Squibb).
English Translation: Haen & Emslander: Optimizing Therapy with Methylxanthines; German Gazette for Physicians, 86 (33), 1989, C–1435–C–1437 (Reference D3 from the opposition of Bayer AG).
English Translation: von Koenen: "Heil–und Giftpflanzen in Sudwestafrika", Akademischer Verlag Winkhoek, S.W.A., 1979, p. 61. (Reference D13 from the opposition of Bayer AG).
Patent in Suit.
Application as Filed.
Priority Document.
J. of Urol. (1993), vol. 149(4), p. 285A.
Petitioner's Notice of Experiments.
Disclosure Document # 18 : DN&P 4(7), Sep. 1991.
Disclosure Document # 110: The Lancet, vol. 340. Oct. 10, 1992.
Disclosure Document # 117: Science, vol. 258. Dec. 18, 1992.
Disclosure Document # 368: Pfizer's Public Affairs Briefing: Press Reports on Clinical Trials of UK–92,480 Jan. 1995.
Reports of Repeats of the Petitioner's Notice of Experiments 1–4.
Fourth Witness Statement of Trevor Martin Cook.

Grounds of Opposition of Opponent II, ICOS Corp, to EP–B–0702555.
Pfizer's Combined Response.
Statement of Defense by Pfizer in the District Court of the Hague.
Transcript of Hearing on May 17, 2000.
Transcript of Hearing on May 26, 2000.
Transcript of Hearing on Jun. 22, 2000.
Transcript of Hearing on Jul. 19, 2000.
Judgment Given at Hearing on Aug. 17, 2000.
Paediatrics, Andrology, Infertility, Editorial Comment, by Ian Eardley, Department of Urology, Sep. 1993, Norfolk and Norwich Hospital, UK.
Paediatrics, Andrology, Infertility, Editorial Comment, by Ian Eardley, Department of Urology, Apr. 1993, Leeds General Infirmary, Leeds, UK.
Letters Discussing Repeats of Experiments.
Petitioner's Opening Submissions for Trial Before Laddie J.—Oct. 4, 2000.
Pfizer's Skeleton Argument.
Petitioner's Closing Submissions.
Closing Submissions of Pfizer.
Technical Primer from the High Court Proceedings.
Order of Mr. Justice Laddie—Dec. 5, 2000.
Appellant's Notice.
Appellant's Skeleton Argument.
Respondent's Skeleton Argument.
Transcript of Proceedings from Day One: Dec. 11, 2001.
Transcript of Proceedings from Day Two: Dec. 12, 2001.
Transcript of Proceedings from Day Three: Dec. 13, 2001.
Transcript of Proceedings from Day Four: Dec. 14, 2001.
Transcript of Proceedings from Day Five: Dec. 17, 2001.
UK Confidentiality Appeal Judgment.
UK Appeal Judgment.
Petition for Leave to Appeal.
Petition of Lilly Icos LLC, for Leave to Cross Appeal.
Pfizer's Reply to Statement of Argument (w/attachments).
Bayer's Statement of Argument (D1–16) (w/attachments).
Day Two Minuscript: Nov. 27, 2000.
Day Three Minuscript: Nov. 28, 2000.
Day Four Minuscript: Nov. 29, 2000.
Day Five Minuscript: Nov. 30, 2000.
Day Six Minuscript: Dec. 17, 2000.
Day Seven Minuscript: Dec. 18, 2000.
Day Eight Minuscript: Dec. 19, 2000.
Day Nine Minuscript: Jan. 17, 2001.
Opposition by Bayer to Pfizer's Patent Application No. 121836.
"Double Blind Trial of Oral Prostaglandin E1 on Impotence" (1992) (abstract submitted in English).
Second Declaration by Dr. Kenneth Murray Dated Apr. 9, 2001.
Pfizer's Exhibits Produced During Opening Speeches and Cross–Examination.
Bayer's Exhibits Produced During Opening Speeches and Cross–Examination (2 binders).
Pfizer's Response to Bayer's Reply to the Application to Amend the Claims (w/translation).
Decision Dated Dec. 21, 2001.
Opposition Statement by Opponent 1: Virus.
Proprietor's Submissions from May 16, 2001 onwards (Binder A, Tabs 1–4).
Opponents' Submissions from Apr. 6, 2001 onwards (Binder A, Tabs 5–20).
Written Submissions/Presentations Made During the Hearing from Jul. 16–18, 2001 (Binder A, Tabs 21–26).
Translation of Tab 10 from Binder A.
Translation of Tab 17 from Binder A.
Submissions to the EPO (S 14–15; S 17; S 19; S 20; S 35–36; S47–52).
References Filed wit the EPO: D 1–D85 (2 binders).
Documents Filed by the Proprietors: D 86–D 118 (Binder B).
Documents Filed with the EPO: D 119–D 140 (Binder C).
Documents Filed with the EPO: D 141–D 163 (Binder D).
Letter Dated Dec. 21, 2000 with Submissions to European Patent Office.
Letter Dated Dec. 20, 2000 to European Patent Office.
Dissertation of Margaret Bush (part of "BQ").
Witness Statement of Margaret Bush (part of "BQ").
Witness Statement of Julianna Jenkins (part of "BQ").
Judgment given by Justice Laddie in the Revocation Action Nov. 10, 2000 (part of "BQ").
Judgment of Invalidity Proceedings in the District Court of the Netherlands Oct. 4, 2001 (part of "BQ").
Reissue of Summons (Dec. 4, 2000).
Transcript of Ian Eardley Examined by Mr. Kitchell w/attachments.
Letter to EPO Filing Further Documents (Apr. 5, 2001) (w/documents).
Documents Being Submitted by Lilly in EPO Opposition (May 14, 2001).
Further Substantive Submissions (in German) (May 2, 2001) (w/translation).
Documents Filed with EPO by Opponent 2 (May 14, 2001).
Further Substantive Submissions by O–3 (May 14, 2001).
Further Substantive Submission by O–6 (May 2, 2001).
Letter from Opponent VII of May 16, 2000.
Further Substantive Submissions by O–9 (w/English Translation) (May 11, 2001).
Further Substantive Submissions by O–11 (May 16, 2001).
Further Substantive Submissions by O–10 (May 16, 2001).
Further Substantive Submissions by O–12 (May 16, 2001).
Letter to by O–2 (May 16, 2001).
Letter Enclosing Annex G by O–2 (May 16, 2001).
Letter to EPO by O–2 dated Jun. 14, 2001.
Letter to EPO by O–5 dated Jun. 15, 2001.
Letter to Patentee dated Jun. 14, 2001.
Further Substantive Submissions by O–8 (May 30, 2001).
Response to Opposition Preliminary Opinion by Patent Office (w/attachments) (May 16, 2001).
Written Decision to Revoke Patent by EPO (Oct. 11, 2001) (Adverse EPO decision).
Further Substantive Submissions on Behalf of O–2 and O–5 (Jul. 4, 2001).
Minutes of the Oral Proceedings before the Opposition Division (w/annexes) (Jul. 16, 2001).
11487 Appeal.
Notice of Opposition to EPO Patent (Vivus).
Notice of Opposition to EPO Patent (Merck) (w/translations).
Letter by Opponent Bayer (Mar. 30, 2001).
Pyrazolopyrimidinones for the Treatment of Impotence (submitted by Opponent II, ICOS Corp.).
Nullity Action and Restitution Against Resolution Nos. 0112 of Jan. 18, 2000 and 10169 of May 16, 2000.
Witness Statement of Peter Ellis.

Notice of Opposition (Lab. Rec.) Feb. 12, 1999 (w/translation).
Reply to Opposition Dec. 7, 1999.
Brief Requesting Urgent Prosecution of Appeal May 31, 2001.
Statement of Villouta.
Decision Dated Mar. 27, 2001.
European Heart Journal (1993, 14, (Supp. 1), pp. 141–148—Lugnier et al.
Science, vol. 257, Jul. 17, 1992, pp. 401–403—Burnett et al.
Impotence, 1995, vol. 22, No. 4, pp. 879–886—Morales et al.
Reason for Revocation.
Petition—Feb. 17, 1998.
Offer of Information with translations (4 references) (w/references).
Offer of Information with translations (7 references) (w/references).
International Journal of Impotence Research, Supplement 1, Sep. 1995.
Opposition (w/references) (w/translation).
English Translation of Argument Filed on Jan. 8, 1998.
Translation of the Petition Filed on Feb. 17, 1998.
Summary of Interview—Feb. 19, 2000.
Request for Correction—Feb. 19, 2001.
Response to Reasons for Revocation.
Offer of Information (12 references) (w/references).
Offer of Information (7 references) (w/references).
The Intellectual Property Tribunal 13th Panel—Trial Decision.
International Journal Impotence Research, 1995, pp. 13, by H. H. Knispel et al.
Psychosomatic Medicine, vol. 38, No. 6 (Nov.–Dec. 1976) pp. 418–425 by Leon A. Abramov.
Premenopausal Health Care, 20 (2), Jun. 1993 by Gloria A. Bachman, MD.
Clinics in Endocrinology and Metabolism (1982), 11(3), Nov., pp. 785–789, by John Bancroft.
Summary of KIPO Answer.
British Journal of Pharmacology (1998) 124, 000–000, Cellek et al.
Journal of Urology (1999), 161, pp. 940–944 by Tarcan et al.
Exp. Clin. Endocrinol. vol. 98, No. 2, 1991, pp. 61–69 by R. J. Levin.
Asia Pacific Journal of Pharmacology, 1991, pp. 213–227 by Adaikan et al.
Podium 18, "Alpha Blockade and Vaginal Blood Flow Response in Postmenopausal Women with Female Sexual Arousal Disorder" by Rubio et al. pp. 55 (2000).
Scrip's Complete Guide to Women's Health Care, 2000, Chapters 1–8.
J. Steroid Biochem. Molec. Biol. vol. 39, No. 6 pp. 873–881, 1991 by Williams–Ashman et al.
British Journal of Urology (1996), 78, 257–261 by Boolell et al.
The Journal of Urology (May 1996), vol. 155, No. 5, AUA Ninety–First Annual Meeting, 495A, 676A.
International Journal of Impotence Research (Jun. 1996), vol. 8, No. 2, pp. 47–52, Boolell et al.
The Journal of Urology (Apr. 1997), vol. 157, No. 4, Suppl. 1, and p. 204.
Rebuttal Brief by Appellant.
Rebuttal Brief by Plaintiff.
Declaration of Laurence Howard Skillern.
Appeal Brief.
Bayer: SCRAPS BAY 19–8004 for Asthma and COPD in P2–Jun. 14, 2001(vardenafil).
Witness Statement of Michael J. Allen (from Chinese Prosecution).
Witness Statement of Mitradev Boolell (from Chinese Prosecution).
Witness Statement of Nicholas Kenneth Terrett (co–inventor) (from Chinese Prosecution).
Declaration of Nicolas K. Terrett (co–inventor).
Witness Statement of Martyn Burslem.
Declaration of Stephen A. Ballard (in the Korean Industrial Property Office).
First Declaration of Stephen A. Ballard (in the U. S. Patent and Trademark Office).
Third Declaration of Stephen A. Ballard (in the USPTO).
Grounds for Rejection.
Female Sexual Dysfunction—Mosaic Study #16—Nov. 1999.
Proceedings of the American Urological Association, vol. 155, May 1996, Supplement 623A.
Declaration of Laurence Howard Skillern (w/attachments).
The Journal of Urology, 1989, vol. 141 pp. 546–548 by Owen et al.
Notice of Acceptance of Request for Invalidation Re: Patent Invention No. 94192386.X.
Response to the Notice of Acceptance of Request for Invalidation of the Above Patent Issued by the Patent Reexamination Board.
Response.
Request for Invalidation.
Ruling of Dutch Court: Nov. 11, 1999 (w/translation).
Writ of Summons in Accelerated Proceedings on the Merits (w/translation).
Statement of Claims with Exhibits (w/translation).
Letter of Feb. 22, 2000.
Statement of Defense, also Containing A Request for Suspension (w/translation).
Response to the Request for Adjournment (w/translation).
Letter of Mar. 27, 2000.
Letter of Mar. 28, 2000.
Letters dated Apr. 30, 2000 & Sep. 8, 1999.
Letter Dated Jun. 14, 2000 (including English Translation) with the New Notice of Experiments Attached.
Letter Dated Jun. 30, 2000 (w/English translation) with Additional Exhibits 1–5 Attached.
Letter of Jul. 3, 2000 (w/translation).
Oral Arguments on C.J.J.C. Van Nispen (w/translation).
Pleading Notes of Mr. L. Oosting (w/translation).
Statement Containing Submission of Exhibits (w/translation) with Exhibits.
Skeleton for the Hearing on Oral Arguments on Jul. 7, 2000 (w/translation).
Documents Containing Production of Exhibits, also Containing Skeleton Arguments (w/translation) & Letter of Jul. 7, 2000.
Decision of the District Court of Hague dated Oct. 4, 2000 (including English Translation).
Lepakhin Publication (1988) (w/excerpt translated).
Title Page of the Braunwald Publication (w/excerpt translated).
28th British Congress of Obstetrics and Gynaecology Abstract Status Report (1998), No. 7085.

World Foundation for Medical Studies in Female Health, (1999), Abstract Status Report, Nos. 7214, 7215.

Radiology 2000, 214(2):611.

Pilot Study on the Effectiveness of Viagra for Treatment of Female Sexual Dysfunction: Physiologic Predictor for Success (2000), Chai et al.

American College of Obstetrics and Gynecologists (ACOG) 48th Annual Clinical Meeting: Abstract Status Report (May 20–24, 2000), No. 7217.

FIGO World Congress of Gynecology and Obstetrics (2000), Abstract Status Report, Nos. 7279, 7280 & 7281.

Efficacy and Safety of Viagra (sildenafil citrate) in Non--Oestrogenised Women with Sexual Dysfunction Associated with FSAD (2000).

"What About the Female Partner's Quality of Life in ED?" (2000), Chevret–Measson et al.

Urology 54 (1999): 385–391 by Berman et al.

Efficacy and Safety of Viagra (sildenafil citrate) in Estrogenised Women with Sexual Dysfunction Associated with FSAD.

A Pilot Study of the Effect of Viagra (sildenafil citrate) on Vaginal Blood Flow in Female Subjects (2000).

Journal of Sex & Marital Therapy, 26: 191–208 (2000).

European Journal of Pharmacology 400(2000) 305–312, Frith et al.

Vaginal Sildenafil: A Preliminary Report of a Novel Method to Improve Uterine Artery Blood Flow and Endometrial Development in Patients Undergoing in Vitro Fertilization, Sher et al.

Urology 55(6) 812–815 (2000), Sipski et al.

The Journal of Reproductive Medicine, 44(6) 535–542 (Jun. 1999).

British Journal of Obstetrics & Gynaecology, Jun. 2001, vol. 108, pp. 623–628.

Effect of Vasoactive Agents in Modulating Vaginal Smooth Muscle Contractility: Implications for Treatment of Female Sexual Dysfunction (2000), Berman et al.

Observations After Viagra: Study on "Estrogenized" Women is Released (2000), Berman et al.

J. of Steroid Biochemistry & Molecular Biology 69 (1999) 177–184, S.R. Davis.

Current Opinion in Neurobiology (1999) 9: 751–758, Pfaus.

Women are Eager to Participate in the Viagra Revolution by Lan N. Nguyen.

Doctors Find Viagra Works Just as Well in Women (The Sunday Telegraph—UK).

Viagra Fails in Female Study ( Scrip Daily News) (May 31, 2000).

Viagra Fails Test to Help Women by Phil Galewitz, AP Business Writer.

Positive Effects of Sildenafil in Female Sexual Dysfunction Following Hysterectomy (2000).

SCRIP Daily News (Apr. 25, 2000).

Women Could Get Viagra in 3 Years by Helen Rumbelow, The Times, Oct. 27, 1999.

Viagra Doesn't Work in Women (SCRIP No. 2419, Mar. 12th 1999, p 23).

Why Viagra Doesn't Work for Women by James Le Fanu, The Daily Telegraph.

Viagra Priapism ( SCRIP No. 2387 Nov. 13th 1998 p 12).

SCRIP No. 2369 Sep. 11th 1998 p 22.

Cialis's Unfavorable Results in Female Sexual Dysfunction ( SG Cowen Securities/Scala, Jun. 18, 2001).

Cialis (SD) Launch '02E, Pk sales Est $1B, 30% SOM '07E (Jan. 9, 2001).

The Orgasm Pill: Are You Ready for It? By Erin Kelly, Cosmopolitan.

Progress with Viagra for FSD (Scrip daily News) Mar. 15, 2000.

The Second Sexual Revolution by Jack Hitt, NY Times Magazine, (Feb. 20, 2000).

Anti–Impotence Drug by Debra McGarry, CBS Market Watch (Jan. 12, 2000).

The Berman Sisters, Pioneers in the Study of Women's Sexual Dysfunction (LA Times) (Feb. 12, 2001).

Female Sexual Dysfunction by Cheryl Terhorst (Apr. 18, 2001).

Scrip's Complete Guide to Women's Healthcare: Female Sexual Dysfunction (Chapter 7) (2000).

"Stop Fancying Each Other", News Paper Article.

J. Berman's Poster at 1999 AUA Conference.

J. of Sexual & Marital Therapy, 27:411–420, 2001, Berman et al.

Int J Impot Res Apr. 2000;12(Supp 2):S17.

J Urol. 2001, May; 165(5) Supplement: P227 (#935).

15th World Congress of Sexology. Jun. 24, 2001, M. A. Perelman, Abstract Book:181.

15th World Congress of Sexology. Jun. 24, 2001; Van Lunsen Abstract Book:240.

Fertil Steril. Sep. 2001; 76(3 Suppl 1): S255 (#P–430).

Urology 1999; 53 (3): 481–486, Kaplan et al.

Mol Cell Biol Res Commun (1999) 2(2): 131–137, Traish et al.

J Sex Marital Ther (2000) Apr.–Jun.; 26:133–140.

Br J Obstet Gynaecol. Jun. 2001; 108:Editor's Choice Introduction.

J Sex Marital Ther. 2001; 27:411–420, Berman et al.

J Sex Marital Ther. 2001: 27:427–433, Berman et al.

J Sex Martial Ther. Oct. 2001; 27(5):421–425, Berman et al.

Int J Impot Res (2000); 12 Supp 4:S152–S157, Goldstein.

Int J Impot Res (2000); 12 Supp 3:S32–S39, Min et al.

Psychiatric Services; Aug. 1999; 50(8):1076–1078.

Am J Psychiatry; Oct. 1999; 156(10):1664.

International Journal of Impotence Research, Supp 12: S32–S39, Min et al.

Curr Psychiatry Rep. 2001 (3): 188–194, Shabsigh.

J Sex Res. 2001; 38(2): 89–96.

Hysterectomy & Sexual Dysfunction: Effects of Sildenafil in a Clinical Setting (May 2, 2000), Berman et al.

Pfizer Statement on Salvatore Caruso's Study (May 21, 2001).

New Scientist, Mar. 1999, p. 15.

Thesis Statement of Margaret Ann Bush, PhD.

BR. J. Pharmocol. (1993) 108, 562–568.

Journal of Urology 150: 1310–1315 (Oct. 1993), Holmquist.

International Journal of Impotence Research, 4 (Suppl. 2) (1992) p. 19.

Journal of Ethnopharmacology, 12 (1984) 35–74.

Nicholson et al., TIPS, Jan. 1991, vol. 12, pp. 19–27.

Journal of Urology 149:285A (Apr. 1993).

Brit. J. Urology, 71: 365 (Mar. 1993).

Post Graduate Medicine 88(2) (1990) 139–152, Whitehead, et al.

"Chemical A Factor in Male Impotence", Jan. 9, 1992, NY Times, D. Blakeslee.

The Journal of Urology, vol. 151, No. 5, p. 495A, 1994.

Pharmacological Reviews 43(2) (1991) pp. 109–142, Moncada et al.
Declaration of Ian Eardley (w/Annexes).
Declaration of R.A. John Chaliss (w/Annexes).
Declaration of Peter Ellis (with References).
Declaration of Steven Ballard.
Declaration of David Goren (with Appendixes).
Declaration of Louis J. Ignarro (with References).
Declaration of Dr. Inigo Saenz de Tejada.
Declaration of Clive Page.
Declaration of Ken Murray (w/exhibits).
Bayer 1.
Bayer 2.
Affidavit of Dr. Yaakov Ramon (unsigned).
Bayer Opposition Statement (with Exhibits).
Argument Papers from Dutch Revocation Proceeding.
Slides.
Excerpts from the UCLA doctoral dissertation of Margaret Ann Bush, including pp. ii–Xvii, 1 and 154–161, 1993.
Experimental Report to Israeli Opposition Statement.
Israeli Opposition Statement of Bayer Aktiengesellschaft.
Karl–Erik Anderson et al. The American Physiological Society, 1995, vol. 75, pp. 191–236.

W. Meinhardt et al., International Journal of Impotence Research, 1997, vol. 9, pp. 17–26.
F. Holmquist et al., Arta Physiol Scand, 1991, vol. 143, pp. 299–304.
M. F. Meyer et al., Ann Urol., 1993, vol. 27, No. 3, pp. 179–182.
Y.–M. Lin et al., Urol. Res, 1990, vol. 24, pp. 27–32.
Harvey C. Taub, et al., Urology, 1993, vol. 42, No. 6, pp. 698–704.
Int. J. Impotence Res. (1992) 4, Suppl. 2 p. 11, Taher et al.
Murray, Kenneth J., Drug News & Perspectives, 6, 150–156 (1993).
Mirone, V., et al., British J. of Urology, 71, 3, 365 (1993).
Bush, Peggy A., et al., J. of Urology, 147, 1650–1655 (1992).
Rajfer, Jacob, et al., New England Journal of Medicine, 326, 2, 90–94 (1992).
Bowman, Anne et al., British J. Pharmac., 81, 665–674 (1984).
Trigo–Rocha, Flavio, et al., Am. Physiological Society, 264, H419–H422 (1993).

* cited by examiner

PYRAZOLOPYRIMIDINONES FOR THE TREATMENT OF IMPOTENCE

This is a National Phase filing under 35 USC §371 based on PCT/EP94/01580, which was filed internationally on May 13, 1994.

This invention relates to the use of a series of pyrazolo [4,3-d]pyrimidin-7-ones for the treatment of impotence.

Impotence can be defined literally as a lack of power, in the male, to copulate and may involve an inability to achieve penile erection or ejaculation, or both. More specifically, erectile impotence or dysfunction may be defined as an inability to obtain or sustain an erection adequate for intercourse. Its prevalence is claimed to be between 2 and 7% of the human male population, increasing with age, up to 50 years, and between 18 and 75% between 55 and 80 years of age. In the USA alone, for example, it has been estimated that there are up to 10 million impotent males, with the majority suffering from problems of organic rather than of psychogenic origin.

Reports of well-controlled clinical trials in man are few and the efficacy of orally administered drugs is low. Although many different drugs have been shown to induce penile erection, they are only effective after direct injection into the penis, e.g. intraurethrally or intracavernosally (i.c.), and are not approved for erectile dysfunction. Current medical treatment is based on the i.c injection of vasoactive substances and good results have been claimed with phenoxybenzamine, phentolamine, papaverine and prostaglandin $E_1$, either alone or in combination; however, pain, priapism and fibrosis of the penis are associated with the i.c. administration of some of these agents. Potassium channel openers (KCO) and vasoactive intestinal polypeptide (VIP) have also been shown to be active i.c., but cost and stability issues could limit development of the latter. An alternative to the i.c. route is the use of glyceryl trinitrate (GTN) patches applied to the penis, which has been shown to be effective but produces side-effects in both patient and partner.

As a general alternative to pharmacological intervention, a variety of penile prostheses has been used to assist achievement of an erection. The short term success rate is good, but problems with infection and ischaemia, especially in diabetic men, make this type of treatment a final option rather than first-line therapy.

The compounds of the invention are potent inhibitors of cyclic guanosine 3′,5′-monophosphate phosphodiesterases (cGMP PDEs) in contrast to their inhibition of cyclic adenosine 3′,5′-monophosphate phosphodiesterases (cAMP PDEs). This selective enzyme inhibition leads to elevated cGMP levels which, in turn, provides the basis for the utilities already disclosed for the said compounds in EP-A-0463756 and EP-A-0526004, namely in the treatment of stable, unstable and variant (Prinzmetal) angina, hypertension, pulmonary hypertension, congestive heart failure, atherosclerosis, conditions of reduced blood vessel patency e.g. post-percutaneous transluminal coronary angioplasty (post-PTCA), peripheral vascular disease, stroke, bronchitis, allergic asthma, chronic asthma, allergic rhinitis, glaucoma, and diseases characterised by disorders of gut motility, e.g. irritable bowel syndrome (IBS).

Unexpectedly, it has now been found that these disclosed compounds are useful in the treatment of erectile dysfunction. Furthermore the compounds may be administered orally, thereby obviating the disadvantages associated with i.c. administration. Thus the present invention concerns the use of a compound of formula (I):

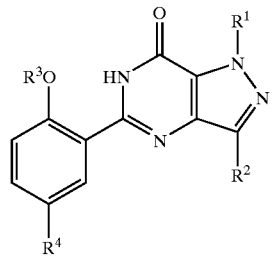

wherein $R^1$ is H; $C_1$–$C_3$ alkyl; $C_1$–$C_3$ perfluoroalkyl; or $C_3$–$C_5$ cycloalkyl;

$R^2$ is H; $C_1$–$C_6$ alkyl optionally substituted with $C_3$–$C_6$ cycloalkyl; $C_1$–$C_3$ perfluoroalkyl; or $C_3$–$C_6$ cycloalkyl;

$R^3$ is $C_1$–$C_6$ alkyl optionally substituted with $C_3$–$C_6$ cycloalkyl; $C_1$–$C_6$ perfluoroalkyl; $C_3$–$C_5$ cycloalkyl; $C_3$–$C_6$ alkenyl; or $C_3$–$C_6$ alkynyl;

$R^4$ is $C_1$–$C_4$ alkyl optionally substituted with OH, $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; (hydroxy)$C_2$–$C_4$ alkyl optionally substituted with $NR^5R^6$; ($C_2$–$C_3$ alkoxy)$C_1$–$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; $SO_2NR^9R^{10}$; or phenyl, pyridyl, pyrimidinyl, imidazolyl, oxazolyl, thiazolyl, thienyl or triazolyl any of which is optionally substituted with methyl;

$R^5$ and $R^6$ are each independently H or $C_1$–$C_4$ alkyl, or together with the nitrogen atom to which they are attached form a pyrrolidinyl, piperidino, morpholino, 4-N($R^{11}$)-piperazinyl or imidazolyl group wherein said group is optionally substituted with methyl or OH;

$R^7$ is H or $C_1$–$C_4$ alkyl;

$R^8$ is $C_1$–$C_3$ alkyl optionally substituted with $NR^5R^6$;

$R^9$ and $R^{10}$ together with the nitrogen atom to which they are attached form a pyrrolidinyl, piperidino, morpholino or 4-N($R^{12}$)-piperazinyl group wherein said group is optionally substituted with $C_1$–$C_4$ alkyl, $C_1$–$C_3$ alkoxy, $NR^{13}R^{14}$ or $CONR^{13}R^{14}$;

$R^{11}$ is H; $C_1$–$C_3$ alkyl optionally substituted with phenyl; (hydroxy)$C_2$–$C_3$ alkyl; or $C_1$–$C_4$ alkanoyl;

$R^{12}$ is H; $C_1$–$C_6$ alkyl; ($C_1$–$C_3$ alkoxy)$C_2$–$C_6$ alkyl; (hydroxy)$C_2$–$C_6$ alkyl; ($R^{13}R^{14}N$)$C_2$–$C_6$ alkyl; ($R^{13}R^{14}NOC$)$C_1$–$C_6$ alkyl; $CONR^{13}R^{14}$; $CSNR^{13}R^{14}$; or $C(NH)NR^{13}R^{14}$; and $R^{13}$ and $R^{14}$ are each independently H; $C_1$–$C_4$ alkyl; ($C_1$–$C_3$ alkoxy)$C_2$–$C_4$ alkyl; or (hydroxy)$C_2$–$C_4$ alkyl;

or a pharmaceutically acceptable salt thereof, or a pharmaceutical composition containing either entity, for the manufacture of a medicament for the curative or prophylactic treatment of erectile dysfunction in a male animal, including man.

In the above definition, unless otherwise indicated, alkyl groups having three or more carbon atoms, alkenyl and alkynyl groups having four or more carbon atoms, alkoxy groups having three carbon atoms and alkanoyl groups having four carbon atoms may be straight chain or branched chain. Halo means fluoro, chloro, bromo or iodo.

The compounds of formula (I) may contain one or more asymmetric centres and thus they can exist as enantiomers or diastereoisomers. Furthermore, certain compounds of formula (I) which contain alkenyl groups may exist as cis-isomers or trans-isomers. In each instance, the invention includes both mixtures and separate individual isomers.

The compounds of formula (I) may also exist in tautomeric forms and the invention includes both mixtures and separate individual tautomers.

The pharmaceutically acceptable salts of the compounds of formula (I) which contain a basic centre are, for example, non-toxic acid addition salts formed with inorganic acids such as hydrochloric, hydrobromic, sulphuric and phosphoric acid, with organo-carboxylic acids, or with organo-sulphonic acids. Compounds of formula (I) can also provide pharmaceutically acceptable metal salts, in particular non-toxic alkali metal salts, with bases. Examples include the sodium and potassium salts.

A preferred group of compounds of formula (I) is that wherein $R^1$ is H, methyl or ethyl; $R^2$ is $C_1$–$C_3$ alkyl; $R^3$ is $C_2$–$C_3$ alkyl or allyl; $R^4$ is $C_1$–$C_2$ alkyl optionally substituted with OH, $NR^5R^6$, CN, $CONR^5R^6$ or $CO_2R^7$; acetyl optionally substituted with $NR^5R^6$; hydroxyethyl optionally substituted with $NR^5R^6$; ethoxymethyl optionally substituted with OH or $NR^5R^6$; CH=CHCN; CH=CHCONR$^5$R$^6$; CH=CHCO$_2$R$^7$; CONR$^5$R$^6$; CO$_2$H; Br; $NR^5R^6$; $NHSO_2NR^5R^6$; $NHSO_2R^8$; $SO_2NR^9R^{10}$; or pyridyl or imidazolyl either of which is optionally substituted with methyl; $R^5$ and $R^6$ are each independently H, methyl or ethyl, or together with the nitrogen atom to which they are attached form a piperidino, morpholino, 4-N($R^{11}$)-piperazinyl or imidazolyl group wherein said group is optionally substituted with methyl or OH; $R^7$ is H or t-butyl; $R^8$ is methyl or $CH_2CH_2CH_2NR^5R^6$; $R^9$ and $R^{10}$ together with the nitrogen atom to which they are attached form a piperidino or 4-N($R^{12}$)-piperazinyl group wherein said group is optionally substituted with $NR^{13}R^{14}$ or $CONR^{13}R^{14}$; $R^{11}$ is H, methyl, benzyl, 2-hydroxyethyl or acetyl; $R^{12}$ is H, $C_1$–$C_3$ alkyl, (hydroxy)$C_2$–$C_3$ alkyl, $CSNR^{13}R^{14}$ or $C(NH)NR^{13}R^{14}$; and $R^{13}$ and $R^{14}$ are each independently H or methyl.

A more preferred group of compounds of formula (I) is that wherein $R^1$ is methyl or ethyl; $R^2$ is $C_1$–$C_3$ alkyl; $R^3$ is ethyl, n-propyl or allyl; $R^4$ is $CH_2NR^5R^6$, $COCH_2NR^5R^6$, $CH(OH)CH_2NR^5R^6$, $CH_2OCH_2CH_3$, $CH_2OCH_2CH_2OH$, $CH_2OCH_2CH_2NR^5R^6$, CH=CHCON(CH$_3$)$_2$, CH=CHCO$_2$R$^7$, CONR$^5$R$_6$, CO$_2$H, Br, NHSO$_2$NR$^5$R$^6$, NHSO$_2$CH$_2$CH$_2$CH$_2$NR$^5$R$^6$, SO$_2$NR$^9$R$^{10}$, 2-pyridyl, 1-imidazolyl or 1-methyl-2-imidazolyl; $R^5$ and $R^6$ together with the nitrogen atom to which they are attached form a piperidino, 4-hydroxypiperidino, morpholino, 4-N($R^{11}$)-piperazinyl or 2-methyl-1-imidazolyl group; $R^7$ is H or t-butyl; $R^9$ and $R^{10}$ together with the nitrogen atom to which they are attached form a 4-carbamoylpiperidino or 4-N($R^{12}$)-piperazinyl group; $R^{11}$ is H, methyl, benzyl, 2-hydroxyethyl or acetyl; and $R^{12}$ is H, $C_1$–$C_3$ alkyl, 2-hydroxyethyl or $CSNH_2$.

A particularly preferred group of compounds of formula (I) is that wherein $R^1$ is methyl or ethyl; $R^2$ is n-propyl; $R^3$ is ethyl, n-propyl or allyl; $R^4$ is $COCH_2NR^5R^6$, $CONR^5R^6$, $SO_2NR^9R^{10}$ or 1-methyl-2-imidazolyl; $R^5$ and $R^6$ together with the nitrogen atom to which they are attached form a morpholino or 4-N($R^{11}$)-piperazinyl group; $R^9$ and $R_{10}$ together with the nitrogen atom to which they are attached form a 4-N($R^{12}$)-piperazinyl group; $R^{11}$ is methyl or acetyl; and $R^{12}$ is H, methyl, 2-propyl or 2-hydroxyethyl.

Especially preferred individual compounds of the invention include:

5-(2-ethoxy-5-morpholinoacetylphenyl)-1-methyl-3-n-propyl-1, 6-dihydro-7H-pyrazolo[4,3-d]pyrimidin-7-one;

5-(5-morpholinoacetyl-2-n-propoxyphenyl)-1-methyl-3-n-propyl-1, 6-dihydro-7H-pyrazolo[4,3-d]pyrimidin-7-one;

5-[2-ethoxy-5-(4-methyl-1-piperazinylsulphonyl)-phenyl]-1-methyl-3-n-propyl-1,6-dihydro-7H-pyrazolo[4,3-d]pyrimidin-7-one;

5-[2-allyloxy-5-(4-methyl-1-piperazinylsulphonyl)-phenyl]-1-methyl-3-n-propyl-1,6-dihydro-7H-pyrazolo[4,3-d]pyrimidin-7-one;

5-{2-ethoxy-5-[4-(2-propyl)-1-piperazinyl-sulphonyl]phenyl}-1-methyl-3-n-propyl-1,6-dihydro-7H-pyrazolo[4,3-d]pyrimidin-7-one;

5-{2-ethoxy-5-[4-(2-hydroxyethyl)-1-piperazinyl-sulphonyl]phenyl}-1-methyl-3-n-propyl-1,6-dihydro-7H-pyrazolo[4,3-d]pyrimidin-7-one;

5-{5-[4-(2-hydroxyethyl)-1-piperazinylsulphonyl]-2-n-propoxyphenyl}-1-methyl-3-n-propyl-1,6-dihydro-7H-pyrazolo[4,3-d]pyrimidin-7-one;

5-[2-ethoxy-5-(4-methyl-1-piperazinylcarbonyl)-phenyl]-1-methyl-3-n-propyl-1,6-dihydro-7H-pyrazolo[4,3-d] pyrimidin-7-one; and 5-[2-ethoxy-5-(1-methyl-2-imidazolyl)phenyl]-1-methyl-3-n-propyl-1,6-dihydro-7H-pyrazolo[4,3-d]pyrimidin-7-one.

The compounds of formula (I) and their pharmaceutically acceptable salts, processes for the preparation thereof, in vitro test methods for determining the cGMP PDE and cAMP PDE inhibitory activities thereof, pharmaceutical compositions thereof and routes of administration for human use, are described in EP-A-0463756 and EP-A-0526004.

A preliminary investigation was carried out with a view to isolating and characterising the cyclic nucleotide PDEs of human corpus cavernosum, relaxation of which leads to penile erection. Studies of substrate specificity, response to activators and inhibitor sensitivity, have demonstrated that human corpus cavernosum contains three distinct PDE enzymes.

METHODS

Fresh frozen human penis was obtained from IIAM (Pennsylvania). Tissue was thawed at room temperature, the corpus cavernosum was dissected from the penis to yield approximately 2–4 g of tissue and the following isolation protocol was followed. Tissue was coarsely chopped in ice-cold isotonic buffer (35 ml) containing 250 mM sucrose, 1 mM EDTA, 0.5 mM PMSF and 20 mM HEPES, pH 7.2, and the mixture subjected to brief (1 min.) treatment with a Silversen mixer/emulsifier. Homogenates were prepared using homogeniser tubes with teflon pestles and soluble fraction was prepared by centrifugation at 100,000×g for 60 min. at 4° C. 10 ml of high speed supernatant was applied to a Pharmacia Mono Q anion exchange column (1 ml bed volume) equilibrated with buffer containing 1 mM EDTA, 0.5 mM PMSF and 20 mM 1hEPES, pH 7.2 (chromatography buffer). The column was then washed with 5 bed volumes of chromatography buffer, after which PDEs were eluted using a continuous gradient of 0–500 mM NaCl (total volume 35 ml) and 1 ml fractions collected.

Column fractions were assayed for PDE activity using 500 nM cGMP or 500 nM cAMP as substrate. cAMP PDE activity was also determined in the presence of 1 $\mu$M unlabelled cGMP and the PDE activity of selected fractions was determined in the presence of 10 mM $CaCl_2$ and 10 units/ml bovine brain calmodulin. Appropriate fractions were pooled and stored at 4° C. during the course of the study.

Inhibition studies were performed using a substrate concentration of 500 nM throughout. All inhibitors were dissolved in DMSO and concentration-response curves were constructed over the range $3 \times 10^{-10}$ to $1 \times 10^{-4}$ M in half log increments. $IC_{50}$ values were calculated using the sigmoidal curve fitting algorithm of biostat.

RESULTS

Human corpus cavernosum soluble PDEs were separated into three distinct fractions of activity. The first, fraction I, (designated by order of elution) represents the major PDE present and is highly selective for cGMP as substrate. This fraction was found to be insensitive to stimulation by calcium/calmodulin and was classified as $PDE_V$. Fraction II hydrolyses cGMP and cAMP, with the latter activity being stimulated in the presence of cGMP, and is classified as $PDE_{II}$, whilst fraction III is cAMP selective and this activity is inhibited in the presence of cGMP, consistent with $PDE_{III}$ activity.

In order to further characterise the PDE isoenzymes present in the tissue, studies were performed using a variety of inhibitors. Inhibitor studies with fractions I and II were performed using cGMP as substrate, whilst fraction III studies utilised cAMP. These studies confirmed that fraction I corresponds to $PDE_V$, whilst fraction III was clearly identified as $PDE_{III}$; fraction II ($PDE_{II}$) was relatively insensitive to all the inhibitors tested.

In summary, the above investigation identified three PDE isoenzymes in human corpus cavernosum tissue. The predominant PDE is the cGMP-specific $PDE_V$, whilst cGMP-stimulated cAMP $PDE_{II}$ and cGMP-inhibited cAMP $PDE_{III}$ are also present.

The compounds of the invention have been tested in vitro and found to be potent and selective inhibitors of the cGMP-specific $PDE_V$. For example, one of the especially preferred compounds of the invention has an $IC_{50}=6.8$ nM v. the $PDE_V$ enzyme, but demonstrates only weak inhibitory activity against the $PDE_{II}$ and $PDE_{III}$ enzymes with $IC_{50}=$ >100 $\mu$M and 34 $\mu$M respectively. Thus relaxation of the corpus cavernosum tissue and consequent penile erection is presumably mediated by elevation of cGMP levels in the said tissue, by virtue of the PDE inhibitory profile of the compounds of the invention.

Furthermore, none of the compounds of the invention tested in rat and dog, both intravenously (i.v.) and orally (p.o.) at up to 3 mg/Kg, has shown any overt sign of adverse acute toxicity. In mouse, no deaths occurred after doses of up to 100 mg/Kg i.v. Certain especially preferred compounds showed no toxic effects on chronic p.o. administration to rat at up to 10 mg/Kg and to dog at up to 20 mg/Kg.

In man, certain especially preferred compounds have been tested orally in both single dose and multiple dose volunteer studies. Moreover, patient studies conducted thus far have confirmed that one of the especially preferred compounds induces penile erection in impotent males.

Although the compounds of the invention are envisaged primarily for the treatment of erectile dysfunction or sexual dysfunction, they may also be useful for the treatment of female sexual dysfunction including orgasmic dysfunction related to clitoral disturbances.

Generally, in man, oral administration of the compounds of the invention is the preferred route, being the most convenient and avoiding the disadvantages associated with i.c. administration. A preferred dosing regimen for a typical man is 5 to 75 mg of compound three times daily. In circumstances where the recipient suffers from a swallowing disorder or from impairment of drug absorption after oral administration, the drug may be administered parenterally, e.g. sublingually or buccally.

For veterinary use, a compound of formula (I) or a non-toxic salt thereof is administered as a suitably acceptable formulation in accordance with normal veterinary practice and the veterinary surgeon will determine the dosing regimen and route of administration which will be most appropriate for a particular male animal.

Thus the invention includes a pharmaceutical composition for the curative or prophylactic treatment of erectile dysfunction in a male animal, including man, comprising a compound of formula (I), or a pharmaceutically acceptable salt thereof, together with a pharmaceutically acceptable diluent or carrier.

There is further provided a process for the preparation of a pharmaceutical composition for the curative or prophylactic treatment of erectile dysfunction in a male animal, including man, comprising formulating a compound of formula (I), or a pharmaceutically acceptable salt thereof, with a pharmaceutically acceptable diluent or carrier.

The invention also provides a method of treating a male animal, including man, to cure or prevent erectile dysfunction which comprises treating said male animal with an effective amount of a compound of formula (I), or a pharmaceutically acceptable salt thereof, or a pharmaceutical composition containing either entity.

In a further aspect, the invention includes the use of a cGMP PDE inhibitor, or a pharmaceutically acceptable salt thereof, or a pharmaceutical composition containing either entity, for the oral treatment of erectile dysfunction in man.

The invention also includes a method of orally treating man to cure or prevent erectile dysfunction, which comprises treatment with an orally effective amount of a cGMP PDE inhibitor, or a pharmaceutically acceptable salt thereof, or a pharmaceutical composition containing either entity.

Moreover, the invention includes the use of a cGMP PDE inhibitor, or a pharmaceutically acceptable salt thereof, or a pharmaceutical composition containing either entity, for the manufacture of a medicament for the curative or prophylactic oral treatment of erectile dysfunction in man.

What is claimed is:

1. A method of treating erectile dysfunction in a male animal, comprising administering to a male animal in need of such treatment an effective amount of a compound of formula (I):

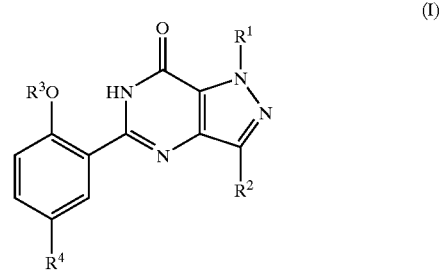

wherein:
$R^1$ is H; $C_1$–$C_3$ alkyl; $C_1$–$C_3$ perfluoroalkyl; or $C_3$–$C_5$ cycloalkyl;
$R^2$ is H; $C_1$–$C_6$ alkyl optionally substituted with $C_3$–$C_6$ cycloalkyl; $C_1$–$C_3$ perfluoroalkyl; or $C_3$–$C_6$ cycloalkyl;
$R^3$ is $C_1$–$C_6$ alkyl optionally substituted with $C_3$–$C_6$ cycloalkyl; $C_1$–$C_6$ perfluoroalkyl; $C_3$–$C_5$ cycloalkyl; $C_3$–$C_6$ alkenyl; or $C_3$–$C_6$ alkynyl;

$R^4$ is $C_1$–$C_4$ alkyl optionally substituted with OH, $NR^5R^6$, CN, $CONR^5R^6$ or $CO_2R^7$; $C_2$–$C_4$ alkenyl optionally substituted with CN, $CONR_5R^6$ or $CO_2R^7$; $C_2$–$C_4$ alkanoyl optionally substituted with $NR^5R^6$; (hydroxy)$C_2$–$C_4$ alkyl optionally substituted with $NR^5R^6$; ($C_2$–$C_3$ alkoxy)$C_1$–$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; $SO_2NR^9R^{10}$; or phenyl pyridyl, pyrimidinyl, imidazolyl, oxazolyl, thiazolyl, thienyl or triazolyl any of which is optionally substituted with methyl;

$R^5$ and $R^6$ are each independently H or $C_1$–$C_4$ alkyl, or together with the nitrogen atom to which they are attached form a pyrrolidinyl, piperidino, morpholino, 4-N($R^{11}$)-piperazinyl or imidazolyl group wherein said group is optionally substituted with methyl or OH;

$R^7$ is H or $C_1$–$C_4$ alkyl;

$R^8$ is $C_1$–$C_3$ alkyl optionally substituted with $NR^5R^6$;

$R^9$ and $R^{10}$ together with the nitrogen atom to which they are attached form a pyrrolidinyl, piperidino, morpholino or 4-N($R^{12}$)-piperazinyl group wherein said group is optionally substituted with $C_1$–$C_4$ alkyl, $C_1$–$C_3$ alkoxy, $NR^{13}R^{14}$ or $CONR^{13}R^{14}$;

$R^{11}$ is H; $C_1$–$C_3$ alkyl optionally substituted with phenyl; (hydroxy)$C_2$–$C_3$ alkyl; or $C_1$–$C_4$ alkanoyl;

$R^{12}$ is H; $C_1$–$C_6$ alkyl; ($C_1$–$C_3$ alkoxy)$C_2$–$C_6$ alkyl; (hydroxy)$C_2$–$C_6$ alkyl; ($R^{13}R^{14}$N)$C_2$–$C_6$ alkyl; ($R^{13}R^{14}$NOC)$C_1$–$C_6$ alkyl; $CONR^{13}R^{14}$; $CSNR^{13}R^{14}$; or $C(NH)NR^{13}R^{14}$; and $R^{13}$ and $R^{14}$ are each independently H; $C_1$–$C_4$ alkyl; ($C_1$–$C_3$ alkoxy)$C_2$–$C_4$ alkyl; or (hydroxy)$C_2$–$C_4$ alkyl; or a pharmaceutically acceptable salt thereof; or a pharmaceutically acceptable composition containing either entity.

2. A method as defined in claim 1, wherein said treatment is veterinary treatment.

3. A method as defined in claim 1, wherein said compound is 5-(2-ethoxy-5-morpholinoacetylphenyl)-1-methyl-3-n-propyl-1,6-dihydro-7H-pyrazolo[4,3-d]pyrimidin-7-one.

4. A method as defined in claim 1, wherein said compound is 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one.

5. A method as defined in claim 1, wherein said compound, salt or composition is administered orally, intravenously, sublingually, or buccally.

6. A method as defined in claim 1, wherein said compound, salt or composition is administered orally.

7. A method as defined in claim 6 wherein in the compound of formula (I) $R^1$ is H, methyl or ethyl; $R^2$ is $C_1$–$C_3$ alkyl; $R^3$ is $C_2$–$C_3$ alkyl or allyl; $R^4$ is $C_1$–$C_2$ alkyl optionally substituted with OH, $NR^5R^6$, CN, $CONR^5R^6$ or $CO_2R^7$; acetyl optionally substituted with $NR^5R^6$; hydroxyethyl optionally substituted with $NR^5R^6$; ethoxymethyl optionally substituted with OH or $NR^5R^6$; CH=CHCN; CH=CHCONR$^5$R$^6$; CH=CHCO$_2$R$^7$; CONR$^5$R$^6$; CO$_2$H; Br; NR$^5$R$^6$; NHSO$_2$NR$^5$R$^6$; NHSO$_2$R$^8$; SO$_2$NR$^9$R$^{10}$; or pyridyl or imidazolyl either of which is optionally substituted with methyl; $R^5$ and $R^6$ are each independently H, methyl or ethyl, or together with the nitrogen atom to which they are attached form a piperidino, morpholino, 4-N($R^{11}$)-piperazinyl or imidazolyl group wherein said group is optionally substituted with methyl or OH; $R^7$ is H or t-butyl; $R^8$ is methyl or $CH_2CH_2CH_2NR^5R^6$; $R^9$ and $R^{10}$ together with the nitrogen atom to which they are attached form a piperidino or 4-N($R^{12}$)-piperazinyl group wherein said group is optionally substituted with $NR^{13}R^{14}$ or $CONR^{13}R^{14}$; $R^{11}$ is H, methyl, benzyl, 2-hydroxyethyl or acetyl; $R^{12}$ is H, $C_1$–$C_3$ alkyl, (hydroxy)$C_2$–$C_3$ alkyl, $CSNR^{13}R^{14}$ or $C(NH)NR^{13}R^{14}$; and $R^{13}$ and $R^{14}$ are each independently H or methyl.

8. A method as defined in claim 7 wherein in the compound of formula (I) $R^1$ is methyl or ethyl; $R^2$ is $C_1$–$C_3$ alkyl; $R^3$ is ethyl, n-propyl or allyl; $R^4$ is $CH_2NR^5R^6$, $COCH_2NR^5R^6$, $CH(OH)CH_2NR^5R^6$, $CH_2OCH_2CH_3$, $CH_2OCH_2CH_2OH$, $CH_2OCH_2CH_2NR^5R^6$, CH=CHCON$(CH_3)_2$, CH=CHCO$_2$R$^7$, CONR$^5$R$^6$, CO$_2$H, Br, NHSO$_2$NR$^5$R$^6$, NHSO$_2$CH$_2$CH$_2$CH$_2$NR$^5$R$^6$, SO$_2$NR$^9$R$^{10}$, 2-pyridyl, 1-imidazolyl or 1-methyl-2-imidazolyl; $R^5$ and $R^6$ together with the nitrogen atom to which they are attached form a piperidino, 4-hydroxypiperidino, morpholino, 4-N($R^{11}$)-piperazinyl or 2-methyl-1-imidazolyl group; $R^7$ is H or t-butyl; $R^9$ and $R^{10}$ together with the nitrogen atom to which they are attached form a 4-carbamoylpiperidino or 4-N($R^{12}$)-piperazinyl group; $R^{11}$ is H, methyl, benzyl, 2-hydroxyethyl or acetyl; and $R^{12}$ is H, $C_1$–$C_3$ alkyl, 2-hydroxyethyl or $CSNH_2$.

9. A method as defined in claim 8 wherein in the compound of formula (I) $R^1$ is methyl or ethyl; $R^2$ is n-propyl; $R^3$ is ethyl, n-propyl or allyl; $R^4$ is $COCH_2NR^5R^6$, $CONR^5R^6$, $SO_2NR^9R^{10}$ or 1-methyl-2-imidazolyl; $R^5$ and $R^6$ together with the nitrogen atom to which they are attached form a morpholino or 4-N($R^{11}$)-piperazinyl group; $R^9$ and $R^{10}$ together with the nitrogen atom to which they are attached form a 4-N($R^{12}$)-piperazinyl group; $R^{11}$ is methyl or acetyl; and $R^{12}$ is H, methyl, 2-propyl or 2-hydroxyethyl.

10. A method as defined in claim 9 wherein the compound of formula (I) is selected from:
5-(2-ethoxy-5-morpholinoacetylphenyl)-1-methyl-3-n-propyl-1,6-dihydro-7H-pyrazolo[4,3-d]pyrimidin-7-one;
5-(5-morpholinoacetyl-2-n-propoxyphenyl)-1-methyl-3-n-propyl-1,6-dihydro-7H-pyrazolo[4,3-d]pyrimidin-7-one;
5-[2-ethoxy-5-(4-methyl-1-piperazinylsulphonyl)-phenyl]-1-methyl-3-n-propyl-1,6-dihydro-7H-pyrazolo[4,3-d]pyrimidin-7-one;
5-[2-allyloxy-5-(4-methyl-1-piperazinylsulphonyl)-phenyl]-1-methyl-3-n-propyl-1,6-dihydro-7H-pyrazolo[4,3-d]pyrimidin-7-one;
5-{2-ethoxy-5-[4-(2-propyl)-1-piperazinyl-sulphonyl]phenyl}-1-methyl-3-n-propyl-1,6-dihydro-7H-pyrazolo[4,3-d]pyrimidin-7-one;
5-{2-ethoxy-5-[4-(2-hydroxyethyl)-1-piperazinyl-sulphonyl]phenyl}-1-methyl-3-n-propyl-1,6-dihydro-7H-pyrazolo[4,3-d]pyrimidin-7-one;
5-{5-[4-(2-hydroxyethyl)-1-piperazinylsulphonyl]-2-n-propoxyphenyl}-1-methyl-3-n-propyl-1,6-dihydro-7H-pyrazolo[4,3-d]pyrimidin-7-one;
5-[2-ethoxy-5-(4-methyl-1-piperazinylcarbonyl)-phenyl]-1-methyl-3-n-propyl-1,6-dihydro-7H-pyrazolo[4,3-d]pyrimidin-7-one; and
5-[2-ethoxy-5-(1-methyl-2-imidazolyl)phenyl]-1-methyl-3-n-propyl-1,6-dihydro-7H-pyrazolo[4,3-d]pyrimidin-7-one.

11. A method as defined in claim 10 wherein the compound of formula (I) is 5-(2-ethoxy-5-morpholinoacetylphenyl)-1-methyl-3-n-propyl-1,6-dihydro-7H-pyrazolo[4,3-d]pyrimidin-7-one.

12. A method as defined in claim 10 wherein the compound of formula (I) is 5-(5-morpholinoacetyl-2-n-propoxyphenyl)-1-methyl-3-n-propyl-1,6-dihydro-7H-pyrazolo[4,3-d]pyrimidin-7-one.

13. A method as defined in claim 10 wherein the compound of formula (I) is 5-[2-ethoxy-5-(4-methyl-1- piperazinylsulphonyl)-phenyl]-1-methyl-3-n-propyl-1,6-dihydro-7H-pyrazolo[4,3-d]pyrimidin-7-one.

14. A method as defined in claim 10 wherein the compound of formula (I) is 5-[2-allyloxy-5-(4-methyl-1-piperazinylsulphonyl)-phenyl]-1-methyl-3-n-propyl-1,6-dihydro-7H-pyrazolo[4,3-d]pyrimidin-7-one.

15. A method as defined in claim 10 wherein the compound of formula (I) is 5-{2-ethoxy-5-[4-(2-propyl)-1-piperazinyl-sulphonyl]phenyl}-1-methyl-3-n-propyl-1,6-dihydro-7H-pyrazolo[4,3-d]pyrimidin-7-one.

16. A method as defined in claim 10 wherein the compound of formula (I) is 5-{2-ethoxy-5-[4-(2-hydroxyethyl)-1-piperazinyl-sulphonyl]phenyl}-1-methyl-3-n-propyl-1,6-dihydro-7H-pyrazolo[4,3-d]pyrimidin-7-one.

17. A method as defined in claim 10 wherein the compound of formula (I) is 5-{5-[4-(2-hydroxyethyl)-1-piperazinylsulphonyl]-2-n-propoxyphenyl}-1-methyl-3-n-propyl-1,6-dihydro-7H-pyrazolo[4,3-d]pyrimidin-7-one.

18. A method as defined in claim 10 wherein the compound of formula (I) is 5-[2-ethoxy-5-(4-methyl-1-piperazinylcarbonyl)-phenyl]-1-methyl-3-n-propyl-1,6-dihydro-7H-pyrazolo[4,3-d]pyrimidin-7-one.

19. A method as defined in claim 10 wherein the compound of formula (I) is 5-[2-ethoxy-5-(1-methyl-2-imidazolyl)phenyl]-1-methyl-3-n-propyl-1,6-dihydro-7H-pyrazolo[4,3-d]pyrimidin-7-one.

20. A method as defined in claim 6, wherein said animal is a human.

21. A method as defined in claim 1, wherein said compound, salt or composition is administered intravenously.

22. A method as defined in claim 1, wherein said compound, salt or composition is administered sublingually.

23. A method as defined in claim 1, wherein said compound, salt or composition is administered buccally.

24. A method of treating erectile dysfunction in a male human, comprising orally administering to a male human in need of such treatment an effective amount of a selective cGMP $PDE_v$ inhibitor, or a pharmaceutically acceptable salt thereof, of a pharmaceutical composition containing either entity.

25. A method of treating erectile dysfunction in a male human, comprising orally administering to a male human in need of such treatment an effective amount of a compound selected from:

5-(2-ethoxy-5-morpholinoacetylphenyl)-1-methyl-3-n-propyl-1,6-dihydro-7H-pyrazolo[4,3-d]pyrimidin-7-one;

5-(5-morpholinoacetyl-2-n-propoxyphenyl)-1-methyl-3-n-propyl-1,6-dihydro-7H-pyrazolo[4,3-d]pyrimidin-7-one;

5-[2-ethoxy-5-(4-methyl-1-piperazinylsulphonyl)-phenyl]-1-methyl-3-n-propyl-1,6-dihydro-7H-pyrazolo[4,3-d]pyrimidin-7-one;

5-[2-allyloxy-5-(4-methyl-1-piperazinylsulphonyl)-phenyl]-1-methyl-3-n-propyl-1,6-dihydro-7H-pyrazolo[4,3-d]pyrimidin-7-one;

5-{2-ethoxy-5-[4-(2-propyl)-1-piperazinyl-sulphonyl]phenyl}-1-methyl-3-n-propyl-1,6-dihydro-7H-pyrazolo[4,3-d]pyrimidin-7-one;

5-{2-ethoxy-5-[4-(2-hydroxyethyl)-1-piperazinyl-sulphonyl]phenyl}-1-methyl-3-n-propyl-1,6-dihydro-7H-pyrazolo[4,3-d]pyrimidin-7-one;

5-{5-[4-(2-hydroxyethyl)-1-piperazinylsulphonyl]-2-n-propoxyphenyl}-1-methyl-3-n-propyl-1,6-dihydro-7H-pyrazolo[4,3-d]pyrimidin-7-one;

5-[2-ethoxy-5-(4-methyl-1-piperazinylcarbonyl)-phenyl]-1-methyl-3-n-propyl-1,6-dihydro-7H-pyrazolo[4,3-d]pyrimidin-7-one; and 5-[2-ethoxy-5-(1-methyl-2-imidazolyl)phenyl]-1-methyl-3-n-propyl-1,6-dihydro-7H-pyrazolo[4,3-d]pyrimidin-7-one;

or a pharmaceutically acceptable salt thereof;

or a pharmaceutical composition containing either entity.

26. A method as defined in claim 25, wherein said compound is 5-[2-ethoxy-5-(4-methyl-1-piperazinylsulphonyl)-phenyl]-1-methyl-3-n-propyl-1,6-dihydro-7H-pyrazolo[4,3-d]pyrimidin-7-one, or a pharmaceutically acceptable salt thereof, or a pharmaceutical composition containing either entity.

* * * * *

US006469012C1

(12) EX PARTE REEXAMINATION CERTIFICATE (7846th)
United States Patent
Ellis et al.

(10) Number: US 6,469,012 C1
(45) Certificate Issued: Nov. 2, 2010

(54) PYRAZOLOPYRIMIDINONES FOR THE TREATMENT OF IMPOTENCE

(75) Inventors: Peter Ellis, Sandwich (GB); Nicholas Kenneth Terrett, Sandwich (GB)

(73) Assignee: Pfizer, Inc., New York, NY (US)

Reexamination Request:
No. 90/006,617, Sep. 29, 2003
No. 90/006,886, Dec. 15, 2003
No. 90/007,110, Jul. 7, 2004
No. 90/007,478, Mar. 23, 2005

Reexamination Certificate for:
Patent No.: 6,469,012
Issued: Oct. 22, 2002
Appl. No.: 08/549,792
Filed: Mar. 4, 1996

(22) PCT Filed: May 13, 1994
(86) PCT No.: PCT/EP94/01580
§ 371 (c)(1), (2), (4) Date: Mar. 4, 1996
(87) PCT Pub. No.: WO94/28902
PCT Pub. Date: Dec. 22, 1994

(30) Foreign Application Priority Data
Jun. 9, 1993 (GB) .............................................. 9311920

(51) Int. Cl.
A61K 31/505 (2006.01)
A61K 31/535 (2006.01)

(52) U.S. Cl. .............................. 514/234.5; 514/252.16; 514/262.1
(58) Field of Classification Search .................. 514/258, 514/929
See application file for complete search history.

(56) References Cited
U.S. PATENT DOCUMENTS

| 4,060,615 | A | 11/1977 | Matier et al. | 424/251 |
|---|---|---|---|---|
| 4,389,330 | A | 6/1983 | Tice et al. | |
| 5,075,114 | A | 12/1991 | Roche | |
| 5,082,669 | A | 1/1992 | Shirai et al. | |
| 5,236,908 | A | 8/1993 | Gruber et al. | 514/46 |
| 5,250,534 | A | 10/1993 | Bell et al. | 514/258 |
| 5,260,322 | A | 11/1993 | Nakasima et al. | 514/341 |
| 5,272,147 | A | 12/1993 | Bell et al. | 514/234.2 |
| 5,294,612 | A | 3/1994 | Bacon et al. | |
| 5,346,901 | A | 9/1994 | Bell et al. | 514/258 |
| 5,405,847 | A | 4/1995 | Dieter et al. | |
| 5,426,107 | A | 6/1995 | Bell et al. | 514/234.2 |
| 5,430,048 | A | 7/1995 | Gadwood | 514/386 |
| 5,436,233 | A | 7/1995 | Lee | |
| 5,482,941 | A | 1/1996 | Terrett | 514/253 |
| 5,488,055 | A | 1/1996 | Kumar et al. | |
| 5,488,059 | A | 1/1996 | Buhl | 514/349 |
| 5,541,187 | A | 7/1996 | Bacon et al. | |
| 5,591,742 | A | 1/1997 | Bell et al. | 514/234.5 |
| 5,614,530 | A | 3/1997 | Kumar et al. | |

(Continued)

FOREIGN PATENT DOCUMENTS

| CA | 2163446 | 7/1998 |
|---|---|---|
| EP | 0 340 270 | 11/1989 |
| EP | 0214708 | 12/1989 |

(Continued)

OTHER PUBLICATIONS

Australian Documents.
Proceeding No. V 604 of 2002.
Application, Statement of Claim & Particulars of Invalidity for Australian (Sep. 17, 2002).

(Continued)

Primary Examiner—Dwayne C Jones

(57) ABSTRACT

The use of a compound of a formula (I)

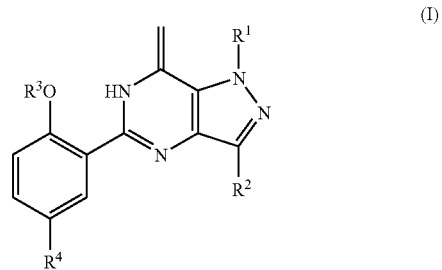

wherein $R^1$ is H; $C_1$—$C_3$ alkyl; $C_1$—$C_3$ perfluoroalkyl; or $C_3$—$C_5$ cycloalkyl; $R^2$ is H; optionally substituted $C_1$—$C_6$ alkyl; $C_1$—$C_3$ perfluoroalkyl; or $C_1$—$C_6$ cycloalkyl; $R^3$ is optionally substituted $C_1$—$C_6$ alkyl; $C_1$—$C_6$ perfluoroalkyl; $C_3$—$C_5$ cycloalkyl; $C_3$—$C_6$ alkenyl; or $C_3$—$C_6$ alkynyl; $R^4$ is optionally substituted $C_1$—$C_4$ alkyl, $C_2$—$C_4$ alkenyl, $C_2$—$C_4$ alkanoyl, (hydroxy)$C_2$—$C_4$ alkyl or ($C_2$—$C_3$ alkoxy)$C_1$—$C_2$ alkyl; $CONR^5R^6$; $CO_2R^7$; halo; $NR^5R^6$; $NHSO_2NR^5R^6$; $NHSO_2R^8$; $SO_2NR^9R^{10}$; or phenyl, pyridyl, pyrimidinyl, imidazolyl, oxazolyl, thiazolyl, thienyl or triazolyl any of which is optionally substituted with methyl; $R^5$ and $R^6$ are each independently H or $C_1$—$C_4$ alkyl, or together with the nitrogen atom to which they are attached form an optionally substituted pyrrolidinyl, piperidino, morpholino, 4-N($R^{11}$)-piperazinyl or imidazolyl group; $R^7$ is H or $C_1$—$C_4$ alkyl; $R^8$ is optionally substituted $C_1$—$C_3$ alkyl; $R^9$ and $R^{10}$ together with the nitrogen atom to which they are attached form an optionally substituted pyrrolidinyl, piperidino, morpholino or 4-N($R^{12}$)-piperazinyl group; $R^{11}$ is H; optionally substituted $C_1$—$C_3$ alkyl; (hydroxy)$C_2$—$C_3$ alkyl; or $C_1$—$C_4$ alkanoyl; $R^{12}$ is H; optionally substituted $C_1$—$C_6$ alkyl; $CONR^{13}R^{14}$; $CSNR^{13}R^{14}$; or $C(NH)NR^{13}R^{14}$; and R?13? and $R^{14}$ are each independently H; $C_1$—$C_4$ alkyl; or substituted $C_2$—$C_4$ alkyl; or a pharmaceutically acceptable salt thereof, or a pharmaceutical composition containing either entity, for the manufacture of a medicament for the curative or prophylactic treatment or erectile dysfunction in a male animal, including man; a pharmaceutical composition for said treatment; and a method of said treatment of said male animal with said pharmaceutical composition or with said either entity.

U.S. PATENT DOCUMENTS

| | | | |
|---|---|---|---|
| 5,656,629 A | 8/1997 | Bacon et al. | |
| 5,734,053 A | 3/1998 | Terrett | 544/277 |
| 5,736,548 A | 4/1998 | Bacon et al. | |
| 5,780,450 A | 7/1998 | Shade | |
| 5,990,111 A | 11/1999 | Johnson | 514/252 |
| 6,037,346 A | 3/2000 | Doherty, Jr. et al. | 514/258 |
| 6,100,270 A | 8/2000 | Campbell | 514/258 |
| 6,127,363 A | 10/2000 | Doherty, Jr. et al. | 514/220 |
| 6,130,333 A | 10/2000 | Huang et al. | 546/118 |
| 6,133,326 A | 10/2000 | Mayne | 514/859 |
| 6,156,753 A | 12/2000 | Doherty, Jr. et al. | 514/252 |
| 6,177,471 B1 | 1/2001 | Menander et al. | 514/569 |
| 6,225,315 B1 | 5/2001 | Ellis | 514/250 |
| 6,235,742 B1 | 5/2001 | Bell et al. | 514/258 |
| 6,251,904 B1 | 6/2001 | Bunnage et al. | 514/252.6 |
| 6,271,228 B1 | 8/2001 | Grossman | 514/234.2 |
| 6,288,118 B1 | 9/2001 | Nieman et al. | 514/572 |
| 6,300,335 B1 | 10/2001 | Campbell et al. | 514/260 |
| 6,303,661 B1 | 10/2001 | Demuth et al. | 514/866 |
| 6,333,330 B1 | 12/2001 | Bunnage et al. | 514/258 |
| 6,350,751 B1 | 2/2002 | Hughes et al. | 514/252.16 |
| 6,407,114 B1 | 6/2002 | Bunnage et al. | 514/258 |
| 6,420,557 B1 | 7/2002 | Harris et al. | 544/262 |
| 6,436,944 B1 | 8/2002 | Maytom | 514/258 |
| 6,440,982 B1 | 8/2002 | Maw et al. | 514/563.2 |
| 6,455,564 B1 | 9/2002 | Meglasson et al. | 514/387 |
| 6,503,908 B1 | 1/2003 | Maw | 514/243 |
| 6,534,511 B1 | 3/2003 | Campbell | |
| 6,586,439 B2 | 7/2003 | Maw et al. | 514/263 |
| 6,593,332 B2 | 7/2003 | Maw et al. | 514/263.2 |
| 6,656,945 B2 | 12/2003 | Campbell et al. | 514/258 |
| 6,670,366 B1 | 12/2003 | Bunnage et al. | 514/262.1 |

FOREIGN PATENT DOCUMENTS

| | | |
|---|---|---|
| EP | 0463756 | of 1992 |
| EP | 0463756 | 1/1992 |
| EP | 0463756 A1 | 1/1992 |
| EP | 0 463 756 | 1/1992 |
| EP | 0293063 | 3/1992 |
| EP | 0 480 659 | 4/1992 |
| EP | 0340270 | 7/1992 |
| EP | 0 526 004 | 2/1993 |
| EP | 0526004 | 2/1993 |
| EP | 0526004 A1 | 2/1993 |
| EP | 0 533 280 | 3/1993 |
| EP | 0347146 | 9/1993 |
| EP | 0347027 | 8/1994 |
| EP | 0480659 | 9/1996 |
| EP | 0527879 | 2/1997 |
| EP | 0 854 720 | 7/1998 |
| EP | 0 896 538 | 2/1999 |
| EP | 0854720 | 8/1999 |
| EP | 0699439 | 10/1999 |
| EP | 0533280 | 8/2000 |
| EP | 0896538 | 7/2001 |
| JP | 662410 | 8/1994 |
| JP | 75482 | 1/1995 |
| JP | 729938 | 4/1995 |
| JP | 2612175 | 2/1997 |
| JP | 2635291 | 4/1997 |
| JP | 2648328 | 5/1997 |
| JP | 2807092 | 7/1998 |
| JP | 3010153 | 12/1999 |
| JP | 3020757 | 1/2000 |
| JP | 3041051 | 3/2000 |
| KR | 950013758 | 1/1995 |
| KR | 0013758 | 11/1995 |
| KR | 95 0013758 | 11/1995 |
| KR | 0005839 | 4/1997 |
| KR | 970005839 | 4/1997 |
| KR | 97 0005839 | 4/1997 |
| KR | 0007188 | 5/1997 |
| KR | 97 0007188 | 5/1997 |
| KR | 970007188 | 5/1997 |
| KR | 0232688 | 9/1999 |
| KR | 0233323 | 9/1999 |
| KR | 10 023323 | 9/1999 |
| KR | 10 0232686 | 9/1999 |
| KR | 100232688 | 9/1999 |
| KR | 100233323 | 9/1999 |
| KR | 0278522 | 10/2000 |
| KR | 100278522 | 10/2000 |
| KR | 10 0278522 | 10/2000 |
| WO | WO 93/06104 | * 4/1993 |
| WO | WO 9306104 | 4/1993 |
| WO | WO 9307149 | 4/1993 |
| WO | WO 93/07149 | 4/1993 |
| WO | WO 9428902 | 12/1994 |
| WO | WO 9429277 | 12/1994 |
| WO | WO 94/29277 | 12/1994 |
| WO | WO 9703675 | 6/1997 |
| WO | WO09703675 | 6/1997 |

OTHER PUBLICATIONS

Transcript of Proceedings dated Sep. 9, 2003.
Notice of Appearance of Blake Dawson Waldron.
Further Amended Application (Aug. 5, 2003).
Further Amended Statement of Claim (Aug. 5, 2003).
Order dated May 29, 2003.
Order dated Jun. 10, 2003.
Letter to Blakes Characterizing Invention (Jan. 20, 2003).
Cross Claim (Jun. 6, 2003).
Notice of Motion (May 29, 2003).
Affidavit of Sally Ann Nicholson (May 29, 2003).
Exhibit SAN–1.
Exhibit SAN–2.
Exhibit SAN–3.
Exhibit SAN–4.
Exhibit SAN–5.
Exhibit SAN–6.
Proceeding No. V 108 of 2003.
Order dated May 26, 2003.
Order dated Jun. 10, 2003.
Application (Apr. 1, 2003).
Proceeding No. V 111 of 2003.
Order dated May 19, 2003.
Order dated May 26, 2003.
Order dated Jun. 10, 2003.
Facsimile to DCC inRelation to Answer to Request for Further and Better Particulars (May 23, 2003).
Facsimile to Corns Providing Further Particulars (May 30, 2003).
Cross Claim (Jun. 6, 2003).
Notice of Motion (May 29, 2003).
Proceeding No. V 108 of 2003:
Order dated May 29, 2003.
Proceeding No. V 111 of 2003.
Affidavit of Sally Ann Nicholson (May 29, 2003).
Exhibit SAN–1.
Exhibit SAN–2.
Exhibit SAN–3.
Exhibit SAN–4.
Exhibit SAN–5.
Exhibit SAN–6.
Affidavit of Sally Ann Nicholson (May 5, 2003).

Exhibit SAN–1.
Exhibit SAN–2.
Exhibit SAN–3.
Exhibit SAN–4.
Exhibit SAN–5.
Exhibit SAN–6.
Exhibit SAN–7.
Exhibit SAN–8.
Exhibit SAN–9.
Exhibit SAN–10.
Exhibit SAN–11.
Exhibit SAN–12.
Exhibit SAN–13.
Exhibit SAN–14.
Exhibit SAN–15.
Exhibit SAN–16.
Exhibit SAN–17.
Exhibit SAN–18.
Proceeding No. V. 604 of 2002.
Further Amended Particulars of Invalidity (Jul. 24, 2003).
Defense to Cross–Claim (Jul. 24, 2003).
Particluars of Invalidity to the Defense to Cross–Claim (Jul. 24, 2003).
Transcript of Proceedings dated Apr. 1, 2003.
Proceeding No. V 111 of 2003.
Transcript of Proceedings dated Jun. 10, 2003.
Defense to Cross–Claim (Jul 11, 2003).
Proceeding No. V 367 of 2003.
Order dated Jun. 10, 2003.
Proceeding No. V 604 of 2002.
Application (Sep. 17, 2002).
Amended Application (Feb. 10, 2003).
Statement of Claim (Sep. 17, 2002).
Amended Statement of Claim (Feb. 10, 2003).
Particulars of Invalidity (Sep. 17, 2002).
Amended Particulars of Invalidity (Feb. 10, 2003).
Defense (Jan. 24, 2003).
Reply to Defense (Feb. 10, 2003).
Affidavit of Stephen Marcus Stem (May 27, 2003).
Proceeding No. V 111 of 2003.
Order dated Apr. 1, 2003.
Notice of Appearance (Mar. 28, 2003).
Application (Mar 6, 2003).
Proceeding No. V 367 of 2003.
Application under Preliminary Discovery under Order 15A rule 6 (May 9, 2003).
Affidavit of Matthew Guy Swinn (May 8, 2003).
Exhibit MGS–1.
Exhibit MGS–2.
Exhibit MGS–3.
Exhibit MGS–4.
Exhibit MGS–5.
Exhibit MGS–6.
Exhibit MGS–7.
Exhibit MGS–8–10.
Exhibit MGS–11.
Exhibit MGS–12.
Exhibit MGS–13.
Exhibit MGS–14.
Exhibit MGS–15.
Proceeding No. V 604 of 2002.
Order dated Oct. 22, 2002.
Order dated Apr. 1, 2003.
Notice of Appearance (Oct. 17, 2002).
Request for Further and Better Particulars of Invalidity (Dec. 6, 2002).
Answer to Request for Further and Better Particulars of Invalidity (Dec. 23, 2002).
Proceeding No. V 604 of 2003.
Notice to Produce (Oct. 17, 2002).
Proceeding No. V 111 of 2003.
Reasons for Judgment in the Patent Amendment Issue (Sep. 18, 2003).
Statement of Grounds for Amending Australian Patent 676571 (Jul. 25, 2003).
Outline of the Respondent's submissions in relation to the construction of the proposed amended claim 10.
Proceeding No. V 604 of 2002.
Order dated Sep. 19, 2003.
Australian Official Journal (Apr. 17, 2003).
Request to Amend the Patent and/or Entry in the Register (Apr. 3, 2003).
Notice of Application to Amend the Patent pursuant to s105 (Apr. 17, 2003).
Amended advertisement.
Notice of Application to Amend Letters Patent Pursuant to s105 rule 10(1).
Notification from the APO regarding the s105 amendment (Apr. 10, 2003).
Statement of Grounds Relied Upon for the Amendment of Australian Patent 676571 (Jul. 21, 2003).
Statement of Grounds Relied Upon by "Lilly" in Opposition to the Proposed Amendment (Jul. 29, 2003).
Applicant's Submissions on the Amendment (Sep. 8, 2003).
First Respondent's Outline of Submissions relating to the s105 Amendment (Sep. 8, 2003).
Proceeding No. V 111 of 2003.
Statement of Grounds relied upon by "Bayer" in Opposition to the Proposed Amendment (Aug. 7, 2003).
Repondent's Outline of Submissions (Sep. 8, 2003).
Brazilian Documents.
Homologation of a Foreign Ruling Lawsuit, Case No. 79–21, Filed before the Brazillian Federal Supreme Court, Foreign Ruling 7921 Re EP 0 702 555 (English Language Translation) (vol. 1 of 2).
Homologation (vol. 2 of 2).
English Translation of Nullity Action 2003.61.00.010308.3 (*Bayer* v. *Pfizer* Re Pat No. PI 1100088–0) (1 of 4).
English Translation of Nullity Action (2 of 4).
English Translation of Nullity Action (3 of 4).
Ignarro et al., Biochem and Biophys, Rsch., 843–850 (1990).
Brazil Citation Annex.
English Translation of Nullity Action (4 of 4).
Trigo–Rocha et al., Am. J. Phys., 264, H419–H422 (1993).
Trigo–Rocha, J. Urology, 145, 872–877 (1993).
Korenman et al., JAGS:41, 363–366 (1993).
*Pfizer* v. *Eli Lilly* (Inhibitory Action 000.03.037147–3): vols. 1–14, (English).
*Pfizer* v. *Eli Lilly* (Case No. 293.588.4): Bill of Review Against Rejection of the Preliminary Injunction (vol. 1). (English).
*Pfizer* v. *Eli Lilly* ( Case No. 315.955.4): Bill of Review Against the Redistribution of the Action (English).
*Pfizer* v. *Eli Lilly*: Unspecified Provisional Remedy Supreme Court Rio (vol. 1) (English).
*Pfizer* v. *Eli Lilly*: Unspecified Provisional Remedy Supreme Court Brasilia (vol. 1) (English).

*Eli Lilly* v. *Pfizer* (Declaratory Action 2003.001.034974–6): vols. 1–6 (English).
Change of Jurisdiction (English).
*Pfizer* v. *Eli Lilly* (Case No. 2003.002.05456): Bill of Review Against the Grant of the Preliminary Injunction (vols. 1–6) (English).
*Pfizer* v. *Eli Lilly* (Case No. 10146/2003): Bill of Review Against Rejection of Motion Seeking Removal (vols. 1–2) (English).
*Lilly* v. *Pfizer*: Homologation of a Foreign Ruling No. 7921 (vols. 3–5). (English).
*Bayer* v. *Pfizer* (Inhibitory Action No. 2003.03.040625–0): vols. 1–12. (English).
*Pfizer* v. *Bayer* (Case No. 294.153.4): Bill of Review Against the Grant Preliminary Injunction (English).
Canadian Documents.
*Bayer, et al* v. *Pfizer Research* (T2097–02).
Amended Statement of Claim (Mar. 7, 2003).
Defence (Apr. 7, 2003).
Reply (Apr. 11, 2003).
*Pfizer Research* v. *Bayer* (T2081–02).
Motion Record.
*Pfizer Research* v. *Bayer* (T2082–02).
Plaintiff's Responding Motion Record (Defendant's Motion to Strike) (Mar. 21, 2003).
*Bayer, et al.* v. *Pfizer Research* (T865–02).
Statement of Defense (Sep. 10, 2002).
*Lilly Icos, et al.* v. *Pfizer Research* (T341–02):.
Statement of Claim (Mar. 1, 2002).
Statement of Defence.
*Bayer, et al.* v. *Pfizer Research* (T865–02):.
Tender
CA 2,163,446 (first cited above).
*Bayer, et al.* v. *Pfizer Research, et al:.*
Order (Jun. 6, 2002).
*Bayer, et al.,* v. *Pfizer Research, et al.*
Tender (Jun. 11, 2002).
*Lily Icos, et al.* v. *Pfizer Research* (T341–02).
Statement of Claim (Mar. 1, 2002).
Amended Statement of Defense (Amended Pursuant to the Order of Prothonotary Lafreniere, dated Oct. 2, 2002 and Rule 200.
Canada Impeachement Papers.
CA 2,163,446 (first cited above).
*Lilly Icos, et al.* v. *Pfizer Research*.
Statement of Claim (T341–02) (Mar. 1, 2002).
WO 94/28902 (first cited above).
CA 9311920.4 (first cited above).
EP 0 526 004 (first cited above).
EP 0 463 756 (first cited above).
Clin. Rsch., v. 36, No. 1, pp. 95A, 123A (1988).
Korenman et al., JAGS 41:363–366 (1993).
Morley, Impotence v. 93, No, 3, pp. 6572 (1993).
Rafjer et al., NE J. Med., v. 326, No. 2, pp. 90–94 (1992).
Murray et al., DN&P, 6(3), 150–156 (1993).
Trigo–Rocha et al., J. Urology, v. 149, 872–877 (1993).
J. Urology, AUA 88th Annual Meeting 285A (1993).
Nicholson, TIPS, v. 12, 19–27 (1991).
Margaret A Bush Dissertation (1993).
*Bayer, et al.* v. *Pfizer Research* (T865–02).
Statement of Claim (Jun. 5, 2002).
Jun. 6, 2002 Order (Jun. 6, 2002).
Consent (Jul. 9, 2002).
Tender.
Jul. 15, 2003 Order.
Sep. 9, 2002 Letter from D. MacOdram.
Oct. 1, 2003 Letter from M. Charles.
WO 97/03675 (first cited above).
Amended Statement of Defense (Oct. 23, 2002).
Further Amended Statement of Defense (Nov. 27, 2002).
Reply (Dec. 5, 2002).
Disclaimer w/respect to Canadiam Pat No. 2,163,446 (Nov. 8, 2002).
*Eli Lilly, et al* v. *Pfizer Research* (T341–02).
Statement of Claim (Mar. 1, 2002).
Mar. 4, 2002 Order.
Tender of Payment into Court (Mar. 4, 2002).
Affidavit of J. Clarke (Mar. 6, 2002).
Affidavit of Service (Mar. 6, 2002).
Jul. 23, 2003 Order.
Aug. 12, 2002 Order.
Aug. 26, 2002 Order.
Statement of Defense (Sep. 10, 2002).
Sep. 13, 2002 Letter from D. Cameron.
Sep. 23, 2002 Order.
Oct. 2, 2002 Order.
Amended Statement of Defense (Oct. 16, 2002).
Oct. 18, 2002 Letter from D. Cameron.
Oct. 21, 2002 letter from M. Charles.
Reply to Statement of Defense (Oct. 28, 2002).
Request to Admit Facts (Oct. 28, 2002).
Revocation of Appointment of Agent & Appointment of Agent.
Response to Request to Admit (Nov. 27, 2002).
Claims of CA Patent 2,163,446.
Not. of Change of Solicitors.
Amended Statement of Claim (Feb. 11, 2003).
*Bayer, et al* v. *Pfizer Research* (T865–02).
Defendant's Motion Record (Jul. 10, 2002).
Motion Record.
*Lilly Icos, et al.* v. *Pfizer Research* (T341–02).
Motion Record (Mar. 4, 2002).
Motion Record for Motion Returnable Jul. 22, 2002.
Supplementary Motion Record on Costs.
*Lilly Icos, et al.* v. *Pfizer Research* (T341–02).
Defendant's Responding Motion Record (Sep. 16, 2002).
Defendant's Motion Record (Rule 369 Motion on Consent for an Extension of Time) (Aug. 2, 2002).
Plaintiff's Motion Record (Motion to Strike Paragraphs of the Statement of Defense and for Particulars, Returnable Sep. 23, 2002.
Responding Motion Record of the Defendant (Pllaintiff's Motion to Strike and for Particulars) (Sep. 25, 2002).
*Pfizer Research, et al* v. *Bayer AG* (T2027–02).
Notice of Discontinuance (Feb. 21, 2003).
Statement of Claim (Dec. 5, 2002).
*Pfizer Research* v. *Lilly Icos* ( 2025–02).
Notice of Discontinuance (Feb. 21, 2003).
Statement of Claim (Dec. 5, 2002).
*Bayer, et al.* v. *Pfizer Research* (T1964–02).
Motion Record (Feb. 28, 2003).3
Defedat's Supplementary Motion Record (Motion to Strike Statement of Claim) (Dec. 13, 2002).
Plaintiff's Motion Record (Defendant's Motion to Strike Statement of Claim) (Dec. 13, 2002).
Defendant's Motion Record (Motion to Strike. Statement of Claim) (Dec. 11, 2002).
Reply (Feb. 26, 2003).

Affidavit of Service (Jan. 22, 2003).
Statement of Defense (Jan. 22, 2003).
Dec. 16, 2002 Order.
Tender Payment into Court.
Dec. 3, 2002 Order.
Statement of Claim (Nov. 22, 2002).
*Pfizer Research, et al v. Bayer AG* (T2081–02).
Plaintiff's Motion Record (Motion for Extension of Time to Serve Claim) (Feb. 18, 2003).
Statement of Claim (Dec. 12, 2002).
Amended Statement of Claim (Jan. 31, 2003).
Affidavit of Service (Feb. 6, 2003).
Request for Service Abroad of judicial Documents (Feb. 17, 2003).
Klageschrift (German) (Dec. 12, 2002).
Summary of Documents to be Served.
Notice and Summary of Documents.
Feb. 19, 2003 Letter from D. MacOdrum.
*Pfizer Research v. Lilly Icos* (T2082–02).
Motion Record of the Defendants Lilly Icos and Eli Lilly Canada, Inc. (Returnable Mar. 3, 2003).
Amended Return of Service Affidavit of K. Dunn (Feb. 3, 2003).
Affidavit of Service (Feb. 7, 2003).
Amended Statement of Claim (Jan. 31, 2003).
Statement of Claim (Dec. 12, 2002).
*Bayer, et al v. Pfizer Research* (T2097–02).
Statement of Claim (Dec. 13, 2002).
*Pfizer v. Lilly* Patent Infringment (T1721–03).
Statement of Claim (Sep. 19, 2003).
Direction of Justice (Sep. 19, 2003).
Federal Court Fax (Oct. 7, 2003).
Order (Oct. 16, 2003).
Motion Record (Planitiff's Motion for an Interim Injunction) (Sep. 23, 2003) (vols. 1–2).
Motion Record of the Defendants (Oct. 28, 2003) (vols. 1 and 3–6).
Defendants' Written Submissions (Oct. 28, 2003).
Protective Order (Oct.16, 2003).
*Bayer AG v. Pfizer* (T865–02).
Order (Jul. 22, 2003).
*Bayer v. Pfizer* (T865–02).
Motion Record (Jun. 24, 2003).
Brief of Autorities.
Order (Jul. 17, 2003).
*Lilly Icos v. Pfizer* (T341–02).
Defendant's Responding Motion Record (Motion to Consolidate) (Jul. 8, 2003).
Plaintiff's Responding Motion Record (Motion to Consolidate) (Jul. 15, 2003).
Plaintiff's Brief of Authorities (Jul. 15, 2003).
*Lilly v. Pfizer* (T341–02).
Amended Reply to Amended Statement of Defence (Mar. 24, 2003).
Notice of Status Review (Apr. 28, 2003).
Response to Status Review (Jun. 2, 2003).
Order (Jun. 26, 2003).
Affidavit of Documents of Lilly Icos (May 28, 2003).
Affidavit of Documents of Eli Lilly (May 22, 2003).
Request for Extension of Time (Jul. 21, 2003).
Order (Jul. 21, 2003).
Order (Jul. 10, 2003).
*Bayer v. Pfizer* (T1954–02).
Order (Mar. 25, 2003).
*Pfizer v. Bayer* (T2081–02).
Consent (Jun. 12, 2003).
Order (Feb. 28, 2003).
Order (Mar. 17, 2003).
Order (Apr. 17, 2003).
Consent (Apr. 30, 2003).
Order (May 30, 2003).
Amended Order (Jun. 16, 2003).
Order (Jul. 10, 2003).
Notice of Discontinuance (Jul. 18, 2003).
*Pfizer v. Bayer* (T2081–02).
Defendant's Motion Record on Consent to Extend Time (Apr. 7, 2003).
Defendant's Motion Record on Consent to Extend Time (May 28, 2003).
Plaintiff's Motion Record to Extend Time (Jun. 11, 2003).
Defendant's Motion Record on Consent to Extend Time (Jul. 27, 2003).
*Pfizer v. Lilly* (T2082–02).
Reasons for Order and Order (Jun. 17, 2003).
Chilean Documents.
Appln. No. 1.127–98: Decision from the Appeals Court Rejecting the Application w/ English Language Translation (Sep. 24, 2002).
Pfizer's Writ of Complaint to the Supreme Court of Justice (English).
Request to the Court to Appoint an Examiner (in English) (Mar 8, 2002).
Brief Filed by ASILFA (in English) (Apr. 4, 2002).
Brief Filed by Pfizer Objecting to Documents (in English) (Apr. 8, 2002).
Memo Filed by CBLH during Oral Proceedings (in English) (Apr. 4, 2002).
Requests to Court to Appoint an Examiner (May 8, 2002).
Main Petition (English).
Chilean Supreme Court Papers Re Appln. No. 1127–98 (w/ English translations).
Chilean Arbitral Court of Industrial Property Papers Re Appln. No. 1127–98 (w/ English translations).
Chinese Documents:
Patent No. ZL94192386.X:.
Notice of Oral Hearing (English) (Jul. 10, 2002).
Notice of Translation (English) (Jul. 10, 2002).
English Translation of Response Filed on Jan. 28, 2002.
Revised Declarations for Dr. Boolell and Dr. Terrett (Oct. 23, 2002).
English Translation of Opponent 1 Arguments.
English Translation of Pfizer Response Filed After Hearing.
Patent No. ZL94192386.X:.
Notice of Acceptance of Request for Invalidation (English) ( Sep. 19, 2003).
Request for Invalidation (English).
Response to Request (English) (Nov. 3, 2001).
Further Observations for Requester 1 (English) (Jul. 10, 2002; Aug. 2, 2002).
Response to Further Observations of Requester 1 (English) (Sep. 17, 2002).
Acceptance of Request for Invalidation (English) (Dec. 13, 2001).
Request for Announcement of Invalidation (English).
Response to Requester (English) (Jan. 28, 2002).
Further Observations of Requester 2 (English) (Aug. 12, 2002).

Final Response to Reasons for Invalidation (English) (Sep. 16, 2002).
Evidence filed by Patentee:.
Truss, M. C., et al., *Role of the Nitric Oxide Donor Linsidomine Chlorohydrate (SIN–1) in the Diagnosis and Treatment of Erectile Dysfunction*, Urology, vol. 44, No. 1, pp. 553–556, (1994).
Lugg, J.A., et al., *The Role of Nitric Oxide in Erectile Function*, Journal of Andrology, vol. 14, No. 1, pp. 2–4, (1993).
Blakeslee, S., *Chemical A Factor in Male Impotence*, The New York Times, 1992.
Trigo–Rocha, F., et al., *Intracellular Mechanism of Penile Erection in Monkeys*, Neurology and Urodynamics, vol. 13, pp. 71–80, (1994).
Trigo–Rocha, F., et al., *The effect of Intracavernous Injection of potassium channel openers in monkeys and dog*, Int. J. Impotence Res., vol. 7, pp. 41–48 (1995).
Trigo–Rocha, F., et al., *Sodium nitroprusside: physiologic effects as a nitric oxide donor in three species*, Int. J. Impotence Res., vol. 7, pp. 49–56, (1995).
Stief, C. G., et al., *Preliminary report on the effect of the nitric oxide donor SIN–1 on human cavernous tissue in vivo*, World J. Urol.,vol. 237–239, (1991).
Fareman, M. M., et al., *Approaches for the Development of Oral Drug Therapies for Erectile Dysfunction*, Seminars in Urology, vol. VIII, No. 2 p. 107–112, (1990).
Owen, J. A., et al., *Topical Nitroglycerine: A Potential Treatment for Impotence*, Journal of Urology, vol. 141, pp. 543–545, (1989).
Traish, A. M., et al., *A Heterogeneous Population of $\alpha_1$ Adrenergic Receptors Mediates Contraction of Human Corpus Caverrnosum Smooth Muscle to Norepinephrine*, Journal of Urology, vol. 153, pp. 222–227, (1996).
Extract from Proprietor's EPO submission Jun. 22, 2001.
Witness statement of Peter Ellis in UK proceedings.
Statement of Martyn Frank Burslem.
Statement of Nicholas Keneneth Terrett.
Statement of Michael J. Allen.
Statement of Mitradev Boolell.
Boolell, M., et al., *Sildenafil, a novel effective oral theraphy for male erectile dysfunction*, British Journal of Urology, vol. 78, pp. 257–162, (1996).
Bardley, I., et al., *UK–92, 480, A New Oral Theraphy for Erectile Dysfunction, a Double–blind, Placebo Controlled Trial with Treatment Take as Required*, Proceedings of the American Urological Association, vol. 155, pp. 495A.
Boolell, M., et al., *Slidenafil: an orally active type 5 cyclic GMP—specific phosphodiestrerase inhibitor for the treatment of penile erectile dysfunction*, Int. Journal of Impotence Res., vol. 8 , pp. 47–52, (1996).
Lue, T. F., et al., *A Study of Slidenafil (Viagra™), A New Oral Agent for the Treatment of Male Erectile Dysfunction*, Journal of Urology, vol. 157, No. 4, (1997).
Goldstein, I., et al., British Journal of Urology, vol. 80, supplement 2, (1997).
Goldstein, I., et al., *Oral Sildenafil In The Treatment of Erectile Dysfunction*, The New England Journal of Medicine, vol. 338, No. 20, pp. 1397–1404, 1998.
Statement of Martyn Frank Bursiem.
Indicia of Inventive Step, pp. 59–62.
EP 0 463 756 (first cited above).
EP 0 526 004 (first cited above).
Expert Report of Louis Ignarro.
Exhibit 23.

Chinese translation of Trigo–Rocha, F., et al., *Sodium nitroprusside: physiologic effects as a nitric oxide donor in three species*, Int. J. Impotence Res., vol. 7 pp. 49–56, (1995).
Stief, C. G., et al., *The Effect of the Specific Phosphodiesterase (PDE) Inhibitors on Human and Rabbit Cavernous Tissue In Vitro and In Vivo*, Journal of Urology, vol. 159, pp. 1390–1393, (1998).
Exhibit 26.
Owen, J. A., et al., *Tropical NItroglycerin: A Potential Treatment of Importance*, Journal of Urology vol. 141, pp. 546–548, (1989).
Columbian Documents.
Documents of Columbian Annulment Action (Expediente No. 6608).
EPO Documents.
T 1212/01–332.
Opponent 2 Letter of Oct. 15, 2002.
Opponent 9 Letter of Oct. 17, 2002.
Opponents 3 and 6 Letter of Oct. 21, 2002.
Opponent 12 Letter of Oct. 11, 2002.
Opponent 4 Letter of Oct. 10, 2002.
Opponent 5 Letter of Oct. 9, 2002.
English Translation of Bayer's Letter dated Oct. 17, 2002.
English Translation of the Submissions Filed by Merck Patent GmbH dated Oct. 10, 2002.
T 121/01–332.
Response Filed with the EPO In Jul. 24, 2003.
*Drugs and male sexual function*, British Medical Journal, vol. 2, PT 6195, pp. 883–884.
Michell, D., *Impotenz durch anithypertensive Therapie?*, Fortschritte der Medizin,. vol. 97, No. 36, pp. 1555, (1979).
Hogan, M. J., et al., *Antihypertensive theraphy and male sexual dysfunction*, Psychosomatics, vol. 21, PT 3, pp. 234–237, (Mar. 1980).
*Drugs that cause sexual dysfunction*, Med. Lett. on Drug& Therapy, vol. 22, No. 25, pp. 108–110, (1980).
Ahmad, S., *Hydralazine and Male Impotence*, Chest, vol. 78, No. 2, pp. 358, (1980).
Wartman, S. A., *Sexual side effects of antihypertensive drugs*, Postgraduate Medicine, vol. 73, No. 2, pp. 133–135 & 138, (1983).
*Drugs that cause sexual dysfunction*, Med. Lett. on Drug& Therapeutics, vol. 25, No. 6411, pp. 73–76, (1983).
Van Arsdalen, K. N., et al., *Drug–induced sexual dysfunction in older men*, Geriatrics, vol. 39, No. 10, pp. 63–67, (1984).
Stevenson, J. G., et al., *Sexual Dysfunction Due to Antihypertensive Agents*, Drug Intelligence and Clinical Pharmacy, vol. 18, pp. 113–121, (1984).
Segraves, R. T., et al., *Erectile Dysfunction Associated with Pharmacological Agents*, Diagnosis and Treatment of Erectile Disturbances: New York: Plenum, pp. 23–63, (1985).
Mockei, J., et al., *Les impuissances medicamenteuses*, Revue Medicale de Bruxelles, vol. 6, No. 6, pp. 418–424, (1985).
Stemon, J., *Les impuissances medicamenteuses*, Contraception Fertilite Sexualite, vol. 14, No. 3, pp. 253–257, (1986).
*Drugs that cause sexual dysfunction*, Med. Lett. on Drugs& Therapeutics, vol. 29, Issue 744, pp. 65–70, (1987).
Wein, A. J., et al., *Drug–induced Male Sexual Dysfunction*, Urologic Clinics of North America, vol. 15, No. 1, pp. 23–31, (1988).
Strauβ, V. B., et al., *Arzneimittelbedingte Hemmungen sexealler Funktionen*, Fortschr. Med., 106, Jg (1988), Nr. 4, S. 61/33–63/37.

Curb, J. D., et al., *Antihypertensive Drug Side Effects in the Hypertension Detection and Follow–up Program, Suppl. II Hypertension*, vol. 11, No. 3, pp. II–51–II–55, (1988).
Lue, T. F., et al., *Pharmacology of Erection and Impotence, Contemporary Management of Impotence and Infertility*, Baltimore, pp. 51–54, (1988).
Galbraith, R. A., *Sexual Side Effects of Drugs, Drug Therapy*, vol. 21, pp. 38–40 & 45, (1991).
Tewari, A., et al., *Hypertension, Antihypertensives and Male Sexual Dysfunctions: A Review, Indian Journal of Urology*, vol. 10, No. 1, pp. 1–6, (1993).
Brock, G. B., et al., *Drug–induced Male Sexual Dysfunction, Drug Safety*, vol. 8, No. 6, pp. 414–426, (1993).
Pray, W. S., *Medications and Sexual Dysfunction, Pharmacist*, vol. 18, No. 8, pp. 27, 28, 30, 32, (1993).
Owen, J. A., et al., *Topical Nitroglycerin: A Potential Treatment for Impotence, Journal of Urology*, vol. 141, pp. 546–548 (1989).
Welti, R. S., et al., *Treatment of Intraoperative Penile Tumescence, Journal of Urology*, vol. 124, pp. 925–926, (1980).
Zentgraf, M., et al., *Diagnosis and Therapy of Erectile Dysfunction Using Papaverine and Phentolamine, Urol. Int.*, vol. 43, pp. 65–75, (1988).
Australian High Court's decision in re *Aktiebolaget Hässlev Alphapham Pty Limited*.
Declaration by Peter Ellis.
Florence, A. T., et al., *Physiochemical Principles of Pharmacy*.
Smith, D. A., et al., *Pharmokinetics and Metabolism in Drug Design*, pp. 35–46, (2001).
Hungarian Documents.
English description of Office Action in P9501933.
Applicants' Response (Apr. 19, 2002).
Israeli Documents.
Declaration of Peter Ellis (Re IL Appln. No. 121836).
Japanese Documents.
Letter Concerning First Office Action in JP Appln. No. 21945/99.
Murray, DN&P 6(3), 150–156 (1993).
*J. Urology*. V. 149, No. 4, 285A (1993).
Impotence/Postgraduate Medicine, v. 93(3), 65–72 (1993).
Dt. Arzteblatt, v. 86, No. 33, C1435–C1437 (1989).
Letter Concerning Sep. 26, 2002 Rejection in JP Appln. No. 21939/99.
English Translation of the Sep. 26, 2002 Rejection.
Japan Patent No. 2920534: (Opposition No. 2000–70281).
Petition (Nov. 28, 2001) (English).
Notification of Reasons for Revocatioan (w/English translation).
Argument (Apr. 18, 2003) (w/English translation).
Request for Correction (Apr. 18, 2003) (w/ English translation).
Withdrawal of Request (Apr. 17, 2003) (w/ English translation).
Decision on Opposition (Jun. 3, 2003) (w/ English translation).
Japan Appln. No. 99/21939.
Reasons for Rejecton w/English summary letter (Oct. 16, 2002).
Notice of Appeal Trial (Dec. 27, 2003) (w/ English translation).
Written Directive for Amendment (Mar. 6, 2003) (w/ English translation).
Dismissal of Appeal Trial (Sep. 8, 2003) (w/ English translation).
Japan Appln. No. 21945/99.
First Official Action (Feb. 28, 2003) w/ English summary letter (Apr. 15, 2003).
Argument (Sep. 1, 2003) w/ English translation.
Opponents' Petition re Pat No. 2925034 (w/ English translation).
EPO Appln. No. 94 916 236.6 Opposition Grounds for Decision (Annex) (Oct. 11, 2001).
EPO Appln. No. 92 916 236.6 Opposition Oral Hearing Minutes (Jul. 16, 2001).
Korean Documents.
English Translation of the Appeal Brief in Case No. 2003 Hu 380 (Mar. 10, 2003).
Thompson, Pharmac. Ther., vol. 51, pp. 13–33 (1991).
Nicholson et al., TIPS, v. 12, 19–27 (Jan. 1991).
English Translation of Answer Brief in Case No. 2003 Hu 380 (Mar. 25, 2003).
English Translation of Brief in Case No. 2001 Heo 1013 (Aug. 16, 2002).
Mikael Ahlstrom, Dissertation dated Jun. 19, 2001.
Slidenafil, CMAJ, 163(9), 1171–1175 (2000).
Original Korean Text and English Translation of KIPO Brief in 2001 Heo 1013 Filed Oct. 16, 2002.
Handbook of Biotechnology Terms 2000, p. 428 (1991).
Manganiello et al., Arch. Biochem. And Biophysics, v. 322, No. 1, pp. 1–13 (1995).
English Translation of KIPO Brief in 2001 Heo 2771 Filed Oct. 16, 2002.
English Translation and Original of Supplemental Brief in 2001 Heo 2771 filed Dec. 18, 2002.
Beavo, Physiological Reviews, v. 75, No. 4, 725–748 (1995).
Teixeira, TIPS, v. 18, 164–170 (May 1997).
Raebum, Int. J. Biochem. Cell Biol., v. 27, No. 1, pp. 29–37 (1995).
Zentgraf et al., Urol. Int., v. 43, 65–75 (1988).
English Translation and Original of Supplemental Brief in 2001 Hei 1013 filed Dec. 18, 2002.
Stroop et al. J. Biol. Chem., v. 266, No. 35, pp. 23802–23809 (1991).
Martins et al., J. Biol. Chem., v. 257, No. 4, pp. 1973–1797 (1982).
Dickenson et al., Biochem J., v. 323, 371–377 (1977).
English Translation and Original of Korean Decision in 2001 Hei 1013.
English Translation and Original of Korean Decision in 2001 Heo 2771.
2001 Heo 1013.
Pfizer Brief (English and Korean) (Mar. 6, 2002).
Exhibits Kap 19–24.
Declaration of Stephen Ballard (Nov. 13, 1998).
KIPO Brief (English and Korean) (Jun. 24, 2002) w/ Exhibits Eul–6–Eul–8.
Rosen et al., J. Sex. Marital Ther. 1993 Fall; 19(3):171–88 (Abstract) (Exh. Eul–9).
KIPO Brief (English and Korean) (Aug. 16, 2002).
Ahlstrom, Disertation (Jun. 19, 2001).
Michelakis et al., CMAJ, 163(9), 1171–1175 (2000).
Pfizer Brief (English and Korean) (Sep. 2002).
Ahlstrom, Dissertation (Jun. 19, 2001).
KIPO Brief (English and Korean) (Oct. 16, 2002) w/ Exh. Eul–10 and Ref. 5.

Pfizer Supp. Brief (English and Korean) (Dec. 2002).
Beavo, *Physiol. Reviews*, v. 65, No. 4, 725–748 (1995).
Stroop et al., J. Biol. Chem., v. 266, No. 35, pp. 23802–23809 (1991).
Martins et al., J. Biol. Chem., v. 257, No. 4, pp. 1973–1979 (1982).
Dickinson et al., Biochem. J., v. 323,371–377 (1997).
Patent Court Decision (English and Korean) (Jan. 10, 2003).
2001 Heo 2771.
Pfizer Rebuttal Brief (English and Korean) (Mar. 2002) w/ Exh. Kap–16 and Kap–17 and Refs. 2 and 3.
KIPO Brief (English and Korean) (Jun. 2002) w/ Refs. 10–16.
Royal Courts of Justice Judgment in Case No. A3/2000/3811 (Jan. 23, 2001).
2001 Heo 2771.
Pfizer Brief (English and Korean) (Jun. 2002) w/ Exh. Kap–18–Kap–61.
Morales, A., et al., *Oral and Topical Treatment of Erectile Dysfunction, Impotence*, vol. 22, No. 4, pp. 879–886 (1995).
Krane, R. .J., et al., *Medical Progress: Impotence, New England Journal of Medicine*, vol. 321, No. 24, pp. 1648–1659, (1989).
Carrier, S., et al., *Pathophysiology of Erectile Dysfunction, Urology*, vol. 42, No. 4, pp. 468–481, (1993).
Holmquist, F., et al., *Actions of 3–Morpholinosydnonimin (Sin–1) on Rabbit Isolated Penile Erectile Tissue, Journal of Urology*, vol. 150, pp. 1310–1315, (1993).
Raifer, J., *This Month in Investigatiave Urology: From the Lab to the Clinic, Journal of Urology*, vol. 159, pp. 1792, (1998).
Whitehead, E. D., et al., *Treatment alternatives for Impotence, Postgraduate Medicine*, vol. 88, No. 2, pp. 139–147 (1990).
Morley, J. E., et al., *Management of Impotence: Diagnostic considerations and therapetuic options, Postgraduate Medicine*, vol. 93, No. 3, (1992).
NIH Consensus Development Panel on Impotence, *Impotence, JAMA*, vol. 270, No. 1, (1993).
Utiger, R. D., et al. *A Pill for Impotence, New England Journal of Medicine*, vol. 338, No. 20, pp. 1458–1459, (1998).
Christensen, S. B., et al., *Chapter 19: Isozyme–Selective Phosphodiesterase Inhibitors as Antiasthmatic Agents, Annual Reports in Medicinal Chemistry*, pp. 188–196, (1994).
Decalaration of Peter Ellis.
2001 Heo 2771.
KIPO Brief (English and Korean) (Aug. 2002).
Exh. Eul–31 w/ English excerpt.
Pfizer Rebuttal Brief (English and Korean) (Aug. 2002) w/ Exh. Kap–63 and Kap–64.
KIPO Brief (English and Korean) (Sep. 24, 2002) w/ Exhibit.
Pfizer Rebuttal Brief (English and Korean) (Sep. 2002) w/ Ref.
Exh. Kap–65 and Kap–66 including English excerpts.
KIPO Brief (English and Korean) (Oct. 2002).
Pfizer Brief (English and Korean) (Dec. 2002).
Beavo, Physiol. Reviews, v. 65, No. 4, 725–748 (1995).
Teixeira et al., Tips, v. 18, pp. 164–170 (May 1997).
Raebum et al., Int. J. Biochem. Cell Biol., v. 27, No. 1, pp. 29–37 (1995).
Zentgraf et al., Urol. Int., 43: 65–75 (1988).

Patent Court Decision (English and Korean) (Jan. 10, 2003).
Pfizer Notice of Appeal (English and Korean) (Jan. 29, 2003).
Pfizer Appeal Brief (English and Korean) (Mar. 10, 2003) w/ Refs. 1–4.
Thompson, Pharmac. Ther., vol. 51,, pp. 13–33 (1991).
Nicholson et al., TIPS, v. 12, 19–27 (Jan. 1991).
KIPO Answer (English and Korean) (Mar. 2003) w/ Ref. 17.
Mexican Documents.
*Pfizer v. Lilly*.
English Translation of the Request for the Administrative Declaration of Infringement Patent No. 195,457 B.
Lilly Response (English).
Response to Office Action (Jul. 29, 2003) (English).
Office Action No. 10709 (Jul. 1, 2003) (English).
*Pfizer v. Bayer*.
English Translation of the Request for the Administrative Declaration of Infringement Patent No. 195,457 B.
Bayer Response (English).
Response to Office Action (Sep. 9, 2003) (English).
Office Action No. 10912 (Jul. 2, 2003) (English).
New Zealand Documents.
*Pfizer v. Lilly* (CP–18–SD/03).
Affidavit of Henry John Brandts–Giesen (Jul. 22, 2003).
Exhibit HBG–1.
Exhibit HGB–2.
Exhibit HBG–3.
Exhibit HBG–4.
Exhibit HBG–5.
Exhibit HBG–6.
Interlocutory Application for More Explicit Statement of Defense to Counterclaim (Jul. 22, 2003).
Deed between PIP and Pfizer Laboratories Ltd.
Exhibit MJG–A.
Exhibit MJG–B.
Exhibit MJG–C.
Exhibit MJG–D.
Exhibit MJG–E.
Exhibit MJG–F.
Exhibit MJG–G.
Statement of Defence by Plaintiff (Jul. 11, 2003).
Notice of Opposition by Plaintiff (Jul. 30, 2003).
*Pfizer v. Bayer* (CP 67–SD/03).
Notice to File More Explicit Defence to Counterclaim (Jul. 25, 2003).
Affidavit of Katrina Lucy Sutich (Aug. 1, 2003).
Interlocutory Application (Aug. 4, 2003).
Notice of Opposition (Aug. 12, 2003).
*Pfizer v. Lilly* (CP 18–SD/03).
Order dated Apr. 16, 2003.
Notice of Proceeding (Jan. 31, 2003).
Statement of Claim (Jan. 30, 2003).
Amended Statement of Claim (Mar. 14, 2003).
Particulars of Breach (Mar. 14, 2003).
Application for Orders (Apr. 16, 2003).
Affidavit of Mark John Gavin (Apr. 16, 2003).
Exhibit MJG–A.
Exhibit MJG–B.
Exhibit MJG–C.
Memorandum of Counsel (Apr. 16, 2003).
Affidavit of Stephen Marcus Stern (Apr. 24, 2003).
Statement of Defense (May 16, 2003).
Particulars of Objection to Validity (May 16, 2003).
*Pfizer v. Bayer* (CP 67–SD/03).

Order dated Apr. 16, 2003.
Particulars of Objection (Feb. 27, 2003).
Notice of Application for Directions (Feb. 27, 2003).
Application for Revocation (Feb. 27, 2003).
Notice of Proceeding (Mar. 14, 2003).
Statement of claim (Mar. 14, 2003).
Particulars of Breach (Mar. 14, 2003).
Notice of Application for Orders (Feb. 27, 2003).
Affidavit of Mark John Gavin (Mar. 17, 2003).
Exhibit MJG–A.
Exhibit MJG–B.
Exhibit MJG–C.
Exhibit MJG–D.
Exhibit MJG–E.
Exhibit MJG–F.
Third Affidavit of Mark John Gavin (Apr. 16, 2003).
Exhibit MJG–A.
Exhibit MJG–B.
Exhibit MJG–C.
Ex Parte Application for Orders (Apr. 16, 2003).
Memorandum of Counsel (Apr. 16, 2003).
Affidavit of Stephen Marcus Stern (Apr. 24, 2003).
Defense and Counterclaim (May 23, 2003).
Statement of Defense by Plaintiff to Counterclaim by First and Second Defendants (Jun. 23, 2003).
Affidavit of Sally Ann Nicolson (Sep. 18, 2003) w/ Exh. SAN 1–5.
Notice of Interlocutory Application for Leave to Amend (Sep. 18, 2003).
Notice of Application to Make Further Submissions (Oct. 2003).
*Pfizer v. Lilly* (CP 18–SD/03).
Second Affidavit of John Brandts–Giesen (Sep. 8, 2003) w/ Exh. HBG 1–5.
Exhibit HBG–1.
Exhibit HBG–2.
Exhibit HBG–3.
Exhibit HBG–4.
Exhibit HBG–5.
Notice of Intention to Amend NZ 266463.
Notice of Intention to Amend NZ 314110.
Notice of Application for Leave to Amend NZ 266463 and NZ 314110 (Sep. 18, 2003).
Notice of Application to Make further Submissions (Oct. 2003).
Affidavit of Sally Ann Nicolson (Sep. 18, 2003).
Exhibit SAN–1.
Exhibit SAN–2.
South African Documents.
*Bayer v. Pfizer* (Patent 94/4018): Application for Revocation (Apr. 17, 2003).
*Lilly v. Pfizer* (Patent 94/4018): Application for Revocation (May 5, 2003).
United States Documents.
*Pfizer v. Lilly* ICOS (No. 02–1561).
Docket Sheet (Oct. 30, 2003).
Complaint (Oct. 22, 2002).
Answer (Jan. 6, 2003).
Pfizer Initial Discolosures (Mar. 21, 2003).
Lilly Initial Disclosures (Mar. 21, 2003).
Pfizer First Interrogatories (Jun. 27, 2003).
Responses to First Interrogatories (Aug. 27 2003).
*Pfizer v. Bayer* (No. 02–1560).
Complaint (Oct. 22, 2002).
Answer of Bayer AG (Jan. 6, 2003).
Answer of SmithKline Beecham (Jan. 6, 2003).
Pfizer Initial Disclosures (Mar. 21, 2003).
Bayer Initial Disclosures (Mar. 21, 2003).
SmithKline Beecham Initial Disclosures (Mar. 21, 2003).
Stipulated Order (Feb. 13, 2003).
Bayer First Interrogatories (Jun. 20, 2003).
Bayer First Requests for Admission (Jun. 20, 2003).
Pfizer First Interrog. To Bayer (Jun. 27, 2003).
Pfizer First Interrog. To SmithKline Beecham (Jun. 27, 2003).
Pfizer Responses to Bayer First Interrog (Jul. 21, 2003).
Pfizer Responses to Bayer First Requests for Admission (Jul. 21, 2003).
Bayer Amended First Interrog. (Aug. 6, 2003).
Pfizer Responses to Bayer Amended First Interrog (Aug. 27, 2003).
Bayer Responses to Pfizer First Interrog. (Aug. 27, 2003).
Pfizer Amended First Interrog. (Aug. 6, 2003).
SmithKline Beecham Responses to Pfizer First Interrog. (Aug. 27, 2003).
*Pfizer v. Bayer AG* (No. 03–888).
Complaint (Sep. 22, 2003).
Answer of Bayer (Oct. 9, 2003).
Answer of SmithKline Beecham (Oct. 10, 2003).
Reply to Counterclaims of Bayer (Oct. 30, 2003).
Reply to Counterclaims of SmithKline Beecham (Oct. 30, 2003).
Taher et al., 149 J. Urol. 285A (Apr. 1993).
Pfizer Submission dated May 16, 2001, Opposition of European Patent No. 0 702 555, Case No. T1212/01–332 (European Patent Office).
Plaintiffs' Responses to Bayer AG and Bayer Corp.'s Amended First Set of Interrrogatories, *Pfizer Inc. v. Bayer AG*, C.A. No. 02–1560, dated Aug. 27, 2003.
de Tejada, Inigo, S., et al., *Impaired Neurogenic and Endothelium–Mediated Relaxation of Penile Smooth Muscle from Diabetic Men with Impotence, The New England Journal of Medicine*, vol. 320, No. 16, pp. 1025–1030, (Apr. 20, 1989).
Affidavit of Robert William Gristwood, dated Oct. 24, 2004, *Eli Lilly & Co. v. Pfizer Research & Development*, Fed. Court of Australia, [2005] FCA 67.
Yoram, V., et al., *Oral Pharmacotherapy in Erectile Dysfunction, Current Opinion in Urology*, vol. 7, pp. 349–353, (1997).
Rajfer, J., *From the Lab to the Clinic, The Journal of Urology*, vol. 159, p. 1792, (1998).
Label for Viagra®, (approved Sep. 19, 2002).
Letter from Molly Hubenschmidt, Dissertation School/Author Relations Dept., Proquest Company, to Sanema Hardrick (Jun. 8, 2005).
UMI Proquest Digital Dissertations—Full Citation & Abstract Margaret Ann Bush, http://wwwlib.umi.com/dissertations/fullcit/9319914.
Transcript of Proceedings, *Eli Lilly & Co. v. Pfizer Research & Development*, Fed. Ct. of Australia, Nov. 15, 2004.
*Eli Lilly & Company v. Pfizer Overseas Pharmaceuticals* [2005] FCA 67, Federal Court of Australia, Order, Feb. 10, 2005.
McCullough, A. R., et al., *Achieving Treatment Optimization with Sildenafil Citrate(Viagra®) in Patients with Erectile Dysfunction, Urology*, vol. 60 (Supplement 28), Aug. 30, 2002.

Declaration Under Rule 37 CFR § 1.132 of Vincent Allen Fiorio, Ph.D., dated Dec. 12, 2003.

Loughney, K., et al., *Isolation and characterization of cDNAs encoding PDE5A, a human cGMP–binding, cGMP–specific 3',5'–cyclic, nucleotide phosphodiesterase*, Gene, vol. 216, pp. 139–147, (1998).

Francis, S. H., et al., *Cycle GMP–Binding Cyclic GMP–specific Phosphodiesterase from Lung, Cyclic Nucleotide Phosphodiesterases: Structure, Regulation and Drug Action*, pp. 117, (1990).

Kruuse, C., et al., *Plasma Levels of cAMP, cGMP and CGRP in sildenafil–induced headche, Cephalagia*, vol. 24, pp. 547–553 (2004).

Wallis, R. M., et al., *Tissue Distribution of Phosphodiesterase Families and the Effects of Sildenafil on Tissue Cyclic Nucleotides, Platelet Function, and the Contractile Responses of Traberculae Cameae and Aoritic Rings in Vitro, The American Journal of Cardiology*, vol. 83 (5A), pp. 3C–12C, Mar. 4, 1999.

Maurice, D. H., et al., *Molecular Basis of the Synergistic Inhibition of Platelet Function by Nitrovasodilators and Activators of Adenylate Cyclase: Inhitition of Cyclic AMP Breakdown by Cyclic GMP, Molecular Pharmacology*, pp. 671–681, (1990).

R. M. Wallis, *The Pharmacology of sildenafil, a novel and selective inhibitor of phosphdiesterase(PDE) type 5, Folia Pharmacology Japan*, vol. 114, pp. 22P–26P, (1999).

Jeremy, J. Y., et al., *Effects of sildenafil, a type–5 cGMP phosphodiesterase inhibitor, and papaverine on cyclic GMP and cyclic AMP levels in the rabbit corpus cavemosum in vitor, British Journal of Urology*, vol. 79, pp. 958–983, (1997).

Hetman, J. M., et al., *Cloning and characterization of two splice variants of human phosphodiesterase 11A, Proceedings Nat'l Acad. Sci.*, vol. 97, No. 23, pp. 12891–12895, (Nov. 7, 2000).

de Tejada, I. S., et al., *The phosphodiesterase inhibotory selectivity and the in vitro and in vivo potency of the new PDE5 inhibitor verdanfil, International Journal of Impotence Research*, vol. 13, pp. 282–290, (2001).

Hoey, M., et al., *Identification and selective inhibition of four distinct soluble forms of cyclic nucleotide phosphodiesterase activity from kidney, Biochemical Pharmacology*, vol. 40, No. 2, pp. 193–202, (1990).

Kruuse, C., et al., *Effects of the non–selective phosphodiesterase inhibitor pentoxifylline on regional cerebral blood flow and large arteries in healthy subjects, European Journal of Neruology*, vol. 7, pp. 629–638, (2000).

Vittone, L., et al., *The mechanical and biochemical effects of pentoxifylline on the perfused rat heart, Experentia*, vol. 36, pp. 1088–1090.

Chen, Y. M., et al., *Pentoxifylline inhibits PDGF–induced Proliferation of and TGF–β–stimulated Collagen Synthesis by Vascular Smooth Muscle Cells, J. Mol. Cell. Cardio.*, vol. 31, pp. 773–783, (1999).

Valente, E. G. A., et al., *L–Arginine and phosphodiesterase(PDE) inhibitors counteract fibrosis in the Peyronie's fibrotic plaque and related fibroblast cultures, Nitric Oxide*, vol. 9, pp. 229–244, (2003).

Declaration Under Rule CFR § 132 of Philip W. Iversen, Ph.D. dated Jul. 1, 2005 (U.S. Patent 6,469,012).

Joint Statement of Dr. Iversen, Dr. Marschner and Mr. Bursalem Concerning Analysis of Florio/Uher Data, Federal Court of Australia, dated Nov. 22, 2004.

Affidavit of Vincent Allen Florio, dated Sep. 27, 2004, *Eli Lilly & Co. v. Pfizer Research & Dev.*, Federal Court of Australia.

Affidavit of Lothar Josef Uher, dated Oct. 20, 2004, *Eli Lilly & Co. v. Pfizer Research & Dev.*, Federal Court of Australia.

Affidavit of Philip W. Iversen, dated Nov. 10, 2004, *Eli Lilly & Co. v. Pfizer Research & Dev.*, Federal Court of Australia.

Affidavit of Ian Colin Marschner, dated Oct. 27, 2004, *Eli Lilly & Co. v. Pfizer Research & Dev.*, Federal Court of Australila.

Mortey, J. E., *Impotence in Older Men, Hospital Practice*, vol. 23, pp. 139–158, (Apr. 15, 1988).

Crowder, J. E., *Efficacy and Safety of Pentoxifylline in Geriatric Patients with Intermittent Claudication, Angiology*, vol. 40, pp. 795–802, (Sep. 1989).

Metz, P., et al., *Penile Blood Pressure, Scand. J. Urol. Nephrol.*, vol. 15, pp. 161–164, (1981).

Korenman, S. G., et al., *Advances in the Understanding and Management of Erectile Dysfunction, J. of Clinical Endocrinology and Metabolism*, vol. 80, No. 7, pp. 1985–1988, (1995).

Korenman, S., G., *New Insights Into Erectile Dysfunction: A Practical Approach, American Journal of Medicine*, vol. 105, pp. 135–144, (Aug. 1998).

Affidavit of Stanley G. Korenman, dated Oct. 2004, *Eli Lilly & Co. v. Pfizer Research & Dev.*, Federal Court of Australia.

Peskircioglu, L., et al., *The role of pentoxifylline in the treatment of erectile dysfunction due to borderline arterial insufficiency, British Journal of Urology*, vol. 77, pp. 563–565.

Request for Ex Parte Reexamination (90/007,614, filed Jul. 5, 2005).

Pfizer Submission dated May 16, 2001, Opposition of European Patent No. 0 702 555, Case No. T1212/01–332 (European Patent Office).

Plaintiffs' Responses to Bayer AG and Bayer Corp.'s Amended First Set of Interrogatories, *Pfizer Inc. v. Bayer AG*, C.A. No. 02–1560, dated Aug. 27, 2003.

de Tajeda, Inigo, S., et al., *Impaired Neurogenic and Endothelium–Mediated Relaxation of Penile Smooth Muscle from Diabetic Men with Impotence, The New England Journal of Medicine*, vol. 320, No. 16, pp. 1025–1030, (Apr. 20, 1989).

Affidavit of Robert William Gristwood, dated Oct. 22, 2004, *Eli Lilly & Co. v. Pfizer Research & Development*, Fed. Court of Australia, [2005] FCA 67.

Yoram, V., et al., *Oral Pharmacotherapy in Erectile Dysfunction, Current Opinion in Urology*, vol. 7, pp. 349–353, (1997).

Rajfer, J., *From the Lab to the Clinic, The Journal of Urology*, vol. 159, p. 1792, (1998).

Label for Viagra®, (approved Sep. 19, 2002).

Letter from Molly Hubenschmidt, Dissertation School/Author Relations Dept., Proquest Company, to Sanema Hardrick (Jun. 8, 2005).

UMI Proquest Digital Dissertations—Full Citation & Abstract Margaret Ann Bush, http://wwwlib.umi.com/dissertation/fullcit/9319914.

Transcript of Proceedings, *Eli Lilly & Co. v. Pfizer Research & Development*, Fed. Ct. of Australia, Nov. 15, 2004.

*Eli Lilly & Company v. Pfizer Overseas Pharmaceuticals* [2005] FCA 67, Federal Court of Australia, Order, Feb. 10, 2005.

McCullough, A. R., et al., *Achieving Treatment Optimization wiht Sildenafil Citrate(Viagra®) in Patients with Erectile Dysfunction*, Urology, vol. 60, (Supplement 2B), Aug. 30, 2002.

Declaration Under Rule 37 CFR § 1.132 of Vincent Allen Florio, Ph.D., dated Dec. 12, 2003.

Loughney, K., et al., *Isolation and characterization of cDNAs encoding PDE5A, a human cGMP–binding, cGMP–specific 3', 5'–cyclic nucleotide phosphodiesterase*, Gene, vol. 216, pp. 139–147, (1998).

Francis, S. H., et al., *Cyclic GMP–Binding Cyclic GMP–specific Phosphodiesterase from Lung. Cyclic Nucleotide Phosphodiesterases: Structure, Regulation and Drug Action*, pp. 117, (1990).

Kruuse, C., et al., *Plasma Levels of cAMP, cGMP and CGRP in sildenafil–induced headache*, Cephalalgia, vol. 24, pp. 547–553, (2004).

Wallis, R. M., et al., *Tissue Distribution of Phosphodiesterase Families and the Effects of Sildenafil on Tissue Cyclic Nucleotides, Platelet Function, and the Contractile Response of Trabeculae Carneae and Aortic Rings in Vitro*, The American Journal of Cardiology, vol. 83 (5A), pp. 3C–12C, Mar. 4, 1999.

Maurice, D. H., et al., *Molecular Basis of the Synergistic Inhibition of Platelet Function by Nitrovasodilators and Activators of Adenylate Cyclase: Inhibition of Cyclic AMP Breackdown by Cyclic GMP*, Molecular Pharmacology, pp. 671–681, (1990).

R. M. Wallis, *The Pharmacology of sildenafil, a novel and selective inhibitor of phosphodiesterase(PDE) type 5*, Folia Pharmacology Japan, vol. 114, pp. 22P–26P, (1999).

Jeremy, J. Y., et al., *Effects of sildenafil, a type 5 cGMP phosphodiesterase inhibitor, and papaverine on cyclic GMP and cyclic AMP levels in the rabbit corpus cavemosum in vitro*, British Journal of Urology, vol. 79, pp. 958–963, (1997).

Hetman, J. M., et al., *Cloning and characterization of two splice variants of human phosphodiesterase 11A*, Proceedings Nat'l Acad. Sci., vol. 97, No. 23, pp. 12891–12895, (Nov. 7, 2000).

de Tejada, I. S. et al., *The phosphodiesterase inhibitory selectivity and the in vitro and in vivo potency of the new PDE5 inhibitor vardanafil*, International Journal of Impotence Research, vol. 13, pp. 282–290, (2001).

Hoey, M., et al., *Identification and selective inhibition of four distinct soluble forms of cyclic nucleotide phosphodiesterase activity from kidney*, Biochemical Pharmacology, vol. 40, No. 2, pp. 193–202, (1990).

Kruuse, C., et al., *Effects of the non–selective phosphodiesterase inhibitor pentoxifylline on regional cerebral blood flow and large arteries in healthy subjects*, European Jouranl of Neruology, vol. 7, pp. 629–638, (2000).

Vittone, L., et al., *The mechanical and biochemical effects of pentoxifylline on the perfused rat heart*, Experentia, vol. 36, pp. 1088–1090, (1980).

Chen, Y. M., et al., *Pentoxifylline Inhibits PDGF–induced Proliferation of and TGF–β–stimulated Collagen Synthesis by Vascular Smooth Muscle Cells*, J. Mol. Cell. Cardiol., vol. 31, pp. 773–783, (1999).

Valente, E. G. A., et al., *L–Arginine and phosphodiesterase(PDE) inhibitors counteract fibrosis in the Peyronie's fibrotic plaque and related fibroblast cultures*, Nitric Oxide, vol. 9, pp. 229–244, (2003).

Declaration Under Rule 37 CFR §1.132 of Philip W. Iversen, Ph.D. dated Jul. 1, 2005 (U.S. Patent 6,469,012).

Joint Statement of Dr. Iversen, Dr. Marschner and Mr. Burselem Concerning Analysis of Florio/Uher Data, Federal Court of Australia, dated Nov. 22, 2004.

Affidavit of Vincent Allen Florio, dated Sep. 27, 2004, *Eli Lilly & Co. v. Pfizer Research & Dev.*, Federal Court of Australia.

Affidavit of Luthar Josef Uher, dated Oct. 20, 2004, *Eli Lilly & Co. v. Pfizer Research & Dev.*, Federal Court of Australia.

Affidavit of Philip W. Iversen, dated Nov. 10, 2004, *Eli Lilly & Co. v. Pfizer Research & Dev.*, Federal Court of Australia.

Affidavit of Ian Colin Marschner, dated Oct. 27, 2004, *Eli Lilly & Co. v. Pfizer Research & Dev.*, Federal Court of Australia.

Morley, J. E., *Impotence in Older Men*, Hospital Practice, vol. 23, pp. 139–158, (Apr. 15, 1988).

Crowder, J. E., *Efficacy and Safety of Pentoxifylline in Geriatric Patients with Intermittent Claudication*, Angiology, vol. 40, pp. 795–802 (Sep. 1989).

Metz, P., et al., *Penile Blood Pressure*, Scand. J. Urol. Nephrol., vol. 15, pp. 161–164, (1981).

Korenman, S. G., et al., *Advances in the Understanding and Management of Erectile Dysfunction*, J. of Clinical Endocrinology and Metabolism, vol. 80, No. 7, pp. 1985–1988, (1995).

Korenman, S., G., *New Insights into Erectile Dysfunction: A Practical Approach*, American Journal of Medicine, vol. 105, pp. 135–144, (Aug. 1998).

Affidavit of Stanley G. Korenman, dated Oct. 2004, *Eli Lilly & Co. v. Pfizer Research & Dev.*, Federal Court of Australia.

Peskicioglu, L., et al., *The role of pentoxifylline in the treatment of erectile dysfunction due to borderline arterial insufficiency*, British Journal of Urology, vol. 77, pp. 563–565 (1996).

Request for Ex Parte Reexamination (90/007,614, filed Jul. 5, 2005).

China—Appeals to and Response to Admin. Judgment Yizhongchuzi No. 884 (2004).

Baiyunshan Petition of Appeal in Chinese and English.
Baiyunshan Response to Appeal in Chinese and English.
Haiguang Petition of Appeal in Chinese and English.
Haiguang Response to Appeal in Chinese and English.
Hefeiyigong Petition of Appeal in Chinese and English.
Hefeiyigong Response to Appeal in Chinese and English.
Huayu Petition of Appeal in Chinese and English.
Huayu Response to Appeal in Chinese and English.
Jilin Petition of Appeal in Chinese and English.
Jilin Response to Appeal in Chinese and English.
Kang'erwei Petition of Appeal in Chinese and English.
Kang'erwei Response to Appeal in Chinese and English.
Lianxiang Petition of Apeal in Chinese and English.
Lianxing Response to Appeal in Chinese and English.
Tianpu Petition of Appeal in Chinese and English.
Tianpu Response to Appeal in Chinese and English.
Yabang Petition of Appeal in Chinese and English.
Yabang Response to Appeal in Chinese and English.
Hangtaomao Petition of Appeal in Chinese and English.
Hangtaomao Response to Appeal in Chinese and English.

Brazil—*Bayer S. A.* vs. *Pfizer LTD* Nullity Action 2003.61.00.010308–3 (English Language Translations).
●Judgment Apr. 11, 2006.
●Appeal May 12, 2006.
●Appellate Review Jun. 12, 2006.

●Preliminary Injunction Jun. 12, 2006.
●Legal Opinion May 15, 2006.
Brazil.
*Bayer S.A.* v. *Pfizer Ltd.* Nullity Action—Case No. 2006.03.00.049987–0.
1. Order on Precautionary Measure, Feb. 28, 2007.
2. Motion on Service of Process, Jan. 8, 2007.
3. Vote–Examination (re: contested foreign judgment).
Appeal of Chinese Opposition Administrative Judgment (2004) Yizhongchuzi No. 884.
Submission by Defendant PRB (with English language translation).
Pfizer Response to PRB Submission (with English language translation).
Submission by Third Party pan Huaping (with English language translation).
Pfizer Response to Pan Huaping Submission (with English language translation).
*New Zealand Pfizer* v. *Lilly* CIV–2003–404–452 Lilly Evidence.
Attachments to Affidavit of Jason Paul Rogers.
● A–Priority Documents PCT/EP94/01580.
● B–WO 94/20902.
● C–International Preliminary Examination Report PCT/EP94/01580.
● D1–Form 43 to New Zealand.
● D2–Acknowledgement letter from New Zealand for Form 43.
● D3–New Zealand acceptance of Form 43.
● D4–New Zealand response to official letter dated Mar. 14, 1996.
● D5–New Zealand reply to applicant's letter of Nov. 15, 1996.
● D6–New Zealand letter referring to official letter dated Nov. 19, 1996.
● D7–New Zealand letter of receipt for applicant letter of Jan. 23, 1997.
● D8–New Zealand letter of receipt of official letter dated Jan. 24, 1997.
● D9–New Zealand letter of receipt of applicants letter of Jan. 29, 1997.
● D10–New Zealand Notice of Acceptance of Complete Specification.
● D11–New Zealand Request for the Sealing of a Patent.
● D12–New Zealand Register of Patents.
● E–New Zealand Complete Specification.
● F1–New Zealand Complete Specification.
● F2–New Zealand outstanding matters.
● F3–New Zealand response to official letter of Jan. 27, 1997.
● F4–New Zealand Examination Report.
● F5–New Zealand referring to official letter dated Nov. 20, 2000.
● F6–Notice of Acceptance of Complete Specification.
● G–New Zealand Complete Specification.
● JR1.
● JR2–New Zealand enclosing Patents Form 43.
● JR3–PCT Notification Concerning Document Transmitted.
● JR4–New Zealand Patent Office Journal, Office Practice Note.
● JR5–Guidelines on Applications Relating to the Medical Treatment of Humans.
● JR6–New Zealand Notice of Interlocutory Application by Plaintiff.
● JR7–New Zealand Patent Office Journal, "Swiss" Type Patent Claims.
● JR8–New Zealand Patent Office Journal, Industrial Exhibition Design NZ '97.
Affidavit of Glenis Hogg.
Affidavit of Jason Paul Rogers.
Affidavit of Mignon Elaine Margaret Pickwell.
Statement of Carl David Burgess.
Statement of John E Morley.
Statement of John Pryor.
Statement of Robert William Gristwood.
Statement of Ross Ashley Cartmill.
Statement of Timothy James Bromley Maling.
Statement of William Nell Charman.
Witness Statement of Margaret Anne Brimble.
Affidavit of Jason Paul Rogers (2).
Affiidavit of Mignon Elaine Margaret Pickwell (2).
Affidavit of Susan Margaret Gotts Foggin.
*Pfizer Ireland Pharmaceuticals & Anor* v *Eli Lilly and Company* Index Common Bundle of Docs.
Statement of Evidence of Ian George Tucker.
Statement of John E. Morley (2).
Statement of Lawrence Ivan Kruse.
Statement of Robin Fred Smart.
Statement of Sheila Anne Doggrell.
Statement of William Alexander Denny.
Supplementary Statement of Sheila Anne Doggrell.
*China* v. *Pfizer Ireland* (2004) Yizhongchuzi No. 884 court decision by Beijing No. 1 Intermediate People's Court and its English translation.
*Lilly* v. *Pfizer* (V604 of 2002) / *Bayer* v. *Pfizer* (V111 of 2002) (Austraila Court Documents).
Brazillan Documents.
Lawsuit #2004.001.042.744–9.
Appeal, Jul. 14, 2004.
Reply to the Plaintiffs' appeal, Aug. 10, 2005.
Judgment, Jun. 14, 2005.
Appeal No. 2005.001.32621 and 2005.001.32885.
Brief of the Appellants, Sep. 30, 2005.
Special Appeal, Nov. 3, 2005.
Report, Sep. 26, 2005.
Lawsuit #2003.001.034974–5.
Appeal, Jul. 14, 2004.
Reply to the Plaintiffs' appeal, Aug. 10, 2005.
Declaratory Action, Mar. 7, 2005.
Case No. 2003.61.00.010308–3.
Nullity Action, Jan. 12, 2005.
Case No. 911.
Homologation of a Foreign Ruling, Mar. 21, 2005.
Legal Opinion No. 887/ILCC.
Opinion in favor of Homologation, Nov. 24, 2005.
Publications.
The Diabetes Monitor, Combination of herbal products with prescription medications, www.diabetesmonitor.com/z09.htm, Jun. 15, 2005.
Lien, E. J., et al. *Recent Development of Herbal Medicine in USA: A Survey, J. Chin. Med.*, vol. 9 No. 3, pp. 171–183, 1998.
Wu, H., et al., *SAR Analysis of Phytoandrogenic Compounds in Traditional Medicines, International Journal of Oriental Medicine*, vol. 28, No. 1, pp. 13–34, Jun. 2003.

Mahady, G. B., *Recent Advances on the Nutritional Effects Associated with the Use of Garlic as a Supplement*, American Society for Nutritional Sciences, pp. 1120S–1123S, 2001.

Rajfer, J., et al., *Case Report: Avoidance of Palpable Corporal Fibrosis Due to Priapism with Upregulators of Nitric Oxide*, J. Sex Med., pp. 1–4, 2005.

Tian, L, et al., *Effects of icarün on intracavernosal pressure and systematic arterial blood pressure of rat*, www.ncbi.nt-m.nih.gov/entrez/query.fcgi?cmd=Retrieve&db=pubmed&dopt=Abstra..., Sep. 29, 2005 (abstract).

Tian, L, et al., *Effects of icarün on the erectile function and expression of nitrogen oxide synthase isoforms in corpus cavernosum of arterigenic erectile dysfunction rat model*, www.ncbi.nlm.nih.gov/entrez/query.fcgi?cmd=Retrieve&db=pubmed&dopt=Abstra..., Sep. 29, 2005 (abstract).

Xin, Z. C., *Effects of Icarün on cGMP–specific PDE5 and cAMP–specific PDE4 activities*, www.asiaandro.com/1008–682/5/15.htm, Nov. 23, 2005.

Chai, Y., et al., *Determination of icarün in Chinese traditional by capillary zone electrophoresis*, Biomedical Chromatography, vol. 13, pp. 373–375, (1999).

Zhangwan, L, et al., *Determination of the Content of icarüne in Four Chinese Patent Medicines Containing Epimedium brevicornum Maxim*, J. WCUMS, vol. 26, No. 1, pp. 70–73 (1995) (with English language abstract).

Yamada, Y., et al., *Receptor occupancy theory–based analysis of antiematic effects and standard doses of 5–$HT_3$ receptor antagonists in cancer patients*, Cancer Chemother Pharmacol, vol. 54, pp. 185–190, (2004).

Smith, D. A. et al., *Pharmacokinetics and Metabolism in Drug Design; Methods and Principles in Medicinal Chemistry*, vol. 13, pp. 24–29, (2001).

Uka, Y., et al., *Pharmacocinetics of icariin in rats*, Chin. Pharm J., vol. 34, No. 1, (1999), (English language abstract).

Kung, S. S., et al. *Flavonoid Glycoside*, Kor. J. Pharmacogn., vol. 22 No. 2., pp. 85–90 (1991), (with English language abstract).

Kim, H. K., et al., *Isolation and Quantitative Analysis of Icariin from Epimedil Herba*, Kor. J. Phamacogn, vol. 32, No. 1, pp. 43–48 (2001). (with English language abstract).

Huang, K., C., *The Pharmacology of Chinese Herbs*, $2^{nd}$ edition, pp. 2–14, (1999).

Xu, L.L. et al., *HPLC analysis of icariine of haiba epimebil in different variety and different planting areas*, Chinese Journal of Modern Applied Pharmacy, vol. 17, No. 2, pp. 114, (2000) (with English language abstract).

Liang, et al., *Journal of Shanghai Medical University*, vol. 27, No. 3, pp. 185–186, (2000).

Remington: *The Science and Practice of Pharmacy*, p. 431 (1995).

Huntley, et al., *Herbal Medicines for asthma: a systematic review*, Thorax, vol. 55, pp. 925–929, (2000).

Guo, B.L., *Determination of 9 Flavonoids in 5 species of Epimedium recorded in Chinese Pharmacoposis by HPLC*, Acta Pharmaceutica Sinica, vol. 31, No. 4, pp. 292–295, (1996).

*Pfizer Limited* v. *Eli Lilly* Bill of Review Case #754,177 (Brazil).

Instruction dated Aug. 21, 2006.

Brief of Appellant Nov. 8, 2006.

*Pfizer Limited* v. *Eli Lilly* Bill of Review Case #754.178 (Brazil).

*Lilly ICOS LLC* v. *Pfizer Limited* Contested Foreign Ruling Case #7921 (Brazil).

Respondent's Memorial Sep. 4, 2006.

*Bayer S. A. and Bayer Aktiengesellschaft* v. *Pfizer Limited* Nullity Action Case # 2003.61.00.010308–3. (Brazil).

Nullity Action Aug. 31, 2006.

Nullity Action, misc. documents, Aug. 9, 2006.

*Pfizer Limited* v. *Bayer S. A.* Provisional Measure Case #2006.3.04987–0 (Brazil).

Reply Aug. 25, 2006.

Verbal pleading; Report; Digest Sep. 25, 2006.

Beavo, J., Multiple Phosphodiesterase Isoenzymes: Background, Nomenclature and Implications, in Cyclic Nucleotide Phosphodiesterases: Structure, Regulation and Drug Action 3–15 (J. Beavo & M. Houslay, eds., 1990).

Bowman, A. & Drummond A.H., Cyclic GMP Mediates Neurogenic Relaxation in the Bovine Retractor Penis Muscle, Brit. J. Pharmac. 81:665–74 (1984).

Bush, M.A., The Role of the L–Arginine–Nitric Oxide–Cyclic GMP Pathway in Relaxation of Corpus Cavernosum Smooth Muscle (1993) (Ph.D. dissertation, University of California).

Bush, P.A., et al., Nitric Oxide is a Potent Relaxant of Human and Rabbit Corpus Cavemosum, J. Urology 147:1650–55 (1992).

Georgitis, W.J. & Merenich, J. A., Trial of Pentoxifylline for Diabetic Impotence, Diabetes Care 18:345–52 (1995).

Knoll, L.D., et al., A Randomized Crossover Study Using Yohimbine and Isoxsuprine Versus Pentoxifylline in the Management of Vasculogenic Impotence, J. Urology 155:144–46 (1996).

Korenman, S.G. & Viosca, S.P., Treatment of Vasculogenic Sexual Dysfunction with Pentoxyifylline, J. Am. Geriatrics Soc. 71:363–66 (1993).

Moncada, S., et al., Nitric Oxide: Physiology, Pathophysiology, and Pharmacology, Pharm. Revs. 43:109–42 (1991).

Murray, K.J., Phosphodiesterase $V_a$ Inhibitors, Drug News & Perspectives 6:150–56 (1993).

NIH Consensus Panel on Impotence, NIH Consensus Conference: Impotence, JAMA 270:83–90 (1993).

Physicians' Desk Reference 1125–26 (47th ed. 1993).

Rajfer, J., et al., Nitric Oxide as a Mediator of Relaxation of the Corpus Cavernosum in Response to Nonadrenergic, Noncholinergic Neurotransmission, New England J. Med. 326:90–94 (1992).

Silver, P.J., et al., Cyclic GMP Potentiation by WIN 58237, a Novel Cyclic Nucleotide Phosphodiesterase Inhibitor, J. Pharm. Experimental Therapeutics 271:1143–49 (1994).

Taher, A., et al., Phosphodiesterase Activity in Human Cavernous Tissue and the Effect of Various Selective Inhibitors, J. Urology 149:285A (1993).

Thompson, W.J., Cyclic Nucleotide Phosphodiesterases: Pharmacology, Biochemistry and Function, Pharm. Therapy 51:13–33 (1991).

Weiss, R.J., Effects of Antihypertiensive Agents on Sexual Function, Amer. Family Physician 44:2075–80 (1991).

Advisory Action, paper #21, Apr. 22, 1998.

Amendment Under Rule 111; paper #9, Apr. 4, 1997.

Amendment, paper #54, Dec. 21, 2001.

Brief for Appellants Under 37 C.F.R. § 1.192(a), paper 190 23, Aug. 4, 1998.

Decision of the Board of Patent Appeals and Interferences, Appeal No. 2000–1370, paper #39, Nov. 29, 2000.
Examiner's Answer, paper #25, Nov. 5, 1998.
Handwritten Note from Ringrose, on copy of Rajfer.
Pfizer Memorandum from N. K. Terrett, May 26, 1993 (PFZ00170659).
Pfizer Memorandum from Steve Ballard, Minutes of Impotence Meeting, Nov. 4, 1994 (PFZ00037332–37).
Pfizer Memorandum from Steve Ballard, Minutes of Impotence Meeting, Jan. 20, 1995 (PFZ00029119–25).
Office Action, paper #5, Oct. 9, 1996.
Office Action, paper #11, Aug. 12, 1997.
Office Action, paper #50, Aug. 29, 2001.
Plaintiff's Responses to Bayer AG and Bayer Corp.'s Amended First Set of Interrogatories, *Pfizer, Inc.*, v. *Bayer AG, et al.*, Civil Action 02–1560 JJF (D. Del.).
Preliminary Amendment to Reduce the Filing Fee, paper #5A, Dec. 5, 1995.
Response After Final Rejection, paper #17, Feb. 9, 1998.
Mar. 28, 2000 Witness Statement of Julianna Jenkins.
Aug. 22, 2000 Witness Statement of Peter Ellis.
Sep. 18, 2000 Second Expert Report of Dr. Robert William Gristwood.
May 16, 2001 Proprietors' [Pfizer's] Response to EPO.
Appellants' Reply Brief Under 37 C.F.R. § 1.193(B)(1), paper #27, Jan. 4, 1999.
Request for Ex–parte re–examination of US 6,469,012 (Dec. 15, 2003).
Beavo, J., *Multiple Phosphodlesterase Isoenzymes: Background, Nomenclature and Implications, Cyclic Nucleotide Phosphodiesterases: Structure, Regulation and Drug Action*, pp. 3–15, J. Beavo and M. D. Houslay, eds., (1990).
Georgitis, W. J., et al., *Trial of Pentoxifylline for Diabetic Impotence, Diabetes Care*, vol. 18, No. 3, pp. 345–352, (1995).
Knoll, L. D., et al., *A Randomized Crossover Study Using Yohimbine and Isoxsuprine Versus Pentoxifylline in the Management of Vasculogenic Impotence, Journal of Urology*, vol. 155, pp. 144–146, (1996).
*Physicians' Desk Reference*, pp. 1125–1126, 47$^{th}$ edition, (1993).
Silver, P. J., *Cyclic GMP Potentiation by WIN 58237, a Novel Cyclic Nucleotide Phosphodiesterase Inhibitor, J. of Pharmacology and Experimental Therapeutics*, vol. 271, No. 3, pp. 1143–1149, (1994).
Weiss, R. J., et al., *Effects of Antihypertensive Agents on Sexual Function, Amer. Family Physician*, vol. 44, No. 6, pp. 2075–2080, (1991).
Rajfer, et al. article with handwritten notes.
Pfizer Memorandum from N. K. Terrett, May 26, 1993.
Pfizer Memorandum from Steve Ballard, Minutes of Impotence Meeting Nov. 4, 1994.
Pfizer Memorandum from Steve Ballard, Minutes of Impotence Meeting Jan. 20, 1995.
Canadian Documents.
*Bayer* v. *Pfizer* (T865–02):
Order (Nov. 24, 2003).
MacOdrum letter to court (Nov. 18, 2003).
*Lilly* v. *Pfizer* (T–341–02):
Order (Aug. 13, 2003).
*Pfizer* v. *Lilly* (T–1721–03):
Order (Nov. 3, 2003).
Reasons for Oder (Nov. 3, 2003).
Statement of Defence and Counterclaim (Nov. 3, 2003).
Order (Nov. 20, 2003).
Chinese Documents.
Patent No. 94192386.X:
Statement of Nicholas Kenneth Terrett (Oct. 23, 2002).
Statement of Nicholas Kenneth Terrett (Mar. 7, 2000).
Statement of Mitradev Boolell (Oct. 23, 2002).
Statement of Mitradev Boolell (Mar. 18, 2000).
Colombian Documents.
File 6608:
Correspondence to Court (Feb. 14, 2002) (English).
Letters Rogatory Nos. 032–035 (English).
Answer to Allegations (Feb. 5, 2001) (English).
Evidentiary Order (Jul. 10, 2001) (English).
Various pleadings and orders (English).
Various pleadings and orders (English).
New Zealand Documents.
*Pfizer* v. *Lilly* (CIV 2003–404–452):
Answer to Particulars of Objection (Dec. 19, 2003).
Judgment of Potter J as to Costs on Defendants' Interlocutory Application that the Plainfiff File a More Explicit Statement of Defence to Counterclaim (Dec. 18, 2003).
*Pfizer* v. *Bayer* (CIV 2003–404–506):
Answer to Particulars of Objection (Dec. 19, 2003).
Murray, "Phosphodiesterase $V_A$ Inhibitors", DN&P 6(3), Apr. 1993.
USPTO "Revised Guidelines for Usage of Previously Cited/Considered Prior Art in Reexamination Proceedings", Jul. 1, 2003.
*In re European Patent (UK) No. 0,702,555*, Patents Court Case No. HC 1999 No. 01110 (Nov. 8, 2000) (the Laddie Opinion).
Ignarro et al., *Endothelium Derived Relaxing Factor Produced and Released from Artery and Vein is Nitric Oxide*, Pro. Natl. Acad. Sci., 84, 9265–9269, 1987.
Gruetter et al., *Relationship Between Cyclic GMP Formation and Relaxation of Coronary Arterial Smooth Muscle by Glycerol Trinitrate, Nitroprusside, Nitrite and Nitric Oxide: Effects of Methylene Blue and Methemoglibin*, J. Pharmacol. Exp.Ter., 219, 181–186, 1981.
Thompson et al., *Purification and Characterization of High Affinity Cyclic Adenosine Monophosphate from Dog Kidney*, J. Biochem., 23, 5228–5237, 1979.
Thompson, *Cyclic Nucleotide Phosphodiesterases: Pharmacology, Biochemistry and Function*, Pharmcol. Ther., 51, 13–33. 1991.
Butcher et al., *Purification and Properties of Cyclic 3', 5'–Nucleotide Phosphodiesterase and Use of This Enzyme to Characterize Adenosine 3', 5'–Phosphate in Human Urine*, J. Biolog. Chem., 237, 1244–1250, 1962.
Remington's Pharmaceutical Sciences, 18$^{th}$ Edition (1990).
Bowman et al., *Cyclic GMP Mediates Neurogenic Relaxation in the Bovine Retractor Penis Muscle*, Br. J. PHarmacol., 81, 665–674, 1984.
Brindley, *Pilot Experiments on the Actions of Drugs Injected Into the Human Corpus Cavernosum Penis*, Br. J. Pharmacol., 87, 495–500, 1986.
Seftel et al., *Classification of Male Sexual Dysfunction*, Problems in Urology 5(4), 496–509, 1991.
Goldstein, *Vasculogenic Impotence, Its Diagnosis and Treatment*, Problems in Urology, 1(3), 547–563, 1987.
Virag et al., *Is Impotence an Arterial Disorder?* The Lancet 181–184, 1985.

Morales et al., *Oral and Transcutaneous Pharmaclogic Agents in the Treatment of Impotence*, Urol. Clin. N. Am., 15(1), 87–93, 1988.

Korenman et al., *Treatment of Vasculogenic Sexual Dysfunction with Pentoxifylline*, J. Am. Geriatrics, 41(4), 363–366, 1993.

Raifer et al., *Nitric Oxide as a Mediator of Relaxation of the Corpus Cavernosum in Response to Nonadrenergic, Noncholinergic Neurotransmission*, N. Engl. J. Med., 326, 90–94, 1992.

Expert Report of Dr. Louis Ignarro, UK High Court of Justice (Aug. 21, 2000).

Silver et al., *Cyclic GMP Potentiation by WIN 58,237, A Novel Cyclic Nucleotide Phosphodiesterase Inhibitor*, J. Pharmacol. & Exp. Ther., 271, 1143–1149, 1994.

Tigo–Rocha et al., *Nitric Oxide and cGMP:Mediators of Pelvic Nerve–Stimulated Erection in Dogs*, Am.J.Physiol., 264, F419–H422, 1993.

Taher et al., *Phosphodiesterase Activity in Human Cavernous Tissue and the Effect of Various Selective Inhibitors*, J. Urol., Am. Urol. Assn. Rpt. 285, 1993.

Bush, "The Role of the L–Arginine–Nitric Oxide–Cyclic GMP Pathway in Relaxation of Corpus Cavernosum Smooth Muscle," 159–160, (May 13, 1994).

Second Declaration of Dr. Stephen Ballard Under 37 CFR 1.132 (Feb. 6, 1998).

Ringrose Notations on Rajfer N. Engl. J. Med.

Pfizer's Owner's Statement in Response to the Director's Order for Reexamination (Nov. 26, 2003).

Pfizer's Response to Bayer's Amended First Set of Interrogatories (Jul. 21, 2003).

European Patent Office Appeal Declaration of Peter Ellis (Jul. 21, 2003).

Ignarro et al., *Association Between Cyclic GMP Accumulation and Acetylcholine–elicited Relaxation of Bovine Intrapulmonary Artery*, J. Pharmacol: Exp. Ther., 228, 682–690, 1984.

Pfizer's Response Writ in European Patent Office Appeal (Jul. 24, 2003).

Rudd et al., *Inhibition of Exercised–Induced Asthma by an Orally Absorbed Mast Cell Stabilizer (M&B 22948 Zaprinast)*, J. Brit. Dis. Chest, 77, 78–86, 1983.

Reiser et al., *The Effect of Zaprinast (M&B 22948, An Orally Absorbed Mast Cell Stabilizer) on Exercised–Induced Asthma in Children*, J. Brit. Dis. Chest, 80, 157–163, 1986.

Declaration of Robert W. Gristwood in re Ex Parte Reexamination of USPN 6,469,012.

Pfizer Memorandum "UK–92, 480– Information Required for Analysts Presentation in October" (Sep. 2, 1994).

File Wrapper for United States Patent No. 5,426,107.

Director's Order for Reexamination (Sep. 29, 2003).

Viagra: The Remarkable Story of Discovery and Launch (2001).

Witness Statement of Peter Ellis in the Matter of European Patent (UK) No. 0,702,555 (Aug. 22, 2000).

Yaman et al., *Effect of Sildenafil on Nocturnal Erections of Potent Men*, Int'l J. Impot. Res., 15, 117–121, 2003.

Aversa et al., *Effects of Sildenafil (Viagra) Administration on Seminal Parameters and Post–Ejaculatory Refractory Time in Normal Males*, Human Reproduction, 15(1), 131–134, 2000.

Burchardt et al., *Hypertension is Associated with Severe Erectile Dysfunction*, J. Urol., 164, 1188–1191, 2000.

Lilly ICOS Request for Rexamination.

Examiner's Order Granting Request of Ex Parte Reexamination (Feb. 9, 2004).

Letter re Clarification of Record (Mar. 5, 2004).

First Declaration of Dr. Stephen Ballard under 37 CFR 1.132 (Feb. 6, 1998).

Third Declaration of Dr. Stephen Ballard under 37 CFR 1.132 (Feb. 6, 1998).

Written Argument for JP Application Hei–6 (1994)–506786 (Dec. 3, 1996).

Rfizer's Response After Final Rejection (Feb. 9, 1998).

U.K. Expert Report of Robert Allen John Challiss (Aug. 22, 2000).

Terrett Memorandum to UK 94,480 ECMT re Patent Filing for cGMP PHEIs in Impotence dated May 6, 1993 (PFZ00170659).

Respondent's Notice of Experiments, Declaration of Dr. Stephen Ballard (Oct. 29, 1999).

Korenman, *Treatment of Vasculogenic Sexual Dysfunction with Pentoxifylline*, Clinical Res., 36(1), 123A, 1988.

Allenby et al., *Pentoxifylline in the Treatment of Vascular Impotence*, Angiology, 42, 418–420, 1991.

Morley, *Management of Impotence: Diagnostic Considerations and Therapeutic Options*, Postgraduate Med. 93(3) 65–72, 1993.

Leriche, *Des Obliterations Arterielles Hautes Comme Cause D'Une Insuffiscance Circulatoire Des Membres Inferieurs*, Soc. Chrirurgie 49, 1404–1406, 1923.

English Translation of Leriche, *Des Obliterations Arterielles Hautes Comme Cause D'Une Insuffiscance Circulatoire Des Membres Inferieurs*, So. Chrirurgie 49, 1401–1406, 1923.

Goldstein et al., *Diagnosis and Therapy of Erectile Dysfunction*, Campbell's Urology, $6^{th}$ ed., ch. 84, 3033–3070, 1993.

EPO Declaration of Dr. John Morley (Mar. 5, 2001).

Order on Precautionary Measure, Feb. 28, 2007.

Motion on Service of Process, Jan. 8, 2007.

Vote–Examination (re: contested foreign judgment).

Submission by Defendant PRB (with English language translation).

Pfizer Response to PRB Submission (with English language translation).

Submission by Third Party Pan Huaping (with English language translation).

Pfizer Response to Pan Huaping Submission (with English language translation).

*Pfizer Ltd. vs. Eli Lilly* (Inhibitory Action Case No. 315.955.4) vol. II: Bill of Review Against Redistribution (English).

*Lilly Icos v. Pfizer Ltd.* (Homologation of a Foreign Ruling Case No. 7921) vol. VI (English).

*Eli Lilly v. Pfizer Ltd.* (Declaratory Action Case No. 2003.001.034974–6) vol. VII (English).

*Pfizer Ltd. v. Bayer* (Inhibitory Action Case No. 2003.03.040625–0) vol. XIII (English).

*Bayer v. Pfizer Ltd.* (Nullity Action Case No. 2003.61.00.010308–3) vol. IX (English).

*Bayer v. Pfizer Ltd.* (Nullity Action Case No. 2003.61.00.010308–3) vol. X (English).

*Bayer v. Pfizer Ltd.* (Nullity Action Case No. 2003.61.00.010308–3) vol. XI (English).

Canada.

*Pfizer v. Lilly* (Case No. T–1721–03).

Pfizer Motion Record Motion for Interlocutory Injunction (vols. 3–5,7, 8) (Jan. 16, 2004).

Defendant's responding Motion Record (vols. 1–3) (Dec. 15, 2003).
Pfizer Motion to Strike Counterclaim Motion Record (Dec. 1, 2003).
Defendant Memorandum (Interlocutory Injunction Motion) (Feb. 5, 2004).
Amended Statement of Defense and Counterclaim (Dec. 10, 2003).
Order Dismissing Motion to Strike Counterclaim (Dec. 17, 2003).
Direction from Court (Feb. 5, 2004).
Reply and Defence to Counterclaim (Feb. 4, 2004).
China.
Patentee Response in Reexamination of ZL94192386.X (English).
European Patent Office Appeal T 1212/01–332.
Letter of Tanabe Sieyaku (Mar. 18, 2004).
Letter of Eli Lilly w/ attachments A–G (Mar. 18, 2004).
Letter of Icos Corp. (Mar. 19, 2004).
Letter of Bayer (Mar. 22, 2004) (w/ English translation).
Japan.
Japan Appln. No. 518108/96: Trial Decision in Trial Dissatisfaction No. 2000–5850 (English).
Japan Appln. No. 518108/96: Oct. 19, 1998 letter containing English translation of Office Action.
Japan Patent No. 2975590: Decision in Opposition (English).
Korea.
Appln. 97–7001540—Affidavit of Sang–Geon Kim (w/ English translation) and Attachments 1–7 (Mar. 11, 2004).
New Zealand.
*Pfizer v. Lilly* (CIV.2003–404–452).
Minute of Potter J. (Feb. 24, 2004).
Memorandum of Counsel for Plaintiffs in Respect of Directions Conference to be held on Feb. 24, 2004 (Feb. 23, 2004).
Pfizer conference before Potter J (Feb. 24, 2004).
Memorandum of Counsel for Plaintiffs for Judicial Conference on Dec. 5, 2003 dated Nov. 2003.
Telephone Directions Conference Minute of Potter J (Dec. 5, 2003).
Minute of Potter J (Feb. 24, 2004).
Memorandum of Counsel for Plaintiffs In Respect of Directions Conference to be held on Feb. 24, 2004 (Feb. 23, 2004).
Pfizer Conference before Potter J (Feb. 24, 2004).
Undertaking (Dec. 22, 2003).
Undertaking (Jan. 2004).
Telephone Directions Conference Minute of Potter J (Dec. 5, 2003).
Memorandum of Counsel for Plaintiffs for Judicial Conference on Dec. 5, 2003 dated Nov. 2003.
*Pfizer v. Lilly* (CP 18–SD/03).
Confidentiality Order (Feb. 2004).
Judgment of Potter J (Nov. 21, 2003).
Memorandum of Counsel for Eli Lilly for Conference before Justice Potter on Feb. 24, 2004.
Confidentiality Order (Feb. 2004).
Further Submissions by Plaintiff in Opposition to Notice of Application for Further and Better Statement of Defense and Counterclaim (Oct. 22, 2003).
*Pfizer v. Bayer* (CP 67–SD/03).
Amended Statement of Claim dated Dec. 2003.
Particulars of Breach Pursuant to Rule 725ZK Delivered with Amended Statement of Claim dated Dec. 2003.
Notice of Application for Orders Pursuant to Rule 97 (1) Joining Intended Second Plaintiff and (2) Joining Intended Third and Fourth Defendants dated Dec. 2003.
Affidavit of Nicola Jan Morris in Support of Notice of Application for Orders Pursuant to Rule 97 (1) Joining Intended Second Plaintiff and (2) Joining Intended Third and Fourth Defendants dated Dec. 2003.
Further Submissions of Counsel for Defendants in Response to Further Submissions by Plaintiff in Opposition to Defendants' Application for Further and Better Statement of Defence to Counterclaim (Nov. 4, 2003).
*Pfizer v. Lilly* (CIV.2003–404–506).
Telephone Directions Conference Minute of Potter J (Nov. 3, 2003).
*Pfizer v. Lilly* (CP 404/18/03).
Second Amended Statement of Claim (Dec. 2003).
Affidavit of Nicola Jan Morris in Support of Notice of Application for Order Pursuant to Rule 97 Joining Intended Second Plaintiff (Dec. 2003).
Notice of Application for Orders Pursuant to Rule 97 Joining Intended Second Plaintiff (Dec. 2003).
South Africa.
Revocation Case 94/4018 (*Bayer v. Pfizer*).
Applicants' Notice of Intention to Amend w/ Attachments A–G (Apr. 19, 2004).
Applicants' Notice of Intention to Amend (Apr. 19, 2004).
Korenman, S. G., et al., *Treatment of Vasculogenic Sexual Dysfunction with Pentoxifylline, JAGS,* vol. 41, pp. 363–366 (1993).
Allanby, K. S., et al., *Pentoxifyliline in the Treatment of Vascular Impotence—Case Reports, Cardiovascular Center of Northern Virginia,* pp. 418–420 (May 1991).
Korenman, S. G. et al., *Treatment of Vasculogenic Sexual Dysfunction with Pentoxifylline, JAGS,* vol. 41, pp. 363–366 (1993).
Morley, J. E., *Management of Impotence, Impotence,* vol. 93, No. 3, pp. 65–72 (Feb. 15, 1993).
Rudd, R. M., et al., *Inhibition of Exercise–Induced Asthma by an Orally Absorbed Cell Stabilizer (M&B 22,948), Br. J. Dis. Chest,* vol. 77, pp. 78–86 (1983).
Reiser, J., et al., *The Effect of Zaprinast (M&B 22,948, an Orally Abpsorbed Mast Cell Stabilizer) on Exercise–Induced Asthma in Children, Br. J. Dis. Chest,* vol. 80, pp. 157–163 (1986).
Rajfer, J., et al., Nitric Oxide as a Mediator of Relaxation of the Corpus Cavemosum in Response to Nonadrenergic, Noncholinergic Neurotransmission, *The New England Journal of Medicine,* vol. 326, No. 2, pp. 90–94 (Jan. 9, 1992).
Nicholson, C. D., et al., *Differential modulation of tissue function and therapeutic potential of selective inhibitors of cyclic nucleotide phosphodiesterase isoenzymes, TIPS,* vol. 12, pp. 19–27 (Jan. 1991).
Murray, K. J., et al., *Phosphodiesterase $V_A$ Inhibitors, DN&P,* vol. 6, No. 3, pp. 150–156 (Apr. 1993).
Beavo, J. A., et al., *Primary sequence of cyclic nucleotide phosphodiesterase isozymes and the design of selective inhibitors, TIPS,* vol. 11, pp. 150–155 (Apr. 1990).
European Patent Application No. 043 756, published Jan. 2, 1992.
Bush, P. A., et al., *Nitric Oxide is a Potent Relaxant of Human and Rabbit Corpus Cavernosum, The Journal of Urology,* vol. 147, pp. 1650–1655, (Jun. 1992).

NIH Concensus Statement, *Impotence,* vol. 10, No. 4, Dec. 7–9, 1992.
Bush, M. A., *The role of the L–arginine–nitric oxide–cyclic GMP pathway in relaxation of corpus cavernosum smooth muscle,* University of California, Los Angeles, 1993.
Cortijo, J., et al, *Investigation into the role of phosphodiesterase IV in bronchorelaxation , including studies with human bronchus, Br. J. Pharmacol,* vol. 108, pp. 562–568, (1993).
European Patent Application No. 0 526 004, published Mar. 2, 1993.
Trigo–Rocha, F., et al., *Nitric oxide and cGMP: mediators of pelvic nerve–stimulated erection in dogs, the American Physiological Society,* pp. H419–H422, (1993).
International Patent Application No. WO 93/07149, published Apr. 15, 1993.
Trigo–Rocha, F., et al., *The Role of Cyclic Adenosine Monophosphate, Cyclic Guanosine Monophosphate, Endothelium and Nonadrenergic, Noncholinergic Neurotransmission in Canine Penile Erection, The Journal of Urology,* vol. 149, pp. 872–877, (Apr. 1993).
Taher, A, et al., Abstract entitled *Phosphodiesterase activity in human cavernous tissue and the effect of various selective inhibitors, Journal of Urology,* vol. 149, p. 285A, (1993).
Bush, M. A., *The role of the L–arginine–nitric oxide–cyclic GMP pathway in relaxation of corpus cavernosum smooth muscle,* University of California, Los Angeles, 1993.
Australian Documents.
Proceedings No. V 604 of 2002.
Application, Statement of Claim & Particulars of Invalidity for Australian (Sep. 17, 2002).
Transcript of Proceedings dated Sep. 9, 2003.
Notice of Appearance of Blake Dawson Waldron.
Further Amended Application (Aug. 5, 2003).
Further Amended Statement of Claim (Aug. 5, 2003).
Order dated May 29, 2003.
Order dated Jun. 10, 2003.
Letter to Blakes Characterizing Invention (Jan. 20, 2003).
Cross Claim (Jun. 6, 2003).
Notice of Motion (May 29, 2003).
Affidavit of Sally Ann Nicholson (May 29, 2003).
Exhibit SAN–1.
Exhibit SAN–2.
Exhibit SAN–3.
Exhibit SAN–4.
Exhibit SAN–5.
Exhibit SAN–6.
Proceedings No. V 108 of 2003.
Order dated May 26, 2003.
Order dated Jun. 10, 2003.
Application (Apr. 1, 2003).
Proceeding No. V 111 of 2003.
Order dated May 19, 2003.
Facsimile to DCC in Relation to Answers to Request for Further and Better Particulars (May 23, 2003).
Facsimile to Corrs Providing Further Particulars (May 30, 2003).
Cross Claim (Jun. 6, 2003).
Notice of Motion (May 29, 2003).
Proceeding No. V 108 of 2003.
Order dated May 29, 2003.
Affidavit of Sally Ann Nicholson (May 29, 2003).
Affidavit of Sally Ann Nicholson (Mar. 5, 2003).
Proceeding No. V 604 of 2002.
Further Amended Particulars of Invalidity (Jul. 24, 2003).
Defense to Cross–Claim (Jul. 24, 2003).
Particulars of Invalidity to the Defense to Cross–Claim (Jul. 24, 2003).
Transcript of Proceedings dated Apr. 1, 2003.
Transcript of Proceedings dated Jun. 10, 2003.
Defense to Cross–Claim (Jul. 11, 2003).
Proceeding No. V 367 of 2003.
Proceeding No. V 604 of 2002.
Application (Sep. 17, 2002).
Amended Application (Feb. 10, 2003).
Statement of Claim (Sep. 17, 2002).
Amended Statement of Claim (Feb. 10, 2003).
Particulars of Invalidity (Sep. 17, 2002).
Amended Particulars of Invalidity (Feb. 10, 2003).
Defense (Jan. 24, 2003).
Reply to Defense (Feb. 10, 2003).
Affidavit of Stephen Marcus Stern (Mar. 27, 2003).
Application (Mar. 6, 2003).
Application under preliminary Discovery under Order 15A rule 6 (May 9, 2003).
Affidavit of Matthew Guy Swinn (May 8, 2003).
Order dated Apr. 1, 2003.
Notice of Appearance (Oct. 17, 2002).
Proceeding No. V 604 of 2003.
Reasons for Judgment in the Patent Amendment Issue (Sep. 18, 2003).
Statement of Grounds for Amending Australian Patent 676571 (Jul. 25, 2003).
Outline of the Respondent's submissions in relation to the construction of the proposed amended claim 10.
Notice of Application to Amend the Patent pursuant to s105 (Apr. 17, 2003).
Statement of Grounds Relied Upon for the Amendment of Australian Patent 676571 (Jul. 21, 2003).
Statement of Grounds Relied Upon by "Lilly" in Opposition to the Proposed Amendment (Jul. 29, 2003).
First Respondent's Outline of Submissions relating to the s105 Amendment (Sep. 8, 2003).
Statement of Grounds Relied Upon by "Bayer" in Opposition to the Proposed Amendment (Aug. 7, 2003).
Respondent's Outline of Submissions (Sep. 8, 2003).
Brazilian Documents.
Homologation of a Foreign Ruling Lawsuit, Case No. 79–21, Filed before the Brazilian Federal Supreme Court, Foreign Ruling 7921 Re EP 0 702 555 (English Language Translation) (vol. 1 of 2).
English Translation of Nullity Action 2003.61.00.010308.3 (*Bayer* v. *Pfizer* Re Pat No. PI 1100088–0) (1 of 4).
English Translation of Nullity Action (3 of 4).
Ignamo et al., Biochem and Biophys. Rsch., 843–850 (1990).
*Pfizer* v. *Eli Lilly* (Inhibitory Action 000.03.037147–3): vols. 1–14. (English).
*Pfizer* v. *Eli Lilly* (Case No. 293.588.4): Bill of Review Against Rejection of the Preliminary Injunction (vol. 1). (English).
*Pfizer* v. *Eli Lilly* (Case No. 315.955.4): Bill of Review Against Redistribution of the Action (English).
*Pfizer* v. *Eli Lilly*:Unspecified Provisional Remedy Supreme Court Rio (vol. 1) (English).
*Pfizer* v. *Eli Lilly*:Unspecified Provisional Remedy Supreme Court Brasilia (vol. 1) (English).

*Eli Lilly* v. *Pfizer* (Declaratory Action 2003.001.034974–6): vols. 1–6 (English).
*Pfizer* v. *Eli Lilly* (Case No. 2003.002.05456): Bill of Review Against the Grant of the Preliminary Injunction (vols. 1–6) (English).
*Pfizer* v. *Eli Lilly* (Case No. 10146/2003): Bill of Review Against Rejection of Motion Seeking Removal (vols. 1–2) (English).
*Lilly* v. *Pfizer*: Homologation of a Foreign Ruling No. 7921 (vols. 3–5). (English).
*Bayer* v. *Pfizer* (Inhibitory Action No. 2003.03.040625–0); vols. 1–12. (English).
*Pfizer* v. *Bayer* (Case No. 294.153.4): Bill of Review Against the Grant of the Preliminary Injunction (English).
*Pfizer Ltd.* v. *Eli Lilly* (Inhibitory Action Case No. 315.955.4) vol. II: Bill of Review Against Redistribution (English).
*Lilly Icos.* v. *Pfizer Ltd.* (Homologation of a Foreign Ruling Case No. 7921) vol. VI (English).
*Eli Lilly* v. *Pfizer Ltd.* (Declaratory Action Case No. 2003.001.034974–6) vol. VII (English).
*Pfizer Ltd.* v. *Bayer* (Inhibitory Action Case No. 2003.03.040625–0) vol. XIII (English).
*Pfizer Ltd.* v. *Eli Lilly* (Case No. 315.955.4): Bill of Review Against the Decision that Determined the Redistribution of the Inhibitory Action to the 8$^{th}$ Business Court of the Jurisdiction of Rio De Janeiro, vol. III (English).
*Pfizer Ltd.* v. *Eli Lilly* (Case No. 315.955.402): Precautionary Action, vol. I (English).
*Pfizer Ltd.* v. *Eli Lilly* (Case No. 2003.03037147–3): Inhibitory Action, vol. XV (English).
*Eli Lilly* v. *Pfizer Ltd.* (Case No. 2003.001.034947–6): Declaratory Action, vol. VIII (English).
*Pfizer Ltd.* v. *Eli Lilly* (Case No. 8042): Precautionary Action (Change of Venue), vol. 1 (English).
*Pfizer Ltd.* v. *Eli Lilly* (Case No. 2004.002.00284): Bill of Review Filed Against the Decision that Did Not Grant the Allegation of Active Illegitimacy to the Process, vol. I (English).
*Bayer .S.A.* v. *Pfizer Ltd.* (Case No. 331.673–4): Bill of Review Filed Against the Decision that Did Not Grant the Suspension of the Process, vol. I (English).
*Pfizer Ltd.* v. *Bayer S.A.* (Case No. 000.03.040625–0): Inhibitory Action, vol. XIV (English).
*Bayer S.A.* v. *Pfizer Ltd.* (Case No. 2003.61.00.010308–3): Nullity Action, vol. XII (English).
Canadian Documents.
*Bayer, et al* v. *Pfizer Research* (T2097–02).
*Pfizer Research* v. *Bayer* (T2081–02).
*Pfizer Research* v. *Bayer* (T2082–02).
Plaintiff's Responding Motion Record (Defendant's Motion to Strike) (Mar. 21, 2003).
*Bayer, et al.* v. *Pfizer Research* (T865–02).
Statement of Defense (Sep. 20, 2002).
*Lilly Icos, et al.* v. *Pfizer Research* (T341–02).
*Bayer, et al.* v. *Pfizer Research, et al.*
Amended Statement of Defense (Amended Pursuant to the Order of Prothonotary Lafreniere, dated Oct. 2, 2002 and Rule 200.
Canada Impeachment Papers.
*Lilly Icos, et al.* v. *Pfizer Research.*
Morley, Impotence v. 93, No. 3, pp. 6572 (1993).
Rafjer et al., NE J. Med., v. 326, No. 2, pp. 90–94 (1992).
Trigo–Rocha et al., J. Urology, vo. 149, 872–877 (1993).
Jun. 6, 2002 Order (Jun. 6, 2002).
Sep. 19, 2002 Letter from D. MacOdram.
Disclaimer w/respect to Canadian Pat. No. 2,163,446 (Nov. 8, 2002).
Request to Admit Facts (Oct. 28, 2002).
Defendant's Motion Record (Rule 369 Motion on Consent for an Extension of Time) (Aug. 2, 2002).
Plaintiff's Motion Record (Motion to Strike Paragraphs of the Statement of Defense and for Particulars, Returnable Sep. 23, 2002).
Responding Motion Record of the Defendant (Plaintiff's Motion to Strike and for Particulars) (Sep. 25, 2002).
*Pfizer Research, et al* v. *Bayer AG* (T2027–02).
*Pfizer Research* v. *Lilly Icos* (2025–02).
*Bayer, et al.* v. *Pfizer Research* (T1964–02).
Motion Record (Feb. 28, 2003).
Defendant's Supplementary Motion Record (Motion to Strike Statement of Claim) (Dec. 13, 2002).
Plaintiff's Motion Record (Defendant's Motion to Strike Statement of Claim) (Dec. 13, 2002).
Defendant's Motion Record (Motion to Strike Statement of Claim) (Dec. 11, 2002).
*Pfizer Research, et al* v. *Bayer AG* (T2081–02).
Plaintiff's Motion Record (Motion for Extension of Time to Serve Claim) (Feb. 18, 2003).
Klageschrift (German) (Dec. 12, 2002).
Summary of Documents to be Served.
*Pfizer Research* v. *Lilly Icos* (T2082–02).
Motion Record of the Defendants Lilly Icos and Eli Lilly Canada, Inc. (Returnable Mar. 3, 2003).
Affidavit of Service (Feb. 7, 2003).
*Pfizer* v. *Lilly,* Patent Infringement (T1721–03).
Motion Record (Plaintiff's Motion for an Interim Injunction) (Sep. 23, 2003) (vols. 1–2).
Defendants' Written Submissions (Oct. 28, 2003).
Protective Order (Oct. 16, 2003).
*Bayer AG* v. *Pfizer* (T865–02).
*Bayer* v. *Pfizer* (T865–02).
Motion Record (Jun. 24, 2003).
Brief of Authorities.
*Lilly Icos* v. *Pfizer* (T341–02).
Defendant's Responding Motion Record (Motion to Consolidate) (Jul. 8, 2003).
Plaintiff's Responding Motion (Motion to Consolidate) (Jul. 15, 2003).
Plaintiff's Brief of Authorities (Jul. 15, 2003).
*Lilly* v. *Pfizer* (T341–02).
Amended Reply to Amended Statement of Defence (Mar. 24, 2003).
Affidavit of Documents of Lilly Icos (Mar. 28, 2003).
*Bayer* v. *Pfizer* (T1954–02).
Order (Mar. 25, 2003).
*Pfizer* v. *Bayer* (T2081–02).
Order (Mar. 17, 2003).
Defendant's Motion Record on Consent to Extend Time (Apr. 7, 2003).
Defendant's Motion Record on Consent to Extend Time (May 28, 2003).
Plaintiff's Motion Record to Extend Time (Jun. 11, 2003).
Defendant's Motion Record on Consent to Extend Time (Jun. 27, 2003).
*Pfizer* v. *Lilly* (T2082–02).
*Bayer* v. *Pfizer* (T–865–02).
*Lilly* v. *Pfizer* (T–341–02).

*Pfizer* v. *Lilly* (T–1721–03).
Reasons for Order (Nov. 3, 2003).
Pfizer Motion record Motion for Interlocutory Injunction (vols. 3–5,7,8) (Jan. 16, 2004).
Defendant's responding Motion Record (vols. 1–3) (Dec. 15, 2003).
Pfizer Motion to Strike Counterclaim Motion Record (Dec. 1, 2003).
Amended statement of Defence and Counterclaim (Dec. 10, 2003).
*Bayer* v. *Pfizer* (Case No. T–865–02).
Order (Mar. 18, 2004).
*Pfizer* v. *Lilly* (Case No. T–121–03).
Order (Apr. 14, 2004).
Order (Mar. 17, 2004).
Reply to Defence to Counterclaim (Feb. 16, 2004).
Reasons for Order and Order (Feb. 11, 2004).
*Bayer, et al.* v. *Pfizer Research* (T–341–02).
Order (dated Oct. 4, 2004).
Order (dated Jun. 15, 2004).
Protective Order (dated Sep. 3, 2004).
Moving Party's Motion Record (dated Sep. 1, 2004).
*Bayer, et al.* v. *Pfizer Research* (T–865–02).
Notice of Discontinuance and Consent to Discontinuance (dated Dec. 14, 2004).
Motion Record (dated Dec. 14, 2004).
Plaintiffs Motion Record (dated Jun. 7, 2004).
Defendant's Responding Motion Record (dated Jun. 11, 2004).
Moving Party's Motion Record (Rule 389 Motion on Consent by Protective Order).
Disclaimer with Respect to Canadian Patent No. 2,163,446 (dated Apr. 29, 2004).
Chilean Documents.
Appln. No. 1.127–98: Decision from the Appeals Court Rejecting the Application w/ English Language Translation (Sep. 24, 2002).
Pfizer's Writ of Complaint to the Supreme Court of Justice (English).
Requests to the Court to Appoint an Examiner (in English) (Mar. 8, 2002).
Requests to Court to Appoint an Examiner (Mar. 8, 2002).
Patent No. ZL94192386.X.
Further Observations of Requester 2 (English) ( Aug. 12, 2002).
Evidence filed by Patentee.
Truss, M. C., et al., *Role of the Nitric Oxide Donor Linsidomine Chlorhydrate (SIN–1) in the Diagnosis and Treatment of Erectile Dysfunction, Urology*, vol. 44, No. 1, pp. 553–556, (1994).
Lugg, J. A., et al., *The Role of Nitric Oxide in Erectile Function, Journal of Andrology*, vol. 14, No. 1, pp. 2–4, (1993).
Blakeslee, S., *Chemical A Factor in Male Impotence, The New York Times*, 1992.
Trigo–Rocha, F., et al., *Intracellular Mechanism of Penile Erection in Monkeys, Neurology and Urodynamics*, vol. 13, pp. 71–80, (1994).
Trigo–Rocha, F., et al, *The effect of intracavernous injection of potassium channel openers in monkeys and dogs, Int. J. Impotence Res.*, vol. 7, pp. 41–48 (1995).
Trigo–Rocha, F., et al., *Sodium nitroprusside: physiologic effects as a nitric oxide donor in three species, Int. J. Impotence Res.*, vol. 7, pp. 49–56, (1995).

Stief, C. G., et al., *Preliminary report on the effect of the nitric oxide donor SIN–1 on human cavrnous tissue in vivo, World J. Urol.*, vol. 237–239, (1991).
Fareman, M. M., et al., *Approaches for the Development of Oral Drug Therapies for Erectile Dysfunction, Seminars in Urology*, vol. VIII, No. 2, p. 107–112, (1990).
Owen, J. A., et al., *Topical Nitroglycerine: A Potential Treatment for Impotence, Journal of Urology*, vo. 141, pp. 543–545, (1989).
Traish, A. M., et al., *A Heterogeneous Population of α1 Adrenergic Receptors Mediates Contraction of Human Corpus Cavernosum Smooth Muscle to Norepinephrine, Journal of Urology*, vol. 153, pp. 222–227, (1996).
Extract from Proprietor's EPO submission Jun. 22, 2001.
Boolell, M. et al., *Sildenafil, a novel effective oral therapy for male erectile dysfunction, British Journal of Urology*, vol. 78, pp. 257–162, (1996).
Bardley, I., et al., UK–92,480, *A New Oral Therapy for Erectile Dysfunction, a Double–blind, Placebo Controlled Trial with Treatment Take as Required, Proceedings of the American Urological Association*, vol. 155, pp. 495A.
Boolell, M., et al., *Sildenafil: an orally active type 5 cyclic GMP–specific phosphodiesterase inhibitor for the treament of penile erectile dysfunction, Int. Journal of Impotence Res.*, vol. 8, pp. 47–52, (1996).
Lue, T. F., *A Study of Sildenafil (Viagra™), A New Oral Agent for the Treatment of Male Erectile Dysfunction, Journal of Urology*, vol. 157, No. 4, (1997).
Goldstein, I., et al., *British Journal of Urology*, vol. 80, supplement 2, (1997).
Goldstein, I., et al., *Oral Sildenafil in the Treatment of Erectile Dysfunction, The New England Journal of Medicine*, vol. 338, No. 20, pp. 1397–1404, 1998.
Chinese translation of Trigo–Rocha, F., et al., *Sodium nitroprusside: physiologic effects as a nitric oxide donor in three species, Int. J. Impotence Res.*, vol. 7, pp. 49–56, (1995).
Stief, C. G., et al., *The Effect of the Specific Phosphodiesterase (PDE) Inhibitors on Human and Rabbit Cavemous Tissue in Vivo and in Vivo, Journal of Urology*, vol. 159, pp. 1390–1393, (1998).
Owen, J. A. et al., *Topical Nitroglycerin: A Potential Treatment for Impotence, Journal of Urology*, vol. 141, pp. 546–548, (1989).
Patentee Response in Reexamination of AL94192386.X (English).
Decision in case No. 94192386.X (English translation).
Comments of the Third Parties of the Administrative Litigation with English Translation, dated Nov. 30, 2004.
The Plaintiff's Response dated Jan. 4, 2005 (English).
Draft Bill of Complaint (English).
Decision on Invalidation Request (dated Jun. 28, 2004).
Defendant's Response.
EPO Documents.
T–1212/01–332.
Opponent 4 Letter of Oct. 10, 2002.
English Translation of Bayer's Letter dated Oct. 17, 2002.
T 1212/01–332:
*Drugs and male sexual function, British Medical Journal*, vol. 2, PT 6195, pp. 883–884, (Oct. 13, 1979).
Michel D., *Impotenz durch anithypertensive Therapie!, Fortschritte der Medizin*, vol. 97, No. 36, pp. 1555, (1979).
Hogan, M. J., et al., *Antihypertensive therapy and male sexual dysfunction, Psychosomatics*, vol. 21, PT 3, pp. 234–237, (Mar. 1980).

*Drugs that cause sexual dysfunction*, Med. Lett. on Drug & Therapy, vol. 22, No. 25, 108–110 (1980).
Ahmad, S. *Hydralazine and Male Impotence*, Chest, vol. 78, No. 2, pp. 358, (1980).
Wartman, S. A., *Sexual side effects of antihypertensive drugs*, Posteraduate Medicine, vol. 73, No. 2, pp. 133–135 & 138, (1983).
*Drugs that cause sexual dysfunction*, Med. Lett. on Drug & Therapeutics, vol. 25, No. 6411, pp. 73–76, (1983).
Van Arsdalen, K. N., et al., *Drug–induced sexual dysfunction in older men*, Geriatrics, vol. 39, No. 10, pp. 63–67 (1984).
Stevenson, J. G., et al., *Sexual Dysfunction Due to Antihypertensive Agents*, Drug Intelligence and Clinical Pharmacy, vol. 18, pp. 113–121, (1984).
Segraves, R. T., et al., *Erectile Dysfunction Associated with Pharmacological Agents*, Diagnosis and Treatment of Erectile Disturbances: New York: Plenum, pp. 23–63, (1985).
Mockel, J., et al., *Les impuissances medicamenteuses*, Revue Medicale de Bruxelles, vol. 6, No. 6, pp. 418–424, (1985).
Sternon, J. Les impuissances medicamenteuses, *Contraception Fertilite Sexualite*, vol. 14, No. 3, pp. 253–257, (1986).
*Drugs that cause sexual dysfunction*, Med. Lett. on Drugs & Therapeutics, vol. 29, Issue 744, pp. 65–70, (1987).
Wein, A. J., et al., *Drug–induced Male Sexual Dysfunction*, Urologic Clinics of North America, vol. 15, No. 1, pp. 23–31, (1988).
Strauss, V. B., et al., *Arzneimittelbedingte Hemmungen sexueller Funktionen*, Fortschr. Med., 106, Jg(1988), Nr. 4, S. 61/33–63/37.
Curb, J. D., et al., *Antihypertensive Drug Side Effects in the Hypertension Detection and Follow–up Program*, Suppl. II Hypertension, vol. 11, No. 3, pp. 11–51–11–55, (1988).
Lua, T. F., et al., *Pharmacology of Erection and Impotence*, Comtemporary Management of impotence and Infertility, Baltimore, pp. 51–54, (1988).
Galbraith, R. A., *Sexual Side Effects of Drugs*, Drug Therapy, vol. 21, pp. 38–40 & 45, (1991).
Tewari, A., et al., *Hypertension, Antihypertensives and Male Sexual Dysfunctions: A Review*, Indian Journal of Urology, vol. 10, No. 1, pp. 1–6, (1993).
Brock, G. B., et al., *Drug–induced Male Sexual Dysfunction*, Drug Safety, vol. 8, No. 6, pp. 414–426, (1993).
Pray, W. S., *Medications and Sexual Dysfunction*, Pharmacist, vol. 18, No. 8, pp. 27, 28, 30,32, (1993).
Wetti, R. S., et al., *Treatment of Intraoperative Penile Tumescence*, Journal of Urology, vol. 124, pp. 925–926, (1980).
Zentgraf, M., et al., *Diagnosis and Therapy of Erectile Dysfunction Using Papaverine and Phentolamine*, Urol. Int. vol. 43, pp. 65–75, (1988).
Australian High Court's decision in re *Aktieboleget Hässie v. Alphapharm Pty Limited*.
Declaration by Peter Ellis.
Smith, D. A., et al. *Pharmokinetics and Metabolism in Drug Design*, pp. 35–48, (2001).
European Patent Office Appeal T1212/01–332.
Letter of Tanabe Sleyaku (Mar. 18, 2004).
Letter of Eli Lily w/ Attachments A–G (Mar. 18, 2004).
Appeal Proceedings Case No. T1212/01–332 Proprietors' Comments (dated Sep. 27, 2004).
Applicants' Response (Apr. 19, 2002).
Israell Documents.
Japanese Documents.
J. Urology. V. 149, No. 4, 285A (1993).

Letter Concerning Sep. 26, 2002, Rejection in JP Appln. No. 21939/99.
Japan Patent No. 2925034: (Opposition No. 2000–70281): Notification of Reasons for Revocation (w/ English translation).
Argument (Apr. 18, 2003) (w/ English translation).
Reasons for Rejection w/English summary letter (Oct. 16, 2002).
Notice of Appeal Trial (Dec. 27, 2003) (w/ English translation).
Dismissal of Appeal Trial (Sep. 8, 2003) (w/ Englsh translation).
Japan Appln. No. 21945/99.
First Official Action (Feb. 28, 2003) w/ English summary letter (Apr. 15, 2003).
Opponents' Petition re Pat. No. 2925034 (w/ English translation).
EPO Appln No. 94 916 236.6 Opposition Grounds for Decision (Annex) (Oct. 11, 2001).
EPO Appln. No. 92 916 236.6 Opposition Oral Hearing Minutes (Jul. 16, 2001).
Japan Appln. No. 518108/96: Trial Decision in Trial Dissatisfaction No. 2000–5850 (English).
Japan Appln. No. 518108/96: Oct. 19, 1998 letter containing English translation of Office Action.
English Translation of the Appeal Brief in Case No. 2003 Hu 380 (Mar. 10, 2003).
English Translation of Answer Brief in Case No. 2003 Hu 380 (Mar. 25, 2003).
Sildenafil, CMAJ, 163(9), 1171–1175 (2000).
Original Korean Text and English Translation of KIPO Brief in 2001 Heo 1013 Filed Oct. 16, 2002.
Manganiello et al., Arch. Biochem. And Biophysics, v. 322, No. 1, pp. 1–13 (1995).
Teixerira, TIPS, v. 18, 164–170 (May 1997).
Raeburn, Int. J. Biochem. Cell Biol., v. 27, No. 1, pp. 29–37 (1995).
KIPO Brief (English and Korean) (Jun. 24, 2002) w/Exhibits Eul–6—Eul–8.
Rosen et al., J. Sex Marital Ther. 1993 Fall; 19(3):171–88 (Abstract) (Exh. Eul–9).
KIPO Brief (English and Korean) (Oct. 16, 2002) w/ Exh. Eul–10 and Ref. 5.
Dickinson et al., Biochem. J., v. 323, 371–377 (1997).
Pfizer Rebuttal Brief (English and Korean) (Mar. 2002) w/Exh. Kap–16 and Kap–17 and Refs. 2 and 3.
KIPO Brief (English and Korean) (Jun. 24, 2002) w/Refs. 10–16.
Royal Courts of Justice Judgement in Case No. A3/2000/3811 (Jan. 23, 2001).
Pfizer Brief (English and Korean) (Jun. 2002) w/Exh. Kap–18—Kap–61.
Morales, A., et al., *Oral and Topical Treatment of Erectile Dysfunction*, Impotence, vol. 22, No. 4, pp. 879–886, (1995).
Krane, R. J., et al., *Medical Progress: Impotence*, New England Journal of Medicine, vol. 321, No. 24, pp. 1648–1659, (1989).
Carrier, S., et al., *Pathophysiology of Erectile Dysfunction*, Urology, vol. 42, No. 4, pp. 468–481, (1993).
Holmquist, F., et al., *Actions of 3–Morpholinosydnonimin (Sin–1) on Rabbit Isolated Penile Erectile Tissue*, Journal of Urology, vol. 150, pp. 1310–1315, (1993).

Raifer, J., *This Month in Investigative Urology: From the Lab to the Clinic, Journal of Urology*, vol. 159, pp. 1792, (1998).

Whitehead, E. D., et al., *Treatment alternatives for impotence, Postgradurate Medicine*, vol. 88, No. 2, pp. 139–147, (1990).

Morley, J. E., et al., *Management of Impotence: Diagnostic considerations and therapeutic options, Postgraduate Medicine*, vol. 93, No. 3, (1992).

NIH Consensus Development Panel on Impotence, *Impotence, JAMA*, vol. 270, No. 1, (1993).

Utiger, R. D., et al. *A Pill for Impotence, New England Journal of Medicine*, vol. 338, No. 20, pp. 1458–1459, (1998).

Christensen, S. B., et al., *Chapter 19: Isozyme–Selective Phosphodiesterase Inhibitors as Antiashmatic Agents, Annual Reports in Medicinal Chemistry*, pp. 188–196, (1994).

Declaration of Peter Ellis.

Exh. Eul–31 w/ English excerpt.

Pfizer Rebuttal Brief (English and Korean) (Aug. 2002) w /Exh. Kap–63 and Kap–64.

Pfizer Brief (English and Korean) (Dec. 2002):

Telxeira et al., TiPS, v. 18, pp. 164–170 (May 1997).

Raeburn et al., Int. J. Biochem. Cell Biol., v. 27, No. 1, pp. 29–37 (1995).

Appln. 97–7001540—Affidavit of Sang–Geon Kim (w/ English translation) and Attachments 1–7 (Mar. 11, 2004).

English Translation of the Request for the Administrative Declaration of Infringement Patent No. 195,457 B.

*Pfizer* v. *Bayer*.

English Translation of the Request for the Administrative Declaration of Infringement Patent No. 195,457 B.

*Pfizer* v. *Lilly* (CP–18–SD/03).

Interlocutory Application for More Explicit Statement of Defense to Counterclaim (Jul. 22, 2003).

Affidavit of Mark John Gavin (Apr. 16, 2003) w/ Exhibits A–G.

*Pfizer* v. *Lilly* (CP 18–SD/03).

Affidavit of Stephen Marcus Stem (Apr. 24, 2003).

Statement of Defence (May 16, 2003).

Notice of Intention for Amend NZ 266463.

Notice of Intention for Amend NZ 314110.

Notice of Application for Leave to Amend NZ 266463 and NZ 314110 (Sep. 18, 2003). .

Pfizer v. Lilly (CIV 2003–404–452):

Judgement of Potter J as to Costs on Defendants' Interlocutory Application that the Plaintiff File a More Explicit Statement of Defence to Counterclaim (Dec. 18, 2003).

Pfizer v. Bayer (CIV 2003–404–506):

Pfizer v. Lilly (CIV.2003–404–452).

Memorandum of Counsel for Plaintiffs in Respect of Directions Conference to be held on Feb. 24, 2004 (Feb. 23, 2004).

Memorandum of Counsel for Plaintiffs for Judicial Conference on Dec. 5, 2003 dated Nov. 2003.

"Pfizer Conference before Potter J (Feb. 24, 2004."

Memorandum of Counsel for Judicial Conference on Dec. 5, 2003 dated Nov. 2003.

Pfizer v. Lilly (CP 18–SD/03).

Judgement of Potter J (Nov. 21, 2003).

Memorandum of Counsel for Eli Lilly for Conference before Justice Potter on Feb. 24, 2004.

Confidentially Order (Feb. 2004).

Judgment of Potter J (Nov. 21, 2003).

Further Submissions by Plaintiff in Opposition to Notice of Application for Further and Better Statement of Defence and Counterclaim (Oct. 22, 2003).

Pfizer v. Bayer (CP 67–SD/03).

Notice of Application for Orders Pursuant to Rule 97 (1) Joining intended Second Plaintiff and (2) Joining intended.

Affidavit of Nocola Jan Morris in Support of Notice of Application for Orders Pursuant to Rule 97 (1) Joining Intended Second Plaintiff and (2) Joining Intended Third and Fourth Defendants dated Dec. 2003.

Further Submissions of Counsel for Defendants in Response to Further Submissions by Plaintiff in Opposition to Defendants' Application for Further and Better Statement of Defence to Counterclaim (Nov. 4, 2003).

*Pfizer* v. *Lilly* (CIV. 2003–404–506).

*Pfizer* v. *Lilly* (CP 404/18/03).

Second Amended Statement of Claim (Dec. 2003).

Affidavit of Nicola Jan Morris in Support of Notice of Application for Order Pursuant to Rule 97 Joining Intended Second Plaintiff (Dec. 2003).

Notice of Application for Orders Pursuant to Rule 97 Joining Intended Second Plaintiff (Dec. 2003).

*Bayer* v. *Pfizer* (Patent 94/4018): Application for Revocation (Apr. 17, 2003).

*Lilly* v. *Pfizer* (Patent 94/4018): Application for Revocation (May 5, 2003).

Revocation Case No. 94/4018 (*Bayer* v. *Pfizer*).

Statement of Particulars (Apr. 19, 2004).

Revocation Case No. 94/4018 (*Bayer* v. *Pfizer*).

Delivery Notice (May 14, 2004).

Applicant's Amended Statement of Particulars (May 14, 2004).

Letter to Registrar (May 14, 2004).

Revocation Case 94/4018 (*Bayer* v. *Pfizer*).

Applicants' Notice of Intention to Amend w/ Attachments A–G (Apr. 19, 2004).

Revocation Case 94/4018 (*Lilly* v. *Pfizer*).

Applicants' Notice of Intention to Amend (Apr. 19, 2004).

Korenman, S. G., et al, *Treatment of Vasculogenic Sexual Dysfunction with Pentoxifylline, JAGS*, vol. 41, pp. 363–366 (1993).

Allenby, K. S., et al., *Pentoxifylline in the Treatment of Vascular Impotence—Case Reports, Cardiovascular Center of Northern Virginia*, pp. 418–420 (May 1991).

Korenman, S. G., et al., *Treatment of Vasculogenic Sexual Dysfunction with Pentoxifylline, JAGS*, vol. 41, pp. 363–366 (1993).

Morley, J. E., *Management of Impotence, Impotence*, vol. 93, No. 3, pp. 65–72 (Feb. 15, 1993).

Rudd, R. M., et al., *Inhibition of Exercise–Induced Asthma by an Orally Absorbed Cell Stabilizer (M&B 22, 948), Br. J. Dis. Chest*, vol. 77, pp. 78–86 (1983).

Reiser, J., et al., *The Effect of Zaprinast (M&B 22,948 an Orally Absorbed Mast Cell Stabilizer) on Exercise–Induced Asthma in Children, Br. J. Dis. Chest*, vol. 80, pp. 157–163 (1986).

Raifer, J., et al., *Nitric Oxide as a Mediator of Relaxation of the Corpur Cavernosum in Response to Nonadrenergic, Noncholinergic Neurotransmission, The New England Journal of Medicine*, vol. 326, No. 2, pp. 90–94 (Jan. 9, 1992).

Nicholson, C. D., et al., *Differential modulation of tissue function and therapeutic potential of selective inhibitors of cyclic nucleotide phosphodiesterase isoenzymes, TIPS*, vol. 12, pp. 19–27 (Jan. 1991).

Murray, K. J., et al., *Phosphodiesterase $V_A$ Inhibitors*, DN&P, vol. 6, No. 3, pp. 150–156 (Apr. 1993).

Beavo, J. A., et al., *Primary sequence of cyclic nucleotide phosphodiesterase isozymes and the design of selective inhibitors*, TIPS, vol. 11, pp. 150–155 (Apr. 1990).

European Patent Application No. 043 756, published Jan. 2, 1992.

Bush, P. A., et al., *Nitric Oxide is a Potent Relaxant of Human and Rabbit Corpus Cavernosum*, The Journal of Urology, vol. 147, pp. 1650–1655, (Jun. 1992).

NIH Consensus Statement, *Impotence*, vol. 10, No. 4, Dec. 7–9, 1992.

Bush, M. A., *The role of the L–arginine–nitric oxide–cyclic GMP pathway in relaxation of corpus cavernosum smooth muscle*, University of California, Los Angeles, 1993.

Cortijo, J., et al., *Investigation into the role of phosphodiesterase IV in bronchorelaxation, including studies with human bronchus*, Br. J. Pharmacol., vol. 108, pp. 562–568, (1993).

European Patent Application No. 0 526 004, published Mar. 2, 1993.

Trigo–Rocha, F., et al., *Nitric oxide and cGMP: mediators of pelvic nerve–stimulated erection in dogs*, the American Physiological Society, pp. H419–H422, (1993).

International Patent Application No. WO 93/07149, published Apr. 15, 1993.

Trigo–Rocha, F., et al., *The Role of Cyclic Adenosine Monophosphate, Cyclic Guanosine Monophosphate, Endothelium and Nonadrenergic, Noncholinergic Neurotransmission in Canine Penile Erection*, The Journal of Urology, vol. 149, pp. 872–877, (Apr. 1993).

Bush, M. A., *The role of the L–arginine–nitric oxide–cyclic GMP pathway in corpus cavernosum smooth muscle*, University of California, Los Angeles, 1993.

United States Documents.

*Pfizer v. Lilly ICOS* (No. 02–1561.

Docket Sheet (Oct. 30, 2003).

Complaint (Oct. 22, 2002).

Answer (Jan. 6, 2003).

Pfizer Initial Disclosures (Mar. 21, 2003).

Lilly Initial Disclosures (Mar. 21, 2003).

Pfizer First Interrogatories (Jun. 27, 2003).

Responses to First Interrogatories (Aug. 27, 2003).

*Pfizer v. Bayer* (No. 02–1560).

Complaint (Oct. 22, 2002).

Answer of Bayer AG (Jan. 6, 2003).

Answer of SmithKline Beecham (Jan. 6, 2003).

Pfizer Initial Disclosures (Mar. 21, 2003).

Bayer Initial Disclosures (Mar. 21, 2003).

SmithKline Beecham Initial Disclosures (Mar. 21, 2003).

Stipulated Order (Feb. 13, 2003).

Bayer First Interrogatories (Jun. 20, 2003).

Bayer First Requests for Admission (Jun. 20, 2003).

Pfizer First Interrog. To Bayer (Jun. 27, 2003).

Pfizer First Interrog. To SmithKline Beecham (Jun. 27, 2003).

Pfizer Responses to Bayer First Interrog (Jul. 21, 2003).

Pfizer Responses to Bayer First Requests for Admission (Jul. 21, 2003).

Bayer Amended First Interrog. (Aug. 6, 2003).

Pfizer Responses to Bayer Amended First Interrog (Aug. 27, 2003).

Pfizer Amended First Interrog. (Aug. 6, 2003).

SmithKline Beecham Responses to Pfizer First Interrog. (Aug. 27, 2003).

*Pfizer v. Bayer AG* (No. 03–888).

Complaint (Sep. 22, 2003).

Bayer Responses to Pfizer First Interrog. (Aug. 27, 2003).

Answer of Bayer (Oct. 9, 2003).

Answer of SmithKline Beecham (Oct. 10, 2003).

Reply to Counterclaims of Bayer (Oct. 30, 2003).

Reply to Counterclaims of SmithKline Beecham (Oct. 30, 2003).

Taher et al., 149 J. Urol. 285A (Apr. 1993).

TEVA.

Patent Certification Notice—U.S. Patent No. 6,469,012 (dated Dec. 17, 2004).

Chen, J., et al "Effect of plant–extract osthole on the relaxation of rabbit corpus cavernosum tissue in vitro", J. Urol vol. 163 pp. 1975–1980 (2000).

Lerner, SE, et al. "A Review of Erectile Dysfunction: New Insights and More Questions", J. Urol. 149:1236–55 at 1251 (May 1993).

"NIH Consensus Statement on Impotence" Int. Journal of Impotence Res. vol. 5, pp. 181–199 (1993).

1992 Physician's Desk Reference, p. 1099.

Murad, F., "Drugs Used for the Treatment of Angina: Organic Nitrates, Calcium–Channel, Blockers, and B–Adrenergic Antagonists", Goodman & Gilman's The Pharmacological Basis of Therapeutics, (Eighth Edition), Chapter 32, pp. 764–783 (1990).

Kirby, R. S., et al, "Medical Treatment of Erectile Dysfunction", Impotence Diagnosis and Management of Male Erectile Dysfunction. Oxford: Butterworth–Heinemann Ltd., Chapter 16, pp. 149–151 (1991).

Heaton, J., et al, "Recovery of Erectile Function by the Oral Administration of Apomorphine", Urology, vol. 45, No. 2, pp. 200–206 (1995).

Brock, G., et al, "Impotence: A Patient's Goal Direction Approach", Urology Monograph, pp. 99–110 (1992).

Gennaro, A., "Blakiston's Gould Medical Dictionary", Fourth Edition, p. 343 (1979).

Black's Law Dictionary, Sixth Edition, p. 381 (1990).

Pfizer Canada Inc., Viagra Product Monograph (2006).

Levine, L. A., "New Oral Agents for Erectile Dysfunction", Boston University Medical Campus, Institute for Sexual Medicine, Boston University School of Medicine (2003).

Harris, G., "Pfizer Gives Up Testing Viagra on Women", New York Times (Feb. 28, 2004).

Editors, "Pfizer to end tests of Viagra for women", Drug Week, Expanded Reporting Section, p. 466 (Mar. 19, 2004).

Mascall, S., "Early Promise Lost", The Age (Melbourne), A3, p. 11 (Mar. 16, 2004).

Mayor, S., "Pfizer will not apply for a license for sildenafil for women", British Medical Journal, vol. 328 (7439); p. 542 (Mar. 2004).

DasGupta, R. et al, "Efficacy of Sildenafil in the Treatment of Female Sexual Dysfunction Due to Multiple Sclerosis", Journal of Urology, vol. 171, pp. 1189–1193 (Mar. 2004).

"Cambridge Antibody Technology Announces New Non–Executive Director", Biotech Corporate Happenings Press (Jan. 9, 2003).

Berman, J. et al, "Safety and Efficacy of Sildenafil Citrate for the Treatment of Female Sexual Arousal Disorder: A Double–Blind Placebo Controlled Study", Journal of Urology, vol. 170, pp. 2333–2338 (Dec. 2003).

Basson, R., et al, "Sexual psychophysiology and effects of sildenafil citrate in oestrogenised women with acquired genital arousal disorder and impaired orgasm: a randomised controlled trial", Br J Obster Gynacol, vol. 110, pp. 1014–1024 (Nov. 2003).

Morley, J., et al, "Female Sexuality", Med Clin N Am, vol. 87, pp. 1077–1090 (Sep. 2003).

Bancroft, J. et al, "Distress About Sex: A National Survey of Women in Heterosexual Relationships", Archives of Sexual Behavior, vol. 32, No. 3, pp. 193–208 (Jun. 2003).

Moynihan, R., "The making of a disease: female sexual dysfunction", British Medical Journal, vol. 326 (7379), pp. 45–47 (Jan. 2003).

Saenz de Tejada, "Molecular Mechanisms for the Regulation of Penile Smooth Muscle Contractility", Int. Journal of Impotence Res., vol. 12, Suppl. 4, pp. S34–S38 (2000).

Sachse, R. et al, "Safety, Tolerability and Pharmacokinetics of BAY 38–9456 in Patients with Erectile Dysfunction", Journal of Urology, vol. 163, No. 4, Supplement, p. 204 (2000).

Rotella, et al, "N–3–Substituted Imidazoquinazolinones: Potent and Selective PDE5 Inhibitors as Potential Agents for Treatment of Erectile Dysfunction",J. Med. Chem., vol. 43, pp. 1257–1263 (2000).

Lue, T. et al, "Comparison of oral and intracavernosal vasoactive agents in penile erection", Int. Journal of Impotence Res., vol. 12, Suppl. 1, pp. S81–S88 (2000).

Bivalacqua, T. et al, "Pharmacotherapy for Erectile Dysfunction", Trends in Pharmacological Sciences, vol. 2, pp. 484–489 (2000).

Basson, R. et al, "Report of the International Consensus Development Conference on Female Sexual Dysfunction: Definitions and Classifications", Journal of Urology, vol. 163, pp. 888–893 (Mar. 2000).

Rosen, R. et al, "Position Paper: The Process of Care Model for Evaluation and Treatment of Erectile Dysfunction", Int. J. Impotence, Res., vol. 11, pp. 59–74 (1999).

Palmer, E., "Making the Love Drug", Chemistry in Britain, vol. 35, No. 1, Jan. 1999, pp. 24–26.

Lue, T., "Topical and Oral Agents for Erectile Dysfunction", J. Formos. Med. Assoc., vol. 98, No. 4, pp. 233–241 (1999).

Gingell, JC, et al, "Emerging Pharmacological Therapies for Erectile Dysfunction", Exp. Opin. Ther. Patents, vol. 9, No. 12, pp. 1689–1696 (1999).

Ballard, S. et al, "Effects of Sildenafil on the Relaxation of Human Corpus Cavernosum Tissue In Vitro and on the Activities of Cyclic Nucleotide Phosphodiesterase Isozymes", Journal of Urology, vol. 159, pp. 2164–2171 (1998).

Gregoire, A, "Viagra: on release", British Medical Journal, vol. 317, pp. 759–760 (1998).

Stosic–Grujicic, S. et al, "Pentoxifylline Potentiates Nitric Oxide Production and Growth Suppression in Interferon–γ–Treated L929 Fibroblasts", Cellular Immunology, vol. 184, pp. 105–111 (1998).

Ignarro, L., "Nitric Oxide: A Unique Endogenous Signaling Molecule in Vascular Biology", Bioscience Reports, vol. 19, No. 2, pp. 51–71 (1998).

Jackson, S. et al, "Erectile Dysfunction: Therapy Health Outcomes", Urology, vol. 51(6), pp. 874–882 (1998).

Windmeier, C. et al, "Pharmacological Aspects of Pentoxifylline with Emphasis on Its Inhibitory Actions on Hepatic Fibrogenesis", Gen. Pharmac., vol. 29, No. 2, pp. 181–196 (1997).

Taher, A. et al, "Cyclic nucleotide Phosphodiesterase in human cavernous smooth muscle", World Journal of Urology, vol. 15, pp. 32–35 (1997).

Terrett, N. et al, "Sildenafil (Viagra™), A Potent and Selective Inhibitor of Type 5 cGMP Phosphodiesterase with Utility for the Treatment of Male Erectile Dysfunction", Bioorganic & Medicinal Chemistry Letters, vol. 6, No. 15, pp. 1819–1824 (1996).

Riley, A. "Oral treatments for erectile dysfunction", International Journal of STD & AIDS, vol. 7 Suppl. 3, pp. 16–18 (1996).

Gornella, L., "Editorial: Impotence–Defining the Role of Minimally Invasive Therapy", Journal of Urology, vol. 155, p. 147 (1996).

Sybartz, E. et al, "cGMP Phosphodiesterase Inhibition: A New Mechanism for the Discovery of Therapeutic Agents", Current Pharmaceutical Design, vol. 1, No. 4, pp. 373–390 (1995).

Stief, C. et al, "Cyclic nucleotide phosphodiesterase (PDE) isoenzymes in human cavernous smooth muscle: characterization and functional effects of PDE–inhibitors in vitro and in vivo", Int. Journal of Impotence Research, vol. 7, Suppl 1, pp. 6–7 (1995).

Zorgniotti, A. et al, "Effect of large doses of the nitric oxide precursor, L–arginine, on erectile dysfunction", Int. Journal of Impotence Res., vol. 6, pp. 33–35 (1994).

Carrier, S. et al, "Erectile Dysfunction", Endocrinology and Metabolism Clinics of North America, vol. 23, No. 4, pp. 773–782 (1994).

Saeki, T. et al, "Isolation of Cyclic Nucleotide Phosphodiesterase Isozymes from Pig Aorta", Biochemical Pharmacology, vol. 46, No. 5, pp. 833–839 (1993).

Bush, P. et al, "Comparison of nonadrenergic, noncholinergic–and nitric oxide–mediated relaxation of corpus cavernosum", Int. J. Impotence Res., vol. 4, pp. 85–93 (1992).

Stief, C. et al, "Preliminary results with the nitric oxide donor linsidomine chlorhydrate in the treatment of human erectile dysfunction", Journal of Urology, vol. 148, pp. 1437–1440 (1992).

Murray, K. et al, "Potential Use of Selective Phosphodiesterase Inhibitors in the Treatment of Asthma", New Drugs for Asthma Therapy, Birkhauser Verlag Basel, Agents and actions: Supplements, vol. 34, pp. 27–48 (1991).

Bansal, S., "Sexual Dysfunction in Hypertensive Men, A Critical Review of the Literature", Hypertension, vol. 12, No. 1, pp. 1–10 (1988).

Thompson, W.J., et al, "Multiple Cyclic Nucleotide Phosphodiesterase Activities from Rat Brain", *Biochemistry*, vol. 10, No. 2, pp. 311–316 (1971).

Lin, Y. et al, "The rabbit as an intracavernous injection study model", Urol. Res., vol. 24, pp. 27–32 (1996).

Mahomedy, Y. et al, "A comparison of the effects of orally administered M&B 22,948 (zaprinast) and placebo on changes in ventilatory function in patients with exercise–induced bronchial asthma: A pilot study", Current Therapeutic Research, vol. 40, No. 4, pp. 750–760 (1986).

Derry, F. et al, "Sildenafil (Viagra™): An oral treatment for men with erectile dysfunction caused by traumatic spinal cord injury: A 28–day, double–blind, placebo–controlled, parallel–group, dose–response study", Journal of the Neurological Sciences, vol. 150, Suppl. pp. S270 (1997).

Derry, F. et al, "Sildenafil (Viagra™): An Oral Treatment for Men with Erectile Dysfunction Caused by Traumatic Spinal Cord Injury: A 28–day, Double–blind, Placebo–controlled, Parallel–group, Dose–response Study", Neurology, vol. 48, No. 3, Suppl. 2, pp. A215 (1997).

Derry, F. et al, "Sildenafil (Viagra™): A double–blind, placebo–controlled, single–dose, two–way crossover study in men with erectile dysfunction caused by traumatc spinal cord injury", Journal of Urology, vol. 157, No. 4, Suppl., pp. 181 (1997).

Derry, F. et al, "Sildenafil (Viagra™): A double–blind, placebo–controlled, single–dose, two–way crossover study in men with erectile dysfunction caused by traumatic spinal cord injury", Journal of the Neurological Sciences, vol. 150, Suppl., pp. S134 (1997).

Courtois, F. et al, "Clinical approach to erectile dysfunction in spinal cord injured men. A review of clinical and experimental data", Paraplegia, vol. 33, pp. 628–635 (1995).

Tay, H. et al, "Psychogenic Impotence in Spinal Cord Injury Patients", Arch Phys Med Rehabil, vol. 77, pp. 391–393 (Apr. 1996).

Beretta, G. et al, "Transcutaneous Minoxidil in the Treatment of Erectile Dysfunctions in Spinal Cord Injured Men", Acta Europaea Fertilitatis, vol. 254, No. 1 (1993).

Chancellor, M. et al, "Prospective Comparison of Topical Minoxidil to Vacuum Constriction Device and Intracorporeal Papaverine Injection in Treatment of Erectile Dysfunction Due to Spinal Cord Injury", Urology, vol. 43, No. 3, pp. 365–369 (Mar. 1994).

Roy, G., "Taste Masking in Oral Pharmaceuticals", Pharmaceutical Technology, pp. 84–99 (Apr. 1994).

Ueda, M. "Recent Pharmaceutical Techniques and Future Scope for Taste Masking of Granules", The annual proceedings of Gifu College of Pharmacy, vol. 44, pp. 18–31 (1995).

Silver, P. et al, "Reversal or nitroglycetin tolerance by the cGMP phosphodiesterase inhibitor zaprinast", European Journal of Pharmacology, vol. 199 (1): pp. 141–142 (1991).

Andersson, T. et al, "Interactions between Isoprenaline, Sodium Nitroprusside, and Isozyme–Selective Phosphodiesterase Inhibitors on ADP–Induced Aggregation and Cyclic Nucleotide Levels in Human Platelets", Journal of Cardiovascular Pharmacology, vol. 18(2): pp. 237–242.

Merkel, L. et al, "In vitro and in vivo interactions of nitrovasodilators and zaprinast, a cGMP–slective phosphodiesterase inhibitor", European Journal of Pharmacology, vol. 216 (1), pp. 29–35 (1992).

DeGaravilla, L. et al, "Zaptrinast, but no dipyridamole, reverses hermodynamic tolerance to nitroglycerin", Journal of Molecular and Cellular Cardiology, vol. 24, (Suppl. 3) S 37(1992).

DeGaravilla, L. et al, "Zaptrinast, but no dipyridamole, reverses hemodynamic tolerance to nitroglycerin in vivo", European Journal of Pharmacology, vol. 313 (1–2), pp. 89–96 (1996).

Pagani, E. et al, "Reversal of nitroglycerin tolerance in vitro by the cGMP–phosphodiesterase inhibitors zaprinast", European Journal of Pharmacology, vol. 243 (2), pp. 141–147 (1993).

Saecki, T. et al, "A selective type V phosphodiesterase inhibitor, E4021, dilates porcine large coronary artery", Journal of Pharmacology and Experimental Therapeutics, vol. 272 (2), pp. 825–831 (1995).

Szilvassy, Z. et al, "Cicletanine reverses vascular tolerance to nitroglycerin. A comparison with Zaprinast"Journal of Molecular and Cellular Cardiology, vol. 28(5), A97 (1996).

Dreyer, E. et al, "Excitatory aminoacides in glaucoma: a potentially novel etiology of neuronal loss in this optic neurophathy", Society for Neuroscience, Abstracts, vol. 18, No. 1/02, p. 439 (1992).

Xuan, B. et al., "Effects of crocin analogs on ocular blood flow and retinal function", Biosis Abstract PREV199900260815 & J. Ocular Pharm. and Therap. 15(2), 143–152 (Apr. 1999).

Bruckner, Ost. Arzteztg. 33/22, 1221–1236 (1978).

Enoksson, S. et al, "Various phosphodesterase subtypes mediate the in vivo antilipolytic effect of insulin on adipose tissue and skeletal muscle in man", Diabetologia, vol. 41, No. 5, pp. 560–568—Biosis Abstract Prev 199800273294 (May 1998).

Beers, et al, The Merck Manual of Diagnosis and Therapy, Merck Research Laboratories (1999), Whitehouse Station, NJ, Chapter 99—Retinal Disorders, pp. 729–738 (1999).

Jonas, J. et al., "Influence of experimental chronic high–pressure glaucoma on age–related macular degeneration in Rhesus monkeys", Invest. Ophthalmol. Vis. Sci., vol. 41(1), p. 2972 (2000).

Teichmann, K., "Treatment of macular degeneration, according to Bangerter", Eur. J. Med. Res., vol. 2(10), p. 445–454 (1997).

Abrams, D. et al, "Sildenafil as a selective pulmonary vasodilator in childhood primary pulmonary hypertension", Heart, vol. 84(2): E4 (Aug. 2000).

Alz, A. et al, "Sildenafil ameliorates effects of inhaled nitric oxide withdrawal", Anesthesiology, vol. 91, No. 1, pp. 307–310 (Jul. 1999).

Bigatello, L., "Strategies to enhance the efficacy of nitric oxide therapy", Respiratory Care, vol. 44, No. 3, pp. 331–339 (1999).

Elizabeth Palmer, et al., "Making the love drug", Chemistry in Britain, vol. 35, No. 1, Jan. 1999, pp. 24–26.

*Pfizer Limited and Laboratories Pfizer v. Eli Lilly* do Brasil, Inhibitory Action, Judiciary Section of the Safe of Rio de Janeiro, Case N#2004–002–042744–9, May 20, 2008.

Kahn, Michael, et al., "Horny Goat Weed may offer viagra alternative–study", Reuters Business & Finance, Sep. 29, 2008.

Feldman et al., Impotence and Its Medical and Psychological Correlates, The Journal Of Urology, vol. 151, pp. 54–61, (Jan. 1994).

Burchardt et al., Hypertension is Associated with Severe Erectile Dysnfunction The Journal of Urology, vol. 164, pp. 1188–1191, (Oct. 2000).

Declaration of Peter Ellis, (Aug. 23, 2000).

"Impotence: NIH Consensus Conference", Journal Am. Med. Assoc., Jul. 7, 1993, pp. 83–90, 270(1).

"Impotence: NIH Consensus Development Conference Statement", *Int. J. Impotence Res.,* vol. 5, pp. 181–199 (1993).

1992 Physician's Desk Reference, p. 1099 (1992).

Abrams, et al., "Sildenafil as a selective pulmonary vasodilator in childhood primary pulmonary hypertension", Heart, Aug. 2000, pp. E4, 84(2).

Allenby et al. 1991. Pentoxifylline In the Treatment of Vascular Impotence—Case Reports. Angiology 42: 418–420.

Ambrus et al. 1979. Studies on Vasoocclusive Crisis of Sickle Cell Disease, I. Effect of Pentoxifylline. Journal of Medicine. vol. 10, No. 6, pp. 445–456.

Anderson, et al., "Interactions Between Isoprenaline, Sodium Nitroprusside, and Isozyme–Selective Phosphodiesterase Inhibitors on ADP–Induced Aggregation and Cyclic Nucleotide Levels in Human Platelets", Journal of Cardiovascular Pharmacology, 1991, pp. 237–242, 18(2).

Andersson, et al., "Physiology of Penile Erection", Physiological Reviews, Jan. 1995, pp. 191–236, vol. 75(1).

Argel et al. 1980. Effect of Phosphodiesterase Inhibitors on Heart Contractile Behaviour, Protein Kinase Activity and Cyclic Nucleotide Level. Journal of Molecular and Cellular Cardiology. vol. 12(10), pp. 939–954.

Arnold, et al., "Pharmacopoeia of Traditional Medicine in Venda", Journal of Ethnopharmacology, 1984, pp. 35–74, vol. 12.

Aronson, et al., "*The mediator of human corpus cavernosum Relaxation is Nitric Oxide*", Journal of Urology, 145: Abstract 516 (in April issue) (1991).

Aronson, et al., "*The role of nitric oxide and cyclic GMT—in mediating pelvic nerve stimulation induced erections in dogs*", Journal of Urology, 147($4^{th}$ Supplement):454A (1992).

Atz, et al., "Sildenafil ameliorates effects of inhaled nitric oxide withdrawal", Anesthesiology, Jul. 1999, pp. 307–310, 91(1).

Australian Patent (Ellis et al.) acceptance No. 676571 and file history.

Australian Patent No. 6797394 (Ellis, et al., published Jan. 3, 1995).

Blakiston's Gould Medical Dictionary (Fourth Edition), including p. 343.

Ballard, et al, "Effects of Sildenafil on the Relaxation of Human Corpus Cavernosum Tissue in Vitro and on the Activites of Cyclic Nucleotide Phosphodiesterase Isozymes", *Journal of Urology*, vol. 159, pp. 2164–2171 (1998).

Bancroft, et al., "*Distress about sex: A national survey of women in heterosexual relationships*", Archives of Sexual Behavior, 32(3);193–208 (2003).

Bansal, "Sexual Dysfunction In Hypertensive Men, A Critical Review of the Literature", Hypertension, 1988, pp. 1–10, 12(1).

Barbier, et al., European Journal of Pharmacology, vol. 210, No. 3, "Effect of 3–isobutyl–1–methylxanthine and zaprinast on nonadrenergic non–cholinergic relaxation in the rat gastric fundus", pp. 315–323. 1992.

Basson, et al, "Report of the International Consensus Development Conference on Female Sexual Dysfunction: Definitions and Classifications", *J. Urol.*, vol. 163(3), p. 888 (2000).

Basson, et al., "*Sexual psychophysiology and effects of sildenafil citrate in oestrogenised women with acquired genital arousal disorder and impaired orgams: a randomised controlled trial*", Br. J. Obstet. Gynaecol., 110:1014–1024 (2003).

Beano, JA, "*Cyclic nucleotide phosphodiesterases: functional implications of multiple isoforms*", Physiological Reviews, 75(4):725–748 (1995).

Beavo et al. 1994. Multiple cyclic nucleotide phosphodiesterases. Molecular Pharmacology 46:399.

Beavo JA and Reifsnyder DH. 1990. Primary Sequence of Cyclic Nucleotide Phosphodiesterase Isozymes and the Design of Selective Inhibitors. TIPS 11:150–155.

Beavo, "Cyclic Nucleotide Posphodiesterases: Functional Implications of Multiple Isoforms", Physiological Reviews, 1995, pp. 725–748, 75(4).

Beavo, et al., "Multiple Phosphodiesterase Isoenzymes: Background, Nomenclature and Implications" in *Cyclic Nucleotide Phosphodiesterases: Structure, Regulation and Drug Action*, vol. 2, *Wiley Series on Molecular Pharmacology of Cell Regulation*, pp. 3–15 (1990).

Beavo, J., "*Multiple isozvmes of cyclic nucleotide phosphodiesterase*", Advances in Second Messenger and Prot. Phosphoprotein Research, 22: 1–38 (1988).

Bensky, Dan, Gamble, Andrew and Kaptchuk, Ted: "Chinese Medicine Materia Medica"Eastland Press, 1986.

Berman, et al., "*Safety and efficacy of sildenafil citrate for the treatment of female sexual arousal disorder: A double–blind placebo controlled study*",Journal of Urology, 170:2333–2338 (2003).

Bigatello, et al., "Strategies to enhance the efficacy of nitric oxide therapy", Respiratory Care, 1999, pp. 331–339, 44(3).

Bivalacqua, et al., "Pharmacotherapy for Erectile Dysfunction", Trends In Pharmacological Sciences, 2000, pp. 484–489, vol. 2.

Boolell et al. 1996. Sildenafil: an orally active type 5 cyclic GMP–specific phosphodiesterase inhibitor for the treatment of penile erectile dysfunction. International Journal of Impotence Research v.8: 47–52.

Bowman and Drummond, "Cyclic GMP Mediates Neurogenic Relaxation in the Bovine Retractor Penis Muscle", British Journal Pharmacology, 1984, pp. 665–674, 81(4).

Boyce, et al., Clinical Therapeutics, vol. 23 No. 1, "Sildenafil citrate: a therapeutic update", pp. 2–23. 2001.

Brock et al., "Impotence: A Patient's Goal Directed Approach", Urology Monograph, pp. 99–110 1992.

Brock, "Oral Phentolamine (Vasomax)", Drugs of Today, 2000, pp. 121–124, 36(2–3).

Budzik, et al., Biochemcal and Biophysical Research Commnications, vol. 144, No. 1, "Divergence of ANF analogs in smooth muscle cell cGMP response and aorta vasorelaxation: evidence for receptor subtypes", pp. 422–430. 1987.

Bush P, Aronson WJ, Buga GM, Rajfer J, and Ignarro L. 1992. Nitric Oxide is a Potent Relaxant of Human and Rabbit Corpus Cavernosum. J. Urology 147(6): 1650 (Jun. 1992).

Bush PA, Aronson WJ, Rajfer J, Buga GM and Ignarro LJ. Comparison of Nonadrenergic Noncholinergic– and Nitric Oxide–mediated Relaxation of Corpus Cavernosum. Int. J. Impotence Res. vol. 4, pp. 85–93, 1992.

Bush PA, Gonzalez NE and Ingarro LJ. Biosynthesis of nitric oxide and citrulline from L–arginine by constitutive nitric oxide synthase present in rabbit corpus cavernosum. Biochem. Biophys. Res. Commun. 186(1):308–314. Jul. 1992.

Bush, "*The role of/he L–arginine–nitric oxide–cyclic GMP pathway in relaxation of corpus cavernosum smooth muscle*", a Ph.D. dissertation, University of Californai at Los Angeles (1993).

Bush, et al., "Comparison of nonadrenergic, noncholinergic– and nitric oxide–mediated relaxation of corpus cavernosum", Int. J. Impotence Res., 1992, pp. 85–93, vol. 4.

Bush, et al., "Nitric Oxide is a Potent Relaxant of Human and Rabbit Corpus Cavernosum", The Journal of Urology, 147:1650–1655 (1992).

Bush, et al., The L–arginine–nitric oxide–cyclic GMP pathway mediates inhibitory nonadrenergic–non–cholinergic neurotransmission tn the corpus cavernosum of human and rabbit. Circulation 1993:87 [suppl V]:V30–V32.

Campbell, et al. PCT/EP95/04066 published as WO 96/16644, "cGMP–PDE Inhibitors for the Treatment of Erectile Dysfunction", Published: Jun. 6, 1996 (Pfizer) and file history (Patent only not file history).

Campbell, S. F., Clinical Science, vol. 99, "Science, art and drug discovery: a S.F. personal perspective", pp. 255–260. 2000.

Carrier, et al. Pathophysiology of Erectile Dysfunction. Urology. vol. 42, pp. 468–481, 1993.

Carrier, et al., "Erectile Dysfunction", Endocrinology and Metabolism Clinics of North America, 1994, pp. 773–782, 23(4).

Cazzulani, et al., "Pharmacological Activities of the Main Metabolite of Flavoxate 3–Methylflavone–8–carboxylic Acid", Arzneimittel–Forschuna/Drug Res., 1988, pp. 379–382, vol. 38(I), No. 3.

Chancellor, et al., "Prospective Comparison of Topical Minoxidil to Vacuum Constriction Device and Intracorporeal Papaverine Injection in Treatment of Erectile Dysfunction Due to Spinal Cord Injury", Urology, Mar. 1994, pp. 365–369, 43(3).

Charbonneau, H. "Structure–Function Relationships Among Cyclic Nucleotide Phosphodiesterases", In Cyclic Nucleotide Phosphodiesterases: Structure, Regulation, and Drug Action (Beavo, J. & Houslay, M.D., eds), John Wiley & Sons, New York, pp. 267–296. 1990.

Cheitlin et al., Journal of the American College of Cardiology, vol. 33, al. "ACC/AHA expert consensus document. Use of sildenafil (Viagra) in patients with cardiovascular disease. American College of Cardiology/American Heart Association", pp. 273–282. 1999.

Christensen & Torphy, "Isozyme–Selective Phosphodiesterase Inhibitors as Antiasthmatic Agents", Annual Reports in Medicinal Chemistry, 1995, pp. 185–194, Chapter 19, vol. 29.

Conti et al. Endocrine Reviews, vol. 12, No. 3, "Hormonal regulation of cyclic nucleotide phosphodiesterases", pp. 218–234 1991.

Corbin et al., International Journal of Clinical Practice, vol. 56 No. 6, "Pharmacology of phosphodiesterase–5 inhibitors", pp. 453–459. 2002 Jul./Aug.

Corbin et al., Urology, vol. 56 No. 3, "Effects of sildenafil on cAMP and cGMP levels in isolated human cavernous and cardiac tissue", p. 545. 2000.

Corbin, et al., Current Medical Research and Opinion, vol. 19 No. 8, "Sildenafil citrate does not affect cardiac contractility in human or dog heart", pp. 747–752. 2003.

Corbin, et al., Journal of Biological Chemistry, vol. 274 No. 20, "Cyclic GMP phosphodiestrase–5: target of sildenafil", pp. 13729–13732. 1999.

Cortijo, et al. "Investigation into the Role of Phosphodiesterase IV in Bronchorelaxation, Including Studies with Human Broncnus", British Journal of Pharmacology, 108:562–568 (1993).

Coulson, et al., Nature, vol. 265, No. 5594, "Interrelationship of cyclic nucleotides and anaphylactic reactions," pp. 545–547. 1977.

Courtois, et al., "Clinical approach to erectile dysfunction in spinal cord injured men. A review of clinical and experimental data", Paraplegia, 1995, pp. 628–635, vol. 33.

DasGupta, et al., "Efficacy of Sildenafil in the treatment of female sexual dysfunction due to multiple sclerosis", Journal of Urology, 171:1189–1193 (2004).

De Boer et al., Human Bronchial Cyclic Nucleotide Phosphodiesterase Isoenzymes: Biochemical and Pharmacological Analysis Using Selective Inhibitors. British Journal of Pharmacology. vol. 106, pp. 1028–1034, 1992.

December 1992, the NIH Conference Statement on Impotence (Int. J. Impotence Res. (1993) 5, 181–199.

DeGaravilla, et al., "Zaprinast but not dipyridamole reverses hemodynamic tolerance to nitroglycerin", Journal of Molecular and Cellular Cardiology, 1992, p. S37, Abstract P96, vol. 24. Suppl. 3.

DeGaravilla, et al., "Zaprinast, but not dipyridamole, reverses hemodynamic tolerance to nitroglycerin in vivo", European Journal of Pharmacology, 1996, pp. 89–96, 313(1–2).

Derry, et al., "Sildenafil (Viagra™): A double–blind, placebo controlled, single–dose, two–way crossover study in men with erectile dysfunction caused by traumatic spinal cord injury", Journal of Urology, 1997, p. 181, 157(4) Suppl.

Derry, et al., "Sildenafil (Viagra™): An oral treatment for men with erectile dysfunction caused by traumatic spinal cord injury—A 28–day, double–blind, placebo controlled, parallel–group, dose–response study", Journal of the Neurological Sciences, 1997, p. S270, vol. 150.

Derry, et al., "Silldenafil (Viagra™): An oral treatment for men with erectile dysfunction caused by traumatic spinal cord injury: A 28–day, double–blind, placebo controlled, parallel–group, dose–response study", Neurology, Mar. 1997, pp. A215, 48(2) Suppl. 2.

Editors, "Pfizer to end tests of Viagra for women", Drug Week, Mar. 19, 2004, Expanded Reporting Section, p. 466.

Elsner, et al., Journal of Cardiovascular Pharmacology, vol. 14, No. 2, "Hemodynamic, renal, and hormonal effects of 8–Br–cyclic GMP in conscious dogs with and without congestive heart failure", pp. 241–247. 1989.

Enoksson, et al., "Various phosphodiesterase subtypes mediate the in vivo antilipolytic effect of insulin on adipose tissue and skeletal muscle in man", Diabetologia, May 1998, pp. 560–568, 41(5), Biosis Abstract Prev. 199800273294.

EP 0 214 708 (p. 68, vol. 2, lines 40–42, and table 9; p. 68, col. 134, lines 30–42).

EP 0 293 063 (p. 2, lines 4–5 and pp. 8–9; p. 3, lines 9–11; p. 3, lines 34–37).

EP 0 319 050 (p. 2, lines 45–46; p. 47, lines 55–59).

EP 0 347 027 (p. 9, lines 51–53; p. 4, lines 54–55; p. 5, lines 23–24).

EP 0 347146 (p. 11, lines 28–30; p. 5, line 48; p. 6, line 19).

EP 0 349,239 (p. 3, lines 3–4; p. 4, line 34; p. 5, line 5).

EP 0 351058 (p. 11, line 55 to p. 12, line 2; p. 5, line 20; p. 5, line 47).

EP 0 352 960 (p. 6, line 56 to p. 7, line 3; p. 3, lines 39–41; p. 4, lines 8–11).

EP 0 371731 (p. 6, lines 10–14; p. 3, lines 27–28; p. 3, lines 56–58).

EP 0 395 328 (p. 8, lines 23–27; p. 4, lines 36–37; p. 5, lines 4–7).

EP 0 428 268 (p. 9, lines 28–33; p. 4, lines 44–45; p. 5, lines 13–16).

EP 0 526 004 (p. 8, line 54; p. 9, lines 11–12).

EP 0 579496 (pp. 17–18; p. 19, lines 30–33; p. 19, lines 34–36).
EP 0 607 439 (p. 39, lines 50–51; p. 40, lines 8–9; p. 40, lines 13–15).
EP 0 664289 (p. 6, line 43; p. 12, lines 30–33).
EP 0 668 280 (p. 2; p. 23, lines 15–17; p. 23, line 26).
EP 0 669 324 (p. 1; p. 11, lines 52–53; p. 11, lines 57–58).
EP 0 686 625 (p. 1; p. 27, lines 22–23; p. 27, lines 26–27).
EP 0400 583 (p. 11, line 20).
EP 0400 799 (p. 3, line 3; p. 4, lines 7–9; p. 4, lines 34–37).
EP 0442204 (p. 3, line 4; p. 4, lines 43–44; p. 5, lines 9–12; p. 10, lines 50–51).
EP 0463 756 (p. 7, lines 7–8; p. 7, lines 35–36; p. 7, lines 24–26).
EP 0636 626 (p. 2, para 2, lines 1–2; p. 6, lines 40–41; p. 6, lines 28–31).
EP 0640 599 (p. 3, lines 14–15; p. 33, lines 5–8; p. 33, lines 9–11).
EP–A–0 162 715, Nakagawa, et al., Nov. 27, 1985.
EP–A–0 201 188, Hamilton, Dec. 17, 1986.
EP–A–0 214 708, Kaneko, et al., Mar. 18, 1987.
EP–A–0 277 042, Takasima, et al., Aug. 3, 1988.
EP–A–0 293 063, Coates, Nov. 30, 1988.
EP–A–0 319 050, Kaneko, et al., Jun. 7, 1989.
EP–A–0 347 027, Coates, et al., Dec. 20, 1989.
EP–A–0 347 146, Coates, et al., Dec. 20, 1989.
EP–A–0 349 239, Coates, Jan. 3, 1990.
EP–A–0 351 058, Coates, et al., Jan. 17, 1990.
EP–A–0 351 960, Coates, Jan. 31, 1990.
EP–A–0 371 731, Coates, et al., Jun. 6, 1990.
EP–A–0 395 328, Coates, et al., Oct. 31, 1990.
EP–A0 400 583, Davey, May 12, 1990.
EP–A–0 400 799, Coates, May 12, 1990.
EP–A–0 428 268, Coates, et al., May 22, 1991.
EP–A–0 442 204, Coates, Aug. 21, 1991.
EP–A–0 463 756, Bell, et al., Jan. 2, 1992.
EP–A–0 526 004, Bell, et al., Feb. 3, 1993.
EP–A–0 579 496, Lee, et al., Jan. 19, 1994.
EP–A–0 607 439, Takase, et al., Jul. 22, 1994.
EP–A–0 636 626 Feb. 1, 1995 Dumaitre.
EP–A–0 640 599, Lee, et al., Mar. 1, 1995.
EP–A–0 664 289 Jul. 26, 1995 Naef.
EP–A–0 668 280, Machii, et al., Aug. 23, 1995.
EP–A–0 669 324 Aug. 23, 1995 Takase.
EP–A–0 686 625 Dec. 13, 1995 Ozaki.
EP–A–0201188.
EP–A–O 409 254, Shirai, et al., Jan. 23, 1991.
EP–B–0–162–715 1985.
Erneux, et al., Molecular Cellular Endocrinology, vol. 43, "A mechanism in the control of intracellular cAMP level: the activation of a calmodulin–sensitive phosphodiesterase by a rise of intracellular free calcium", pp. 123–134. 1985.
European Patent 0,463,756 (Bell 1) (and corresponding patent application).
European Patent 0,526,004 (Bell 2) (and coresponding patent application).
European Patent No. 0162715 (Nakagawa, et al., 1985).
European Patent No. 0201188, published on Dec. 7, 1986.
European Patent No. 0214708 (Kaneko, et al., 1987).
European Patent No. 0293063 (Coates, 1988).
European Patent No. 0319050 (Kaneko, 1989).
European Patent No. 0347027 (Coates, et al., 1989).
European Patent No. 0347146 (Coates, 1989).
European Patent No. 0349239 (Coates, Jan. 3, 1990).
European Patent No. 0351058 (Coates, Jan. 17, 1990).
European Patent No. 0352960 (Coates, 1990).
European Patent No. 0371731 (Coates, 1990).
European Patent No. 0395328 (Coates, Oct. 31, 1990).
European Patent No. 0400583 (Davey, May 12, 1990).
European Patent No. 0400799 (Coates, May 12, 1990).
European Patent No. 0428268 (Coates, May 22, 1991).
European Patent No. 0442004 (Coates, Aug. 21, 1991).
European Patent No. 0463756, published on Jan. 2, 1992.
European Patent No. 0526004, published on Feb. 3, 1993.
European Patent No. 0607439 (Takase, et al., Jul. 22, 1994).
European Patent No. 0636626 (Dumaitre, et al., Feb. 1, 1995).
European Patent No. 0640599 (Lee, et al., Mar. 1, 1995).
European Patent No. 0664289 (Naef, Jul. 26, 1995).
European Patent No. 0668280 (Machii, et al., Aug. 23, 1995).
European Patent No. 0669324 (Takase, et al., Aug. 30, 1995).
European Patent No. 0686625 (Ozaki, et al., Dec. 13, 1995).
European Patent No. 0702555 and file history Mar. 11, 1998 (Patent only not file history).
European Patent No. EP0579496 (Lee, et al., Jan. 19, 1994).
Fernandes LB, Ellis JL, and Undern BJ. 1994. Potentiation of nonadrenergic noncholinergic relaxation of human isolated bronchus by selective inhibitors of phosphodiesterase isozymes. Am. J. Respir. Crit. Care Med. 150:1384–1390.
Fink, "Trazodone for erectile dysfunction: a systematic review and meta analysis," British Journal of Urology, Sep. 2003 pp. 441–446, 92(4), and in particular the prior art clinical studies discussed therein including at p. 443, and the related footnotes.
Fishman, "Treating Erectile Dysfunction New Approaches", Drug Therapy, Aug. 1989, pp. 102–111, 19(8).
Foreman and Wernickle, "Approaches for the Development of Oral Drug Therapies for Erectile Dysfunction", Seminars in Urology, 1990, pp. 107–112, VIII(2).
Gillespie, et al., "*Inhibition and Stimulation of Photoreceptor Phosphodiesterases by Dipyridamole and M&B 22,948*", Molecular Pharmacology, 36(5):773–781, 789 (1989).
Gillespie, P.G. "Cyclic nucleotide phosphodiesterases: structure, regulation and drug action. Phosphodiesterases in visual transduction by rods and cones", pp. 163–184. 1990.
Gillies, et al., International Journal of Cardiology, vol. 86. "Coronary and systemic hemodynamic effects of sildenafil citrate: from basic science to clinical studies in patients with cardiovascular disease", pp. 131–141. 2002.
Gingell & Lockyer, "Emerging Pharmacological Therapies for Erectile Dysfunction", Exp. Opin. Ther. Patents, 1999, pp. 1689–1696, 9(12).
Gomella, "Editorial: Impotence–Defining the Role of Minimally Invasive Therapy", Journal of Urology, 1996, p. 147, vol. 155.
Grant, et al., Biochemistry, vol. 23, "Purification and Characterization of a Human Platelet Cyclic Nucleotide Phosphodiesterase", pp. 1801–1807, 1984.
Greenberg, et al., Neuropharmacology, vol. 17, "Enzymatic regulation of the concentration of cyclic GMP mouse brain", pp. 737–745. 1978.
Gregoire, "*Viagra: on release*", British Medical Journal, 317:759–760 (1998).
Gruetter, et al., *J. Cyclic Nucleotide Res.*, vol. 5, pp. 211–224 (1979).

Grunwald, et al. American Journal of Ophthamology, vol. 132, "Acute effects of sildenafil citrate (Viagra) on intraocular pressure in openangle glaucoma", pp. 872–874. 2001.

Guimaraes, et al. Arquivos Brasileiros de Cardiologia, vol. 73 No. 6, "Use of Sildenafil in Patients with Cardiovascular Disease", pp. 515–526. 1999.

Hagiwara, et al., Journal of Pharmacology and Experimental Therapeutics, vol. 228, No. 2, "Effect of 1–(3–chloroanilino)–4–phenylphthalazine (MY–5445) ,a specific inhibitor of cyclic GMP phosphodiesterase, on human platelet aggregation", pp. 467–471. 1984.

Hall et al., Biochemical Pharmacology, vol. 43, No. 1, "Effects of isozyme selective phosphodiesterase inhibitors on bovine tracheal smooth muscle tone", pp. 15–17. 1992.

Hamilton, H., EP–A–O 201 188, "*5–Substituted pyrazolo not 4,3–d pyrimidine–7–ones, process for preparing the compounds and pharmaceutical compositions comprising the compounds*" (1986).

Hammerschmidt, et al. Pentoxifylline inhibits granulocyte and platelet function, including granulocyte priming by platelet activating factor. 1988 Aug. J. Lab. Clin. Med. 112(2):254.

Hatzichristou DG. 2002. Sildenafil citrate: lessons learned from 3 years of clinical experience. Int J Impot Res 14 (Suppl 1):S43–S52, 2002.

Heaton, et al., "Recovery of Erectile Function by the Oral Administration of Apomorphine", Urology 1995, pp. 200–206, 45(2).

Hermann et al., Circulation vol. 100 No. 18. "Systemic, pulmonary, and coronary hemodynamics and platelet effects of oral sildenafil citrate (Viagra) in men with severe coronary artery disease." p. 1–378 1999.

Hidaka, et al., Biochimica et Biophysica Acta vol. 429, No. 2, "Human blood platelet 3':5'–cyclic nucleotide phosphodiesterase", pp. 485–497. 1976.

Hidaka, et al., Trends in Pharmacological Sciences, "Selective inhibitors of three forms of cyclic nucleotide phosphodiesterases", pp. 237–239 1984.

Hoey M and Houslay MD. 1990. Identification and selective inhibition of four distinct soluble forms of cyclic nucleotide phosphodiesterase activity from kidney. Biochemical Phannacology 40(2): 193–202.

Holbrook, et al., *British Journal ofPharmacology*, vol. 103, "Effects of zaprinast and rolipram on platelet aggregation and arrhythmias following myocardial ischaemia and reperfusion in anaesthetized rabbits", pp. 1973–1979. 1991.

Holden, et al. "Gel Electrophoresis of Mucous Glycoproteins. II. Effect of Physical Deaggregaton and Disulfide–Bond Cleavage", Biochemistry, vol. 10, pp. 3110–3113. 1971.

Holmquist et al. 1991. Effects of the nitric oxide synthase inhibitor Ng–nitro–L–arginine on the erectile response to cavernous nerve stimulation in the rabbit. Acta. Physiol. Scan. 143:299–304.

Holmquist, et al., "Actions of 3–Morphollnosydnonimin–(SIN–1) on Rabbit Isolated Penile Erectile Tissue", Journal of Urology, 1993, pp. 1310–1315, vol. 150.

Ignarro LJ, Buga GM, Wood KS, Byrns RE, and Chaudhuri G. 1987. Endothelium–derived relaxing factor produced and released from artery and vein is nitric oxide. Proc. Nat. Acad. Sci. USA 84:9265–9269.

Ignarro LJ, Burke TM, Wood KS, Wolin MS, and Kadowitz. PJ. 1984. Association between cyclic GMP acculumation acetylcholine–elicited relaxation of bovine intrapulmonary artery. J. Pharm. and Exp. Ther. 228(3):682.

Ignarro LJ, Bush PA, Buga GM, Wood KS, Fukuto JM, Rajfer J. 1990. Nitric Oxide and Cyclic GMP Formulation Upon Electrical Field Stimulation Cause Relaxation of Corpus Cavernosum Smooth Muscle. Biochemical and Biophysical Research Communications. vol. 170, No. 2, pp. 843–850.

Ignarro LJ, Byrns RE and Wood KS. 1986. Endothelium–dependent modulation of cGMP levels and intrinsic smooth muscle tone in isolated bovine intrapulmonary artery and vein. Circulation Research 60(1):82.

Ignarro LJ. 1989. Biological Actions and properties of endothelium–derived nitric oxide formed and released from artery and vein. Circulation Research 65(1):1–21. Jul. 1989.

Ignarro LJ. 1990. Biosynthesis and metabolism of endothelium–derived nitrix oxide. Annu. Rev. Pharmacol. Toxicol. 30:535–560.

Ignarro, et al., "Nitric Oxide and Cyclic GMP Formulation Upon Electrical Field Stimulation Cause Relaxation of Corpus Canvernosum Smooth Muscle", Biochemical and Biophysical Research Communications, 1990, pp. 843–850, 170(2).

Ignarro, "Nitric Oxide: A Unique Endogenous Signaling Molecule In Vascular Biology", Bioscience Reports, 1999, pp. 51–71, 19(2).

Ignarro, et al., 1990, *"Nitric Oxide and Cyclic GMP Formulation Upon Electrical Field Simulation Cause Relaxation of Corpus Cavemosum Smooth Muslce"*, Biochemical and Biophysical Research Communications, 170(2):843–850.

Imai, et al., Comparative Biochemistry and Physiology Part B, vol. 124, "Comparison of phosphodiesterase isozymes in rodent parotid glands", pp. 397–403. 1999.

*Impotence, NIH Consensus Statement,* vol. 10, No. 4, pp. 1–33 (Dec. 7–9, 1992).

Impotence. NIH Consensus Statement 1992, Dec. 7–9, 1992, pp. 1–33 10(4).

Impotence: NIH Consensus Conference. Journal Am. Med. Assoc. vol. 270, pp. 83–90, 1993.

International PCT Application WO 89/10123, Ruffmann, Nov. 2, 1989.

International PCT Application WO 91/19717, Neustadt, et al., Dec. 26, 1991.

International PCT Application WO 93/12095, Terret, Jun. 24, 1993.

International PCT Application WO 93/24109, Bhardwaj, et al., Dec. 9, 1993.

International PCT Application WO 94/19351, Tulshian, Sep. 1, 1994.

International PCT Application WO 94/22855 Oct. 13, 1994 Takase.

International PCT Application WO 94/28902 A, Ellis, et al., Dec. 22, 1994.

International PCT Application WO 95/19978, Daugan, Jul. 27, 1995.

International PCT Application WO 96/16644, Campbell, et al., Jun. 6, 1996.

International PCT Application WO 96/16657, Campbell, Jun. 6, 1996.

International PCT Application WO 98/37894, Schudt, Sep. 3, 1998.

International PCT Application WO 98/49166, Bunnage, et al., Nov. 5, 1998.

International PCT Application WO 99/21831, Oku, et al., May 6, 1999.

International PCT Application WO 99/54333, Bunnage, et al., Oct. 28, 1999.

Jackson & Lue, "Erectile Dysfunction: Therapy Health Outcome", Urology, 1998, pp. 874–882, vol. 51.

Jackson, et al., American Journal of Cardiology, vol. 83(suppl. 5A), "Effects of sildenafil cirtrate on human hemodynamics", pp. 13C–20C. 1999.

Japanese Patent No. 7–506838 (Pfizer, 1995).

Jiang, et al., Journal of Biological Chemistry, vol. 267, No. 2, "Direct evidence for cross–activation of cGMP–dependent protein kinase by cAMP in pig coronary arteries", pp. 1015–1019 1992.

Jonas, J., et al., "Influence of Experminet Chronic High–Pressure Glaucoma on Age–Resisted Macular Degeneration in Rhesus Monkeys", Invest Ophthalmol. Vis. Sci., 2000, p. 2972–2977, 41(40).

Journal Am. Med. Assoc., 1993, *"Impotence: NMI Consensus Conference"*, 270:83–90.

JP 7–506838 (Pfizer), Jul. 27, 1995.

Kaneko, et al. EP 0214708 "Griseolic acid derivatives, their preparation and their use", Mar. 18, 1987.

Kaplan, et al., "Safety and Efficacy of Sildenafil in Postmenopausal Women with Sexual Dysfunction". Urology, 1999, pp. 481–486, 53(3).

Kawanishi, et al., "Double–blind trial of oral prostaglandin $E_1$ on Impotence", Journal of Japanese Society of Urology, 1992, pp. 1655–1661, 83(10).

Kim N., et al., Jul. 1991. A nitric oxide–like factor mediates nonadrenergic–noncholinergic neurogenic relaxation of penile corpus cavermosum smooth muscle. The Journal of Clinical Investigation 88: 112–118.

Kincaid, et al., Proceedings of the National Academy of Sciences (U.S.A.), vol. 84, "Differential—localization of calmodulin–dependent enzymes in rat brain: Evidence for selective expression of cyclic nucleotide phosphodiesterase in specific neurons", pp. 1118–1122. 1987.

Kirby, et al., "Medical Treatment of Erectile Dysfunction", Eds., Impotence: Diagnosis and Management of MED. Oxford: Butterworth–Heinemann Ltd., 1991, pp. 149–151, Chapter 16.

Kling, J. Modern Drug Discovery, vol. 1(2), "From Hypertension to angina to Viagra", pp. 31,33,34,36,38. 1998.

Knispel, et al., *International Journal of Impotence Research,* Supplement 1, p. 13 (Sep. 1995).

Komas et al., British Journal of Pharmacology, vol. 104, No. 2, "Endothelium–dependent and independent relaxation of the rat aorta by cyclic nucleotide phosphodiesterase inhibitors", pp. 495–503. 1991.

Korenman SG et al. Apr. 13, 1998. Treatment of Vasculogenic Sexual Dysfunction with Pentoxiffylline. Clin. Res., 36(1), p. 123A, (Absr.).

Krane, et al., "Medical Progress–Impotence", New England Journal of Medicine, 1989, pp. 1648–1659, 321(24).

Lee et al., Drug Development Research, vol. 23, No. 2, "Comparative hemodynamic and renal effects of the low Km cGMP phosphodiesterase inhibitors cicletanine and zaprinast in anesthetized dogs", pp. 127–144. 1991.

Lee SJ, Konishi Y, Yu DT, Miskowski TA, Riviello CM, Macina OT, Frierson MR, Kondo K, Sugitani M, Sircar JC and Blazejewski KM. 1995. J. Med. Chern. 38:3547–3557.

Lepore, et al., Circulation vol. 100 No. 18, Sildenafil is a pulmonary vasodilator which augments and prolongs vasodilation by inhaled nitric oxide in patients with pulmonary hypertension. P.O–240. 1999.

Lerner, et al., 1993, "A *Review of Erectile Dysfunction: New Insights an More Questions"*, The Journal of Urology, 149:1246–1255.

Lin et al. The rabbit as an intracavernous injection study model. Urol. Res., vol. 24, pp. 27–32 1996.

Lue and tanagho, Physiology of Erection and Pharmacological Management of Impotence. Journal of Urology. 1987. 137:829.

Lue, "Topical and Oral Agents for Erectile Dysfunction", J. Formos. Med Assoc., 1999, pp. 233–241, 98(4).

Lue, et al., "Comparison of oral and intracavemosal vasoactive agents in penile erection", Int. Journal of Impotence Res., 2000, pp. S81–S88, vol. 12, Suppl. 1.

Lugnier, et al., Biochemical Pharmacology, vol. 39, No. 1, "Characterization of cyclic nucleotide phosphodiesterases from cultured bovine aortic endothelial cells", pp. 75–84. 1990.

Martindale Extra Pharmacopoeia (29th edition), 1989 including "zaprinast" p. 1423, Heading 14026–m, 1990.

Martindale Extra Pharmacopoeia, 1990, $29^{th}$ Edition, 1423, Heading 14026–m, 1989.

Maurice, D. H., International Journal of Impotence Research, vol. 16, Supplement 1, "Cardiovascular implications in the use of PDE5 inhibitor therapy", pp. S20–S23. 2004.

Maurice, et al., Molecular Pharmacology, vol. 37, No. 5, "Molecular basis of the synergistic inhibition of platelet function by nitrovasodilators and activators of adenylate cyclase: inhibition of cyclic AMP breakdown by cyclic GMP", pp. 671–681. 1990.

McAllister–Lucas, et al., Journal of Biological Chemistry, vol. 268 No. 30, "The structure of a bovine lung cGMP–binding, cGMP–specific phosphodiesterase deduced from a cDNA clone", pp. 22863–22873. 1993.

McMahon, et al, "Depressor and Natriuretic Effects of M&B 22,948 a Guanosine Cyclic 3',5'–Monophosphate–Selective Phosphodiesterase Inhibitor", *The Journal of Pharmacology and Experimental Therapy,* vol. 251, No. 3, pp. 1000–1005 (1990).

Meinhardt, et al., "The Influence of Medication on Erectile dysfunction", Int. J. of Impotence Res., 1997, pp. 17–26, vol. 9.

Merkel, et al., "In vitro and in vivo interactions of nitrovasodilators and zaprinast, a cGMP–selective phosphodiesterase inhibitor", European Journal of Pharmacology, 1992, pp. 29–35, 216(1).

Meyer et al. Intracavernous Application of SIN–1 in Rabbit and Man: Functional and Toxicological Results. Annals Urol., vol. 27, pp. 179–182 1993.

Moncada S, Palmer RM, Higgs EA. 1991. Nitric oxide: physiology, pathology, pathophysiology and pharmacology. Pharmacol. Rev., 43: 109–142.

Morales, et al., "Oral and Topical Treatment of Erectile Dysfunction", Urol. Clin. North AM., 1995, pp. 879–886, 22(4).

Morley J. 1993. Management of Impotence: Diagnostic Considerations and Therapeutic Options. Postgraduate Medicine 93(3): 65–72 (Feb. 15, 1993) ("Morley").

Morley, et al., "Female Sexuality", Med. Clin. A. Am., Sep. 2003, pp. 1077–1090, vol. 87.

Moynihan. "The making of a disease: female sexual dysfunction", British Medical Journal, Jan. 4, 2003, pp. 45–47, 326(7379).

Murad, "Drugs Used for the Treatment of Angina: Organic Nitrates, Calcium–Chanel, Blockers, and β–Adrenergic Antagonists", *Goodman & Gilman's. The Pharmacological Basis of Therapeutics,* (Eighth Edition), Chapter 32, pp. 764–783 (1990).

Murray, et al. Biochemical Society Transactions, vol. 20, "Inhibitors of cyclic nucleotide phosphodiesterases as therapeutic agents?", pp. 460–464. 1992.

Murray, et al., "Potential Use of Selective Phosphodiestrase Inhibitors in the Treatment of Asthma", New Drugs for Asthma Therapy, 1991, Birkhauser Verlag Basel, Agents and actions: Supplements, pp. 27–46, vol. 34.

Mustard, et al., Methods in Enzymology, vol. 169, "Isolation of human platelets from plasma by centrifugation and washing", pp. 3–11. 1989.

Nakatsu K and Diamond J. Role of cGMP in relaxation of Diamond vascular and other smooth muscle. Can J. Physiol. Pharmacol.; 67: 251–262, 1989.

Nandi JS, Nair KG and Deo S. 1980. Inhibition of cAMP phosphodiesterase in the rat heart by pentoxifylline–a new xanthine derivative. Advances in Myocardiology, vol. 1. p. 359.

Nicholson DC et al. 1991. Differential modulation of tissue function and therapeutic potential of selective inhibitors of cyclic nucleotide phosphodiesterase isoenzymes. Trends in Pharmacological Science 12: 19–27.

NIH Consensus Statement, 1992, *"Impotence"* 10(4):1–33

Noel No YuH Kim. Regulation of penile corpus cavernosum smooth muscle tone by nitric oxide. Dissertation for Doctor of Philosophy. 1991.

Opie, L.H., Cardiology, vol. 75, Suppl. 1, "Inodilation–The way ahead in the early therapy of congestive heart failure?", pp. 138–147. 1988.

Owen JA et al. 1989. Topical nitroglycerin: A potential treatment for impotence. J. Urol. 141 March.

Pagani, et al., "Reversal of nitroglycerin tolerance in vitro by the cGMP–phosphodiesterase inhibitor zaprinast", European Journal of Pharmacology, 1993, pp. 141–147, 243(2).

Palmer RMJ, Ferrige AG, and Moncada S. Nitric oxide release accounts for the biological activity of endothelium–derived relaxing factor. Nature 327: 524–526 (Jun. 11, 1987).

Palmer, "Making the Love Drug", Chemistry in Britain, Jan. 1999, pp. 24–26, 35(1).

Paris, et al., International Ophthalmology, vol. 23, "Sildenafil increases ocular perfusion", pp. 355–358. 2001.

*Physician's Desk Reference,* p. 1099 (1992).

Rajfer, "From the Lab to the Clinic", Journal of Urology, 1998, p. 1792, vol. 159.

Reid, et al., "Double Blind Trial of Yohimbine in Treatment of Psychogenic Impotence" Lancet. Aug. 1987, pp. 421–423, 22:2(8556).

Reiser, et al., The Effect of Zaprinast (M&B 22, 948, an Orally Absorbed Mast Cell Stabilizer) on Exercise–Induced Asthma in Children, *British Journal Dis. Chest,* vol. 80, pp. 157–163 (1986).

Riegger, et al., Circulation—Laboratory Investigation—Congestive Heart Failure, vol. 77, No. 2, "Atrial natriuretic peptide in congestive heart failure in the dog: plasma levels, cyclic guanosine monophosphate, ultrastructure of atrial myoendocrine cells, and hemodynamic, hormonal, and renal effects", pp. 398–406 1988.

Riley, "Oral treatments for erectile dysfunction", International Journal of STD & AIDS, 1996, pp. 16–18, vol. 7, Suppl. 3.

Riley, Ian J., Double Blind Trial of Yohimbine Hydrochloride in the Treatment of Erection Inadequacy, Sexual and Relationship Therapy, Jan. 1989, pp. 17–26, 4(1).

Robin JC and Ambrus JL. 1983. Studies on Osteoporoses. XI. Effects of a methylxanthine Derivative. Journal of Medicine 14(2):137.

Robison, AG, Journal of Japan Atherosclerosis Society, Symposium 10, A.G. Arterial Wall Metabolism and Atherosclerosis, vol. 17, No. 1, "On the regulation of vascular smooth muscle by cyclic nucleotides", pp. 39–43. 1989.

Rotella et al., "N–3–Substituted Imidazoquinazolinones: Potent and Selective PDES Inhibitors as Potential Agents for Treatment of Erectile Dysfunction", J. Med. Chem., pp. 1257–1263, vol. 43.

Sachse, et al., "Safety, Tolerability and Pharmacokinetics of BAY 38–9456 in Patients with Erectile Dysfunction", J. Urology, Tuesday, May 2, 2000, p. 204, vol. 163(4), Abstract 904, Supplement.

Saeki, et al., "Isolation of Cyclic Nucleotide Phosphodiesterase Isozymes from Pig Aorta", Biochemical Pharmacology, 1993, pp. 833–839, 46(5).

Saeki, et al., "A selective Type V Phosphodiesterase Inhibitor, E4021, Dilates Porcine Large Coronary Artery", Journal of Pharmacology and Experimental Therapeutics, 1995, p. 825–831, 272(2).

Saenz De Tejada, "Molecular Mechanism for the Regulation of Penile Smooth Muscle Contractility", Int. Journal of Impotence Res., 2000, pp. S34–S38. vol. 12, Suppl. 4.

Salonia, et al., European Urology. Supplement, vol. 1 No. 1, pp. 63 2002.

Schalcher, et al., Hypertension, Nov. 2002, "Interaction of sildenafil with cAMP–mediated vasodilation in vivo", pp. 763–767. 2002.

Schoeffter, et al., Role of cyclic AMP and cyclic GMP–phosphodiesterases in the control of cyclic nucleotide levels and smooth muscle tone in rat isolated aorta, Molecular Pharmacology 36(28): 3965–3972., 1987.

Semmler J, Wachtel H and Endres S. The specific type IV phosphodiesterase inhibitor rolipram suppresses tumor necrosis factor–β production by human mononuclear cells. Int. J. Immunopharmac. 15(3): 409–413. 1992.

Shahid, et al., British Journal of Pharmacology, vol. 104, No. 2, "The presence of five cyclic nucleotide phosphoiesterase isoenzyme activites in bovine tracheal smooth muscle and the functional effects of selective inhibitors", pp. 471–477. 1991.

Shen M, Chiang P, Yang B, Hong, C, Chen S. 1991. Pentoxifylline stimulates human sperm motility both in vitro and after oral therapy. Br. J. Clin. Pharmac. (1991),31 711–714.

Silver PJ, Pagani ED, Dundore RL, de Garavilla L, Chris Bode D, amd Bacon ER. 1998. Cardiovascular activity of WIN 65579, a novel inhibitor of cyclic GMP phosphodiesterase 5. Eur. J. Phannacol. 349:263–268.

Silver, et al., "Cyclic GMP Potentiation by WIN 58237, a Novel Cyclic Nucleotide Phosphodiesterase Inhibitor", J. Pharm. Exp. Therapeutics, 1994, pp. 1143–1149, 271(3).

Silver, et al. "Reversal of nitroglycerin tolerance by the cGMP phosphodiesterase inhibitor zaprinast", European Journal of Pharmacology, 1991, pp. 141–142, 199(1).

Silver, P. J., American Journal of Cardiology, vol. 63, "Biochemical aspects of inhibition of cardiovascular low (Km) cyclic adenosine monophosphate phosphodiesterase", pp. 2A–8A. 1989.

Sipski, et al., "Sildenafil Effects on Sexual and Cardiovascular Responses in Women with Spinal Cord Injury", Urology, Jun. 2000, pp. 812–815, 55(6).

Souness JE, Brazdil R, Diocee BK and Jordan R. 1989. Role of selective cyclic GMP phosphodiesterase inhibition in the myorelaxant actions of M&B 22,948, MY–5445, vinpocetine and 1–methyl–3–isobutyl–8–(methylamine)xanthine. Br. J. Phannacol. 98: 725–734.

South African Patent No. 9404018 and file history Dec. 8, 1995.

Stefanovich V. 1974. Concerning specificity of the influence of pentoxifylline on various cyclic GMP phosphodiesterases. Research Communications in Chemical Pathology and Pharmacology. 8(4):673. 1974.

Stief, et al. Preliminary report on the effect of the nitric oxide donor SIN–1 on human cavernous tissue in vivo. World J. Urol. vol. 9, pp. 237–239, 1991.

Stief, et al., "Preliminary results with the nitric oxide donor linsidomine chlorhydrate in the treatment of human erectile dysfunction", Journal of Urology, 1992, pp. 1437–144, vol. 148.

Stief, et al., "The Effect of the Specific Phosphodiesterase (PDE) Inhibitors on Human and Rabbit Cavernous Tissue in vitro and in vivo", Journal of Urology, 1998, pp. 1390–1393, vol. 159.

Stief, et al., Urology, vol. 55(1), "Effects of sildenafil on cAMP and cGMP levels in isolated human cavernous and cardiac tissue", pp. 146–150. 2000.

Stosic–Grujicic, et al., "Pentoxifylline Potentiates Nitric Oxide Production and Growth Suppression in Interferon–y–Treated L929 Fibroblasts", *Cellular Immunology*, vol. 184, pp. 105–111 (1998).

Sybertz, et al., "cGMP Phosphodiesterase Inhibition: A New Mechanism for the Discovery of Therapeutic Agents", Current Pharmaceutical Design, 1995, pp. 373–390, 1(4).

Takahashi et al. 1991. Pharmacological Effects of Adnosine on Canine Penile Erection. Tohoku J. Exp. Med. vol. 165, pp. 49–58.

Tanner, et al., Molecular Pharmacology, vol. 29, No. 5, "Identification of the phosphodiesterase regulated by muscarinic cholinergic receptors of 1321N1 human astrocytoma cells", pp. 455–460. 1986.

Tampa Y: I–Shin–Fang, vol. 4. Ren–Min–Wei–Sheng, Benjin, 1955.

Taub, et al., "Relationship between contraction and relaxation in human and rabbit corpus cavernosum", Urology, 1993, pp. 698–704, 42(6).

Tay, et al., "Psychogenic Impotence in Spinal Cord Injury Patients", Arch Phys Med Rehabil., Apr. 1996, pp. 391–393, vol. 77.

Tejada et al. 1989. Impaired Neurogenic and endothelium–mediated relaxation of penile smooth muscle from diabetic men with impotence. New England Journal of Medicine. 320:1025–1 030 (Apr. 20, 1989).

Terrett, at ai, 1996, *Sildenafil (Viagra$^{TM}$), A potent and selective inhibitor of type 5 cGMP phosphodiesterase with utility for the treatment of male erectile dysfunction,* Bioorganic & Medicinal Chemistry Letters. 6(15):1819–1824.

Thompson and Appleman, Biochem. 1979, vol. 18, No. 23 pp. 5228–5237.

Thompson, et al, 1971, *"Multiple cyclic nucleotide phosphodiesterase activities from rat brain"*, Biochemistry, 10(2):311–316.

Torphy TJ. 1988. Action ofmediators on airway smooth muscle: Functional antagonism as a mechanism for bronchodilator drugs. Agents and Actions supplement 23,37–53 (1988).

Traish et al, 1995, *"A heterogeneous population of a 1 adrenergic receptors mediates contration of human corpus cavernosum smooth muscle to norepinephrine"*, Journal of Urology. 153:222–227.

Trapani AJ, Smits GJ, McGraw DE, McMahon EG and Blaine EH. Apr. 1991. Hemodynamic basis for the depressor activity of zaprinast, a selective cyclic GMP phosphodiesterase inhibitor.

Trigo–Rocha F, Hsu GL, Donatucci CF and Lue TF. 1993. The role of Cyclic Adenosine Monophosphate, Cyclic Guanosine Monophosphate, Endothelium and Non–adrenergic, Non–cholinergic Neurotransmission in Canine Penile Erection. Journal of Urology, vol. 149:872–877 (Apr. 1993).

Trigo–Rocha, "The effect of intracavernous injection of potassium channel openers in monkeys and dogs", *Int. J. Impotence Res.*, vol. 7, pp. 41–48 (1995).

Trigo–Rocha, et al, "Intracellular Mechanism of Penile Erection in Monkeys", *Neurology and Urodynamics*, vol. 13, pp. 71–80 (1994).

Trigo–Rocha, et al, "Sodium Nitroprusside: Physiologic Effects as a Nitric Oxide Donor in Three Species", *Int. J. Impot. Res.*, vol. 7, pp. 49–56 (1995).

Trigo–Rocha, et al., "The Effect of Intracavernous Injection of Potassium Channel Openers in Monkeys and Dogs", Int. J. Impotence Res., 1995, pp. 41–48, vol. 7.

Trigo–Rocha, et al., "Nitric oxide and cGMP: mediators of pelvic nerve–stimulated erection in dogs", American Journal of Physiology, Feb. 1993, pp. H419–H422, vol. 264 (Heart Circ. Physiol. 33).

Trigo–Rocha, et al., "The Role of Cyclic Adenosine Monophosphate, Cyclic Guanosine Monophosphate, Endothelium and Nonadrenergic, Noncholigenic Neurotransmission in Canine Penile Erection", Journal of Urology, Apr. 1993, pp. 872–877, vol. 149.

Truss, et al, 1994, *"Role of the nitric oxide donor linsidomine chlorohydrate (SIN–1)in the diagnosis and treatment erectile dysfunction"*, Urology, 44(4):553–556

United States Patent No. 4,060,615, "2–Piperazinyl–6–Dimethoxyquinazolines", Nov. 29, 1977.

United States Patent No. 4,885,301, entitled "Purinone Derivatives Which Have Bronchodilator, Vasodilator and Anit–Allergic Activities"Issued Dec. 5, 1989. Coates, W. J.

United States Patent No. 6,469,012 and its file wrapper, including documents raised in re–examination proceedings.

U.S. 5,294,612 (col. 69–70; col. 72, lines 44–52).

U.S. 5,405,847 (col. 17, lines 29–35; col. 3, line 8; col. 16, line 46–52).

U.S. 5,436,233 (col. 1, lines 16, 30–32; col. 19, lines 51–55; col. 19, lines 59–61).

U.S. Patent 4,521,421 (Foreman—Method of Treating Impotence (granted Jun. 4, 1985)).

Utiger, "A Pill for Impotence", New England Journal of Medicine, 1998. pp. 1458–1459, 338(20).

Vallance P, Collier J, Moncada S. 1989. Effects of endothelium–derived nitric oxide on peripheral arteriolar tone in man. Lancet. Oct. 28, 1989.

Vittone L, Chiappe LE, Argel MI, Cingolani HE, and Chiappe GE. 1979. The mechanical and biochemical effects of pentoxifylline on the perfused rat heart.
WO94/22855 (p. 22–Table 1; p. 23; para, 3; p. 24, para. 1).
WO94/29277 (p. 1, lines 6–7; p. 3; lines 10–12; p. 4, lines 4–6).
Wallis et al., Ophthalmic Research, vol. 30(Suppl. 1), "Characterizations of retinal phosphodiesterase (PDE) isozymes and the effects of sildenafil in vitro", pp. 111, 1998.
Wallis, et al., American Journal of Cardiology, vol. 83(suppl. 5A), "Tissue distributionof phosphodiesterase families and the effects of sildenafil on tissue cyclic nucleotides, platelet function, and the contractile responses of trabeculae cameae and aortic rings in vitro", pp. 3C–12C. 1999.
Weiss, "Effects of Antihypertensive Agents on Sexual Function", Am. Fam. Physician, 1991, pp. 2075–2082, 44(6).
Weiss, Richard J., Effects of Antihypertensive Agents on Sexual Function. Am. Fam. Physician. vol. 44(6), pp. 2075–2082, 1991.
Wetzel, et al., Trends in Pharmacologcal Sciences, vol. 9, "New cardiotonic agents—promising, approach for treatment of heart failure", pp. 166–170. 1988.
Whitehead, et al, 1990, "Treatment Alternatives for Impotence", Post Graduate Medicine 88(2):139–152.
Windmeier, et al, 1997, "Pharmacological aspects of pentoxifylline with emphasis on its Inhibitory actions on hepatic fibrogenesis", Gen. Pharmac. 29(2)181–196.
WO 91/19717 (p. 77–Table; p. 71; lines 16–18; p. 71, lines 11–14).
WO 93/12095 (p. 14, para 1; pp. 14–15).
WO 94/19351 (p. 47–Table; p. 45, lines 13–26; p. 43, lines 8–12).
WO 94/28144 entitled "Cyclic GMP–binding, cycling GMP specific phosphodiesterase materials and methods" Dec. 8, 1994.
WO 95/19978 (p. 1; p. 8, line 4; p. 8, lines 6–8).
WO89/10123 (Ruffman, 1989).
WO91/19717 (Neustadt, et al., 1991).
WO93/12095 (Terrett, Jun. 24, 1993).
WO94/19351 (Tulshian, Sep. 1, 1994).
WO94/22855 (Takase, et al., Oct. 13, 1994).
WO94/29277 (Coates, et al., Dec. 22, 1984).
WO95/19978 (Daugan, Jul. 27, 1995).
Xuan, Biosis, et al., "Effects of Crocin Analogs onOcular Blood Flow and Retinal Function", Abstract PREV199900260915, J. Ocular Pharm. And Therap, Apr. 1999, pp. 143–152, 15(2).
Yajima, et al., American Journal of Ophthamology, vol. 129 No. 5, "No clinically important effects on intraocular pressure after shortterm administration of sildenafil citrate (Viagra)", pp. 675–676. 2000.
Zorgniotti, et al, 1994, "Effect of large doses of the nitric oxide precursor, L–arginine, on erectile dysfunction", International Journal of Impotence Research,6(1):33–36.
Kim et al., J. Clin. Invest., vol. 88, pp. 112–118, Jul. 1991.
Anderson KE. Pharmacology of Lower Urinary Tract Smooth Muscles and Penile Erectile Tissues. Pharmacological Reviews (1993); 45:253–308.
Archer, et al., "Hypoxic pulmonary vasoconstriction is enhanced by inhibition of the synthesis of an endothelium derived relaxing factor", Biochem. Biophys Res Commun, vol. 164, pp. 1198–1205 (1989).

Azadozoi, et al., "Endothelium–derived nitric oxide and cyclooxygenase products modulate corpus cavernosum smooth muscle tone", J. Urology, vol. 147, pp. 220–225 (1992).
Azadzoi and Tejada. 1991. Hypercholesterolemia impairs endothelium–dependent relaxation of rabbit corpus cavenosum smooth muscle. J. Urol. 146:238–240.
Benard, et al., "Self Administration in the Pharmacological Treatment of Impotence", Drugs, vol. 39, No. 3, pp. 394–398 (1990).
Born GV. 1962. "Quantative investigations into the aggregation of blood platelets", Journal of Physiology (London), vol. 162, pp. 67P–68P.
Brindley, "Cavernosal alpha–blockade: a new techique for investigating and treating erectile impotence", British Journal of Psychiat., vol. 143, pp. 332–337 (1983).
Challiss, et al., British Journal of Pharmacology, vol. 14, pp. 47–52 (1998).
Conti, et al., "Flaccidity and erection of the human penis: morphological data", annales d'urologie, vol. 7, No. 3, 115–121 (Jul. 30, 1993).
Coquil, et al., "Occurrence of the methylisopubylxanthine–stimulated cyclic GMP binding protein in various rat tissues", Biochemical and Biophysical Research Communications, vol. 127(1), pp. 226–231 (1985).
De Tajada, et al., "Regulation of Adrenergic Activity in Penile Corpus Cavernosum", J. Urol., vol. 142, p. 1117–1121 (1989).
De Tejada, et al., "Cholinergic neutrotransmission in human corpus cavernosum. Responses of Isolated Tissue", Am. J. Physiol., vol. 254, pp. H459–H467 (1988).
De Tejada, et al., "Local Control of Penile Erection", Urol. Clin. North America, vol. 15, pp. 9–15 (1988).
Eardley, et al., Current Opinion in Urology, vol. 3, No. 5, pp. II–40 (Oct. 1993).
Fischer, et al., "Current status of phosphodieterase inhibitors in the treatment of congestive heart failure", Drugs, vol. 44, pp. 928–945 (1992).
Fisher, et al., Journal of Biological Chemistry, vol. 273 No. 25, "Isolation and characterization of PDE9A, a novel human cGMP–specific phosphodiesterase", pp. 15559–15564. 1998.
Francis, et al., Journal of Biological Chemistry, vol. 255, No. 2, "Characterization of a novel cGMP binding protein from rat lung", pp. 620–626. 1980.
Frossard, et al., British Journal of Pharmacology, vol. 73, "Effects of cyclic AMP– and cyclic GMP–Phosphodiesterase inhibitors on immunological release of histamine and on lung contraction", pp. 933–938. 1981.
Furchgott RF and Zawadzki JV. 1980. The obilgatory role of endothelial cells in the relaxation of arterial smooth muscle by acetylcholine. Nature 288:373.
Gristwood, British Journal of Pharmacology, vol. 87, p. 91P (1986).
Gristwood, British Journal of Pharmacology, vol. 89, p. 573P (1986).
Holmquist, et al., "Effects of the xl–adrenoceptor antagonist R–(–)–YM12617 on isolated human penile erectile tissue and vas degernes", European Journal of Pharmacology, vol. 186, pp. 87–93 (1990).
Holmquist, et al., "L–$N^G$–nitro arginine inhibits non adrenergic, non–cholinergic relaxation of human isolated corpus cavernosum", Acta Physiol Scan., vol. 141, pp. 441–442 (1991).

Ignarro LJ and Kadowitz PI 1985. The pharmacological and physiological role of cyclic GMP in vascular smooth muscle relaxation. Ann. Rev. Pharmacol. Toxicol. 25: 171–191.

Ignarro, "Nitric Oxide: A Novel Signal Transduction Mechanism for Transcellular Communication", *Hypertension,* vol. 16, pp. 477–483 (1990).

J. Biol. Chem. 232, 1065–1076, 1958.

Kim et al. 1993. Oxygen tension regulates the nitric oxide pathway. J. Clin. Invest. 91 :437–442.

Krall, et al., *Biol. Reprod.,* vol. 39, No. 4, pp. 913–922.

Kukovetz, et al., "Evidence for Cyclic GMP–Mediated Relaxant Effects of Nitro–Compounds in Coronary Smooth Muscle", *Archives of Pharmacology,* vol. 129, pp. 129–138 (1979).

Lee, et al, "Prostaglandin E1 versus Phentolamine/Papaverine for the Treatment of Erectile Impotence: A Double–Blind Comparison", *J. Urol.,* vol. 141, pp. 549–550 (1989).

Levine, et al., "Side Effects of Self–Administration of Intracevernous Papaverine and vPhentolamine for the Treatment of Impotence", *Journal of Urology,* vol. 141, No. 1, pp. 54–57 (1989).

LJ, Lippton H, Edwards JC, Barisos WH, Hyman, Kadowitz al. PJ and Gruetter CA. 1981. Mechanism of vascular smooth muscle relaxation by organic nitrates, nitrites, nitroprusside and nitric oxide: evidence for the involvement of S–nitrosothiols as active intennediates. J. Pharm Exp. Ther. 218(3):739.

Lue, et al., "Molecular Biology of Erectile Function and Dysfunction", *Molecular Urology,* vol. 1, No. 1, pp. 55–64 (1997).

Montorsi, F. "Effect of yohimbine–trazodone on psychogenic impotence: A randomized, double–blind placebo–controlled study", Urology, Nov. 1994, pp. 732–736, 44(5).

Pickard, et al., "The effect of inhbitors of nitric oxide biosynthesis and cyclic GMP formation on nerve–evoked relaxation of human cavernosal smooth muscle", *British Journal o/Pharmacology,* vol. 104, pp. 755–759 (1991).

Porst H. 1993. Prostaglandin El and the nitric oxide donor linsidomine for erectile failure: a diagnostic comparative study of 40 patients. J. Urol. 149:1280–1283.

Radomski, et al., "An L–arginine/nitric oxide pathway present in human platelets regulates aggregation", *Proc. Natl. Acad Sci. USA,* vol. 87, pp. 5193–5197 (1990).

Rall, et al., "Formation of a Cyclic Adenine Ribonucleotide by Tissue Particles", *Journal of Biol. Chem.,* vol. 232, pp. 1065–1076 (1958).

Stief, et al., "Acetytcholine as a possible neurotransmitter in penile erection", *Journal of Urology,* vol. 141, pp. 1444–1448 (1989).

Sutherland, *Journal of Biological Chemistry,* vol. 32, pp. 1077–1091 (1958).

Taher, A., et al., "Cyclic nucleotide phosphodiesterase activity in human cavernous smooth muscle and the effect of various selective inhibitors", (Abstr.), Int. J. Impotence Res., 1992, 4 (Suppl. 2)11.

Tejada et al. Cholinergic neurotransmission in human corpus cavernosum. I. Responses of isolated tissue. Am J. Physiol. 254 (Heart Circ. Physio 12): H459–H467. 1988.

Texteria, et al., "Phosphodiesterase (PDE)4 inhibitors: anti–inflammatory drugs of the future?", *TIPS,* vol. 18, pp. 165–171 (1997).

Torphy et al., Molecular Pharmacology, vol. 39, No. 3, "Role of cyclic nucleotide phosphodiesterase isozymes in intact canine trachealis", pp. 376–384. 1991.

Torphy, et al., *Journal of Pharmacology and Experimental Therapy,* vol. 265, pp. 1213–1223 (Jun. 1993).

Virag R. 1982. Intracavernous Injection of Papaverine for erectile failure. The Lancet, Oct. 23, 1982. p. 938.

Ward, et al., "Pentoxifylline: A Review of its Pharmacodynamic and Pharmacokinetic Properties, and its Therapeutic Efficacy", *Drugs,* vol. 34, pp. 50–97 (1987).

Wespes, et al., "Systemic Complication of Intracavernous Papverine Injection in Patients with Venous Leakage", *Urology,* vol. 31, No. 2, pp. 114–115 (1988).

Wyndaele, et al., "Intracavernous Injection of Vasoactive Drugs, an alternative for treating impotence in spinal cord injury patients", *Paraplegia,* vol. 24, pp. 271–275 (1986).

Zorgniotti, et al., "Auto–Injection of the corpus cavernosum with a vasoactive drug combination for vasculogenic impotence", *Journal of Urology,* vol. 133, pp. 39–41 (1985).

*"Cambridge Antibody Technology Announces New Non–Executive Director",* Biotech Corporate Press Happenings (2003)(Ringrose).

"Pfizer to end tests of Viagra for women", Drug Week, Expanded Reporting Section, p. 466. Mar. 19, 2004.

"Proceedings of a conference held in Nice (France) on Feb. 27, 1993" sponsored by Spanish Hypertension Society and Spanish League for the Fight against Hypertension. Published by Excerpta Medica Medical Communication BV.

"Zaprinast" (Heading 14026–m), Martindale The Extra Pharmaeopoeia, 1989, p. 1423, 29th Edition.

"New Oral Agents for Erectile Dysfunction", Boston University Medical Campus, Institute for Sexual Medicine, Copyright Trustees of Boston University, Last Edition (2003).

"Viagra Receives Millennium Product Status" (Mar. 29, 1999).

ABPI Data Sheet Compendium 1990–1991, Hypovase, *Data/arm Publications Ltd,* pp. 740–742 (1991).

Adachi, "Effects of intraduodenal administration of three phosphodiesterase 5 inhibitors, zaprinast, ER–022196 and sildenafil, on penile erection in rats".

Affidavit of Peter Ellis, sworn Oct. 4, 2005, and filed in Court File No. T–1314–05, 2005.

Bauer, Pharmazeutishe Technologie, Ch. 7, pp. 202–211 (1993).

Datapram Publication Ltd., *ABPI Data Sheet Compendium,* Entry on Trental, p. 588 (1991–1992).

Eardley I and Sethia K. 1998. Pfizer document entitled "Erectile Dysfunction—Current Investigation and Management. Chapters 8 and 9."

English translation of report relating to "compounds of formula (I)" originally submitted during prosecution of 446 Patent's corresponding Japanese Patent Application. English translation filed in the opposition proceedings in respect of the 446 Patent's corresponding European Patent Application.

FDA/Center for Drug Evaluation and Research, Originator–OTCOM/DML, Updated: Mar. 8, 2001, "Postmarketing safety of sildenafil citrate (Viagra)" pp. 1–3. 2001.

Formula 1, Structures that do not come within Dr. Kruse's predicted class of compounds.

Garthwaite J, Charles SL, and Chess–Williams R. 1988. Endothelium–derived relaxing factor–release on activation of NMDA receptors suggests role as intercellular messenger in the brain. Nature 336:385.

Gennaro, et al., Common Centrally Acting Antihypertensive–containing Combinations, Pharmaceutical Sciences, Remington's, 18th edition, p. 836 (1990).

Gristwood RW. 1993. Efectos cardiovasculares de los inhibidores de la fosfodiesterasa. in Investigation en hipeternesion. presented in Nice (France), Feb. 27, 1993. p. 74–80.

*Hager's Handbuch der Pharmazeutischen Praxis,* vol. 4, pp. 675–676 (1971).

Handy, et al., "The Potency Pill", *The New York Times* (May 6, 1998).

Henderson, "Viagra earns Dome place as best of Britain" *The Times,* Early Edition Apri. 20, 1999).

IC50 values for the inhibition of phosphodiesterase enzymes by pentoxifylline reported in Pfizer and Lilli ICOS experiments.

Japanese Laid–Open Patent Publication No. 258809/1988(Der.No. 88–348774/490).

Japanese Laid–Open Patent Publication No. 58631/1962 (Der. No. 40147E/20).

Keightley, et al., Glaucoma, including Chapter 4, "Therapeutic advances in glaucoma", pp. 96–110 1986.

Li, SC., Peng–Tsao Kang Mu, vol. 14, 1596 National Research Institute of Chinese Medicine: Taipei, 1976.

Melman, "Impotence in the Age of Viagra", *Sex and Fatherhood.*

Pfizer Labs. Draft Pack Insert, Viagra™ (Sildenafil citrate) Tablets—Description, Revised: Mar. 25, 1998, pp. 1–18.

Pfizer Product Monograph for Sildenafil Citrate, *Compendium of Pharmaceuticals and Specialities* 2004.

Pfizer Product Monograph for Viagra(R), including 2006 version.

Physicians' Desk Reference 1992, entry for "Dayto Himbin Tablets" and "Yohimex".

Rang, et al., Pharmacology, Second edition, pp. 54–58 (1991).

*Rote Liste (Persantin®, INN: Dipyridamole and Trental®, INN: Pentoxifylline®, ECV (1992).*

Science. No new is good news. Dec. 1992.

*Scrip's Complete Guide to Women's Health Care,* Chapters 1–8 (2000).

Submissions to the European Patent Office in Pfizer, Mar. 8, 2002, relation to EP 0 951 908.

Takase Y, Watanabe N, Matsui M, Ikuta H, Saeki T, Adachi H, Souda S and Saito 1, 1993. The quinazoline derivatives as novel potent and selective inhibitors of cyclic GMP phosphodiesterase. Presented at the 206th American Chemical Society National Meeting, Chicago 1993.

Translation of Rote Liste 1992 (Register of Pharmaceuticals of the of the BPI), various pages including those relating to Persantin, INN: dipyridamole and Trental, INN: Pentoxifylline.

UK patent application No. 0003235.9, Pfizer.

UK patent application No. 9925970.7, Pfizer.

United Kingdom Patent Application No. 9311920.4, Ellis, et al.

Viagra CA Mylan—NOA Dec. 18, 2009, Mylan Letter to Pfizer Canada Inc., Attention: Marie Klapka, dated Dec. 18, 2009, Re: Sildenafil Citrate Tablets—25 mg, 50 mg and 100 mg.

Viagra Product Monograph, Pfizer, 2006.

Weishaar, et al., Biochemical Pharmacology, vol. 35. No. 5, "Multiple molecular forms of cyclic nucleotide phosphodiesterase in cardiac and smooth muscle and in platelets", pp. 787–800. 1986.

Yu G, Mason, H, Wu X, Krupinski J, Macor JE. PDE 5 Inhibitors for the Treatment of Male Erectile Dysfunction (MED). Bristol–Myers Squibb Pharmaceuticals Company, Albany Molecular Research, Inc., Technical Reports, vol. 7, No. 21, p. 3 (2002).

Aulton, *Pharmceutics: The Science of Dosage Form Design,* pp. 154–172 (1988).

Chaumeil, "Micronization: a method of improving the bioavailability of poorly soluble drugs", *SciFinder, Abstract* (Jun. 28, 2001).

Dorland's Illustrated Medical Dictionary, 27th ed. 1988, p. 1365.

Ellis, et al., Great Britain Patent Application No. 9311920.4, *"Therapeutic Agents"* (1993).

Fiscuss RR. 1988. Molecular mechanisms of endothelium–mediated vasodilation. Semin. Thromb. Hemost. 14 Suppl. 12–22.

Goldie, et al., "Pharmacology of the Erectile Tissue of the Canine Penis", *Pharmacological Research Communications* (1985).

*International Journal of Impotence Research,* vol. 4, Suppl. 2, p. 19 (1992).

*Physicians' Desk Reference, 46th* edition, pp. 409, 905, 1190 (1992).

Shah, et al., Self–emulsifying drug delivery systems (SEDDS) for improving in vitro dissolution and oral absorbtion of lipophilic drugs, *SciFinder, Abstract* (Jun. 28, 2001).

Butterworths Medical Dictionary, 2nd ed. P. 1385 (1978).

Campbell, et al. PCT/EP95/04066 published as WO 96/16644, "cGMP–PDE Inhibitors for the Treatment of Erectile Dysfunction", Published: Jun. 6. 1996 (Pfizer) and file history (Patent only not file history).

Canadian Letters Patent No. 2,262,268 (Pfizer) and file history Aug. 23, 1999.

Canadian Patent No. 2,044,748 (Bell 1) (and corresponding patent application).

Canadian Patent No. 2,073,226 (Bell 2) (and corresponding patent application).

Canadian Patent No. 2,203,379 (and associated patent application) 1996 Campbell.

\* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1-23, 25 and 26 is confirmed.
Claim 24 is cancelled.

\* \* \* \* \*